United States Patent
LeBoeuf et al.

(10) Patent No.: US 8,323,982 B2
(45) Date of Patent: Dec. 4, 2012

(54) PHOTOELECTROCATALYTIC FLUID ANALYTE SENSORS AND METHODS OF FABRICATING AND USING SAME

(75) Inventors: Steven Francis LeBoeuf, Raleigh, NC (US); Jesse Berkley Tucker, Schenectady, NY (US); Michael Edward Aumer, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 1118 days.

(21) Appl. No.: 11/745,056

(22) Filed: May 7, 2007

(65) Prior Publication Data

US 2008/0220535 A1  Sep. 11, 2008

Related U.S. Application Data

(60) Provisional application No. 60/879,773, filed on Jan. 11, 2007, provisional application No. 60/905,489, filed on Mar. 8, 2007.

(51) Int. Cl.
*G01N 21/00* (2006.01)

(52) U.S. Cl. .............. 436/164; 436/43; 436/62; 436/63; 436/106; 436/146; 436/149; 436/172; 436/174; 436/177; 436/181; 436/518; 436/805; 436/809; 422/52; 422/73; 422/82.01; 422/82.05; 422/82.06; 422/82.07; 422/82.08; 422/82.09; 422/82.11; 422/407; 422/501; 422/502; 422/503; 422/504; 422/507; 435/4; 435/7.1; 435/7.91; 435/7.92; 435/29; 435/287.2; 435/288.7; 506/7; 506/30; 250/208.1; 250/214.1; 250/251; 250/576; 250/373; 250/458.1; 530/408; 356/417; 356/419; 356/496; 73/23.2; 73/31.03; 204/157.15; 204/192.21; 204/403.01; 204/403.14; 205/777.5

(58) Field of Classification Search ............... 422/82.05, 422/82.06, 82.07, 52, 73, 82.01, 82.02, 82.08, 422/82.09, 82.11, 407, 501, 502, 503, 504, 422/507; 436/164, 172, 43, 62, 63, 106, 436/146, 149, 174, 177, 181, 518, 805, 809; 435/29, 4, 6, 7.1, 7.92, 7.94, 287.2, 288.7; 506/7, 30; 250/208.1, 214.1, 251, 576, 373, 250/458.1; 530/408; 356/417, 419, 496; 73/23.2, 31.03; 204/157.15, 192.21, 403.01, 204/403.14; 205/777.5
See application file for complete search history.

(56) References Cited

U.S. PATENT DOCUMENTS

| 4,240,882 A | 12/1980 | Ang et al. |
| 4,521,499 A | 6/1985 | Switzer |
| 4,541,905 A | 9/1985 | Kuwana et al. |

(Continued)

OTHER PUBLICATIONS

Mizsei, "Chemical imaging by direct methods", Thin Solid Films (2003), 436; p. 25-33.*

(Continued)

*Primary Examiner* — Dennis M White
(74) *Attorney, Agent, or Firm* — Myers Bigel Sibley & Sajovec, P.A.

(57) ABSTRACT

Fluid analyte sensors include a photoelectrocatalytic element that is configured to be exposed to the fluid, if present, and to respond to photoelectrocatalysis of at least one analyte in the fluid that occurs in response to impingement of optical radiation upon the photoelectrocatalytic element. A semiconductor light emitting source is also provided that is configured to impinge the optical radiation upon the photoelectrocatalytic element. Related solid state devices and sensing methods are also described.

65 Claims, 24 Drawing Sheets

U.S. PATENT DOCUMENTS

| | | | |
|---|---|---|---|
| 4,592,807 | A | 6/1986 | Switzer |
| 5,022,970 | A | 6/1991 | Cook et al. |
| 6,285,816 | B1 | 9/2001 | Anderson et al. |
| 6,331,438 | B1 * | 12/2001 | Aylott et al. ............ 436/172 |
| 6,361,660 | B1 | 3/2002 | Goldstein |
| 6,444,474 | B1 | 9/2002 | Thomas et al. |
| 2003/0100123 | A1 * | 5/2003 | Schanze et al. ........... 436/106 |
| 2003/0186228 | A1 * | 10/2003 | McDevitt et al. ........... 435/6 |
| 2004/0014240 | A1 * | 1/2004 | Takeguchi et al. ......... 436/518 |
| 2004/0022700 | A1 | 2/2004 | Kim et al. |
| 2004/0120844 | A1 | 6/2004 | Tribelsky et al. |
| 2004/0219056 | A1 | 11/2004 | Tribelsky et al. |
| 2005/0014129 | A1 * | 1/2005 | Cliffel et al. ............... 435/4 |
| 2005/0258816 | A1 | 11/2005 | Zen et al. |
| 2006/0123885 | A1 | 6/2006 | Yates et al. |
| 2006/0205083 | A1 | 9/2006 | Zhao |
| 2006/0240558 | A1 | 10/2006 | Zhao |
| 2006/0246342 | A1 | 11/2006 | MacPhee |
| 2009/0030350 | A1 | 1/2009 | Yang et al. |

OTHER PUBLICATIONS

Fitrainer, http://itami.com.

Anpo et al. "Photocatalytic Reduction of $CO_2$ With $H_2O$ on Titanium Oxides Anchored within Micropores of Zeolites: Effects of the Structure of the Active Sites and the Addition of Pt" *J. Phys. Chem. B*, 101:2632-2636 (1997).

Bărsan et al. "Understanding the fundamental principles of metal oxide based gas sensors; the example of CO sensing with $SnO_2$ sensors in the presence of humidity" *Journal of Physics: Condensed Matter* 15:R813-R839 (2003).

Bott "Electrochemistry of Semiconductors" *Current Separations* 17(3):87-91 (1998).

Martins et al. "Zinc oxide as an ozone sensor" *Journal of Applied Physics* 96(3)1398-1408 (2004).

Saladin et al. "Photosynthesis of $CH_4$ at a $TiO_2$ Surface from Gaseous $H_2O$ and $CO_2$" *J. Chem. Soc., Chem. Commun.* 533-534 (1995).

Skubal et al. "Detection and identification of gaseous organics using a $TiO_2$ sensor" *Journal of Photochemistry and Photobiology A: Chemistry* 148:103-108 (2002).

Skubal et al. "Monitoring the Electrical Response of Photoinduced Organic Oxideation on $TiO_2$ Surfaces" Manuscript submitted Oct. 2000 to SPIE Intl. Symposium on Environment & Industrial Sensing, Boston, MA, Nov. 5-8, 2000, sponsored by SPIE, 10 pp.

Zhang et al. "Development of Chemical Oxygen Demand On-Line Monitoring System Based on a Photoelectrochemical Degradation Principle" Environ. Sci. Technol., 40(7):2363-2368 (2006).

* cited by examiner

| Health Factor | | Diagnostic Analyte |
|---|---|---|
| Renal Health | ⇕ | Dimethyl-and Triethylamine |
| Hepatic Health | ⇕ | Dimethyl Sulfide, Thiols, Volatile Fatty Acids, Methanethiol, Ethanethiol, Ammonia |
| Diet Monitoring/ Diabetes Monitoring | ⇕ | Acetone |
| Periodontal Disease | ⇕ | Hydrogen Sulfide, Pyridine, Butadienes |
| Ovulation | ⇕ | 1-Dodecanol, Methanethiol, Methyl Sulfide, Hydrogen Sulfide |
| Respiratory Function | ⇕ | $O_2$, $CO_2$, $N_2$, NO |
| Cardiac Output | ⇕ | Acetylene |
| Lung & Breast Cancer | ⇕ | Alkanes & Benzene Derivatives |

FIG. 1
(PRIOR ART)

With each electron pulled from the analyte, a net negative (-) charge resides at the analyte/catalyst interface, and this charge can be measured electrically/optically.

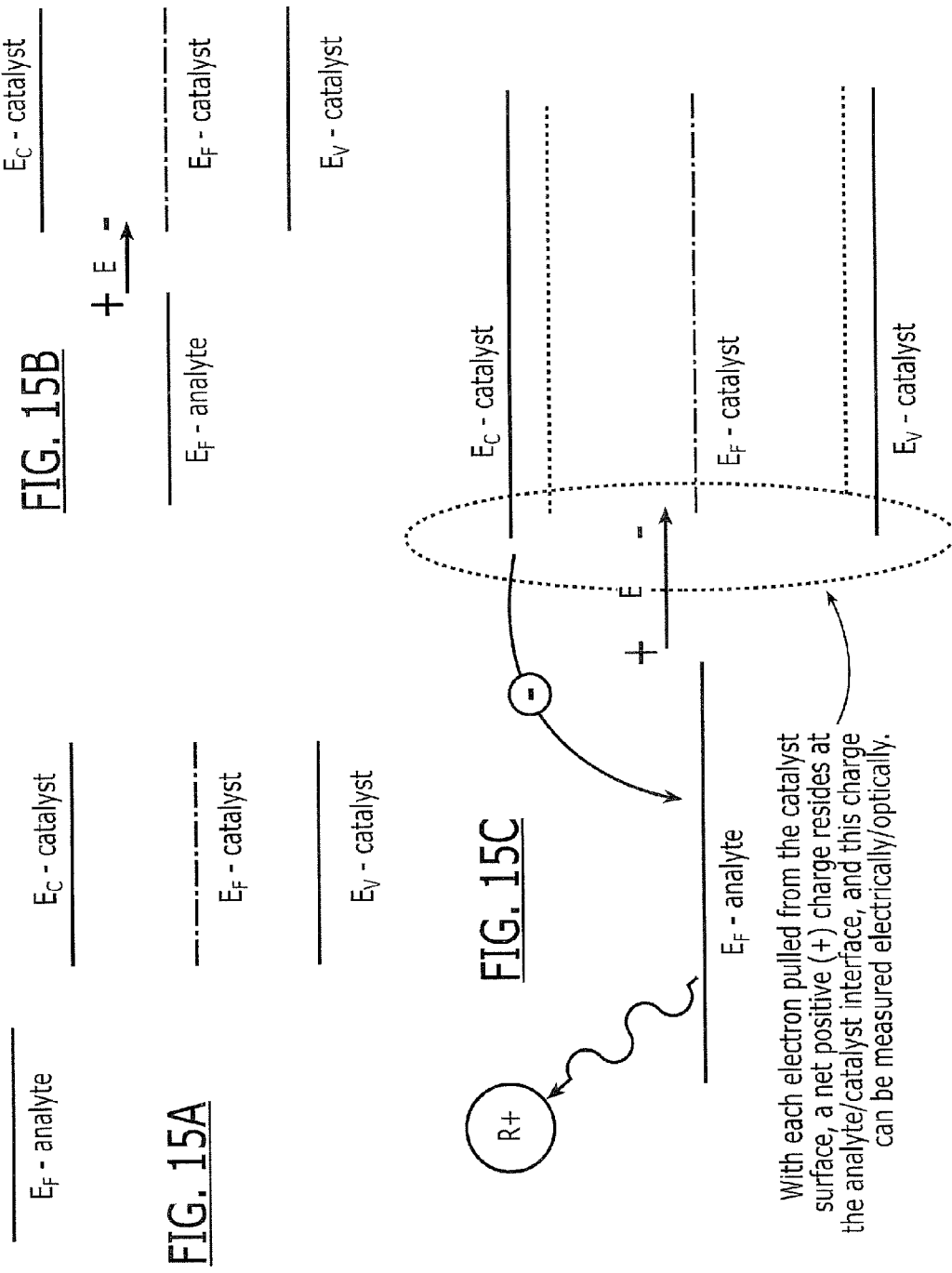

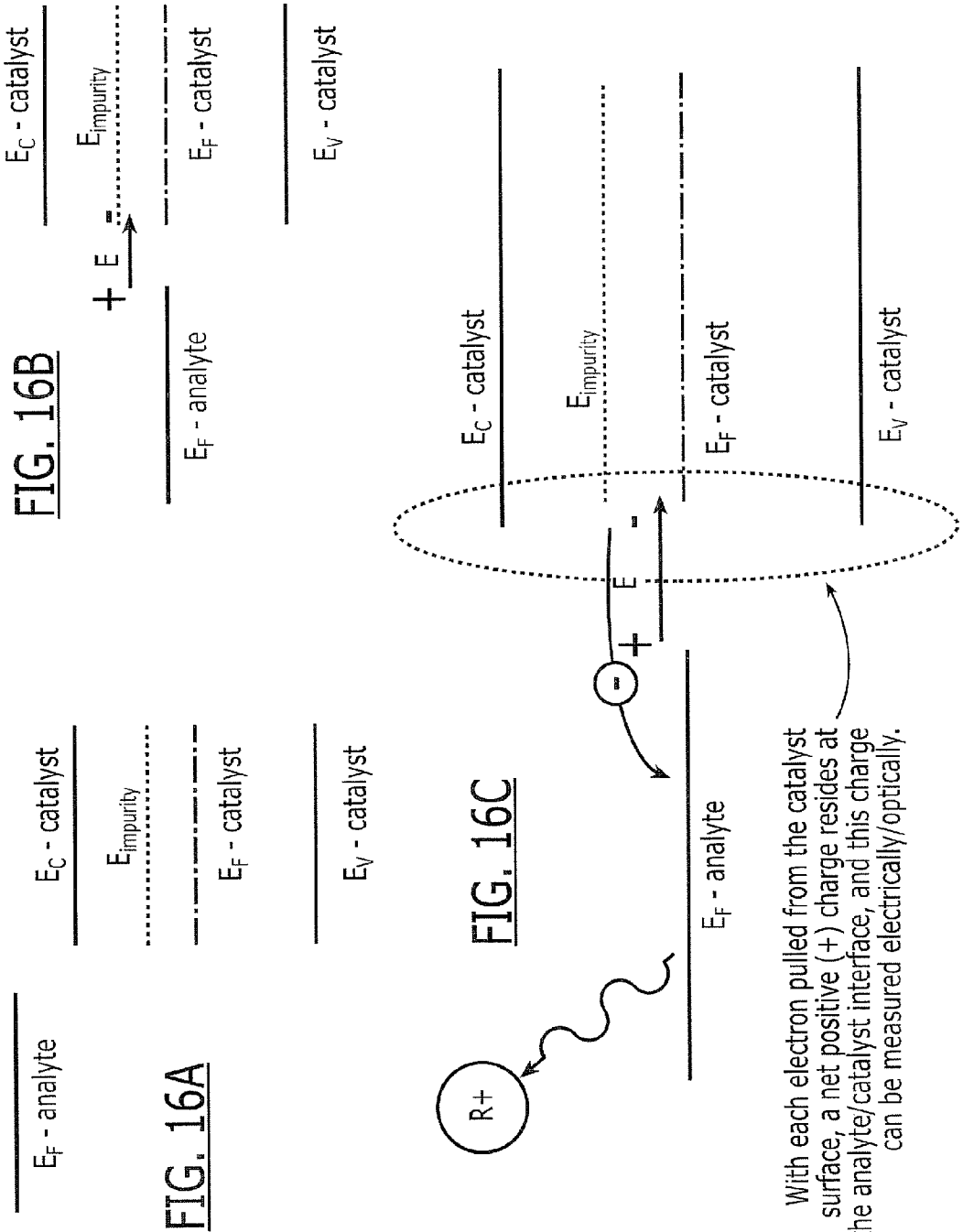

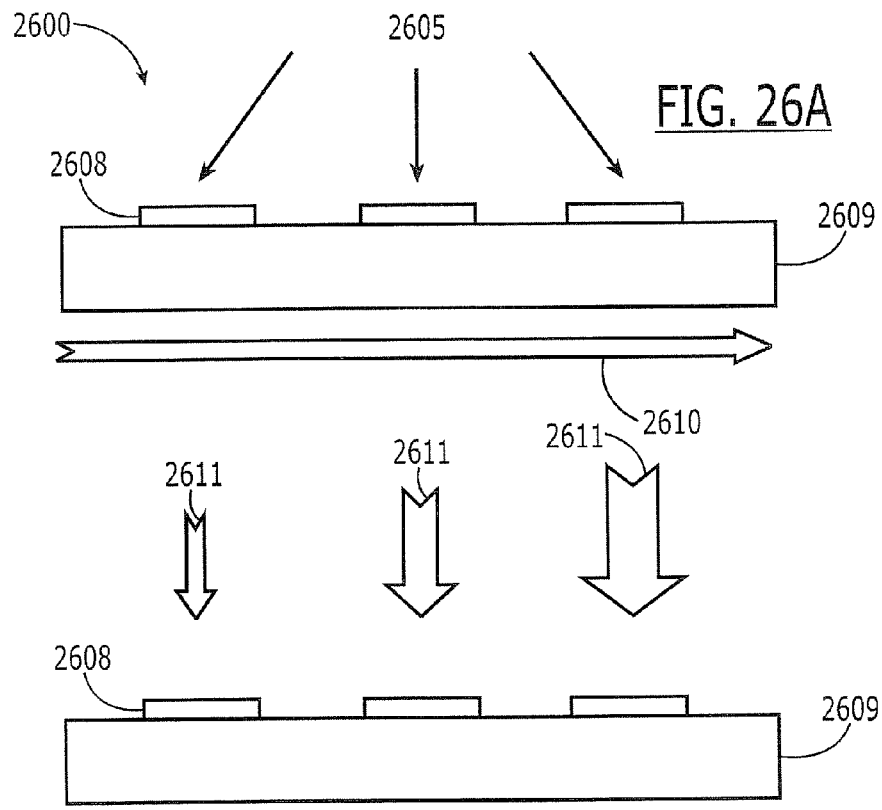
FIG. 26A
FIG. 26B
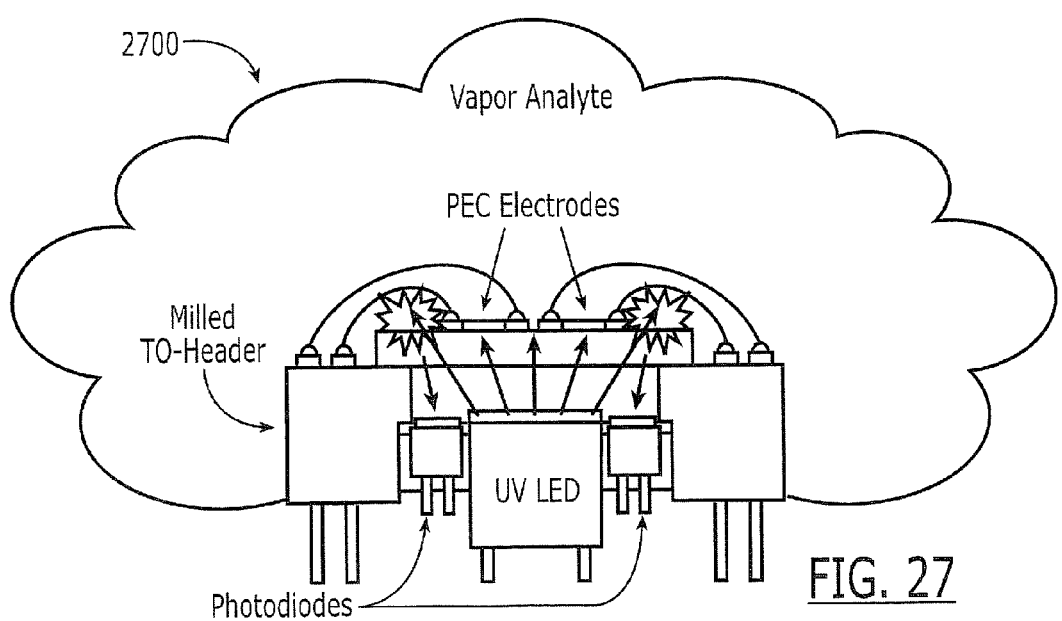
FIG. 27

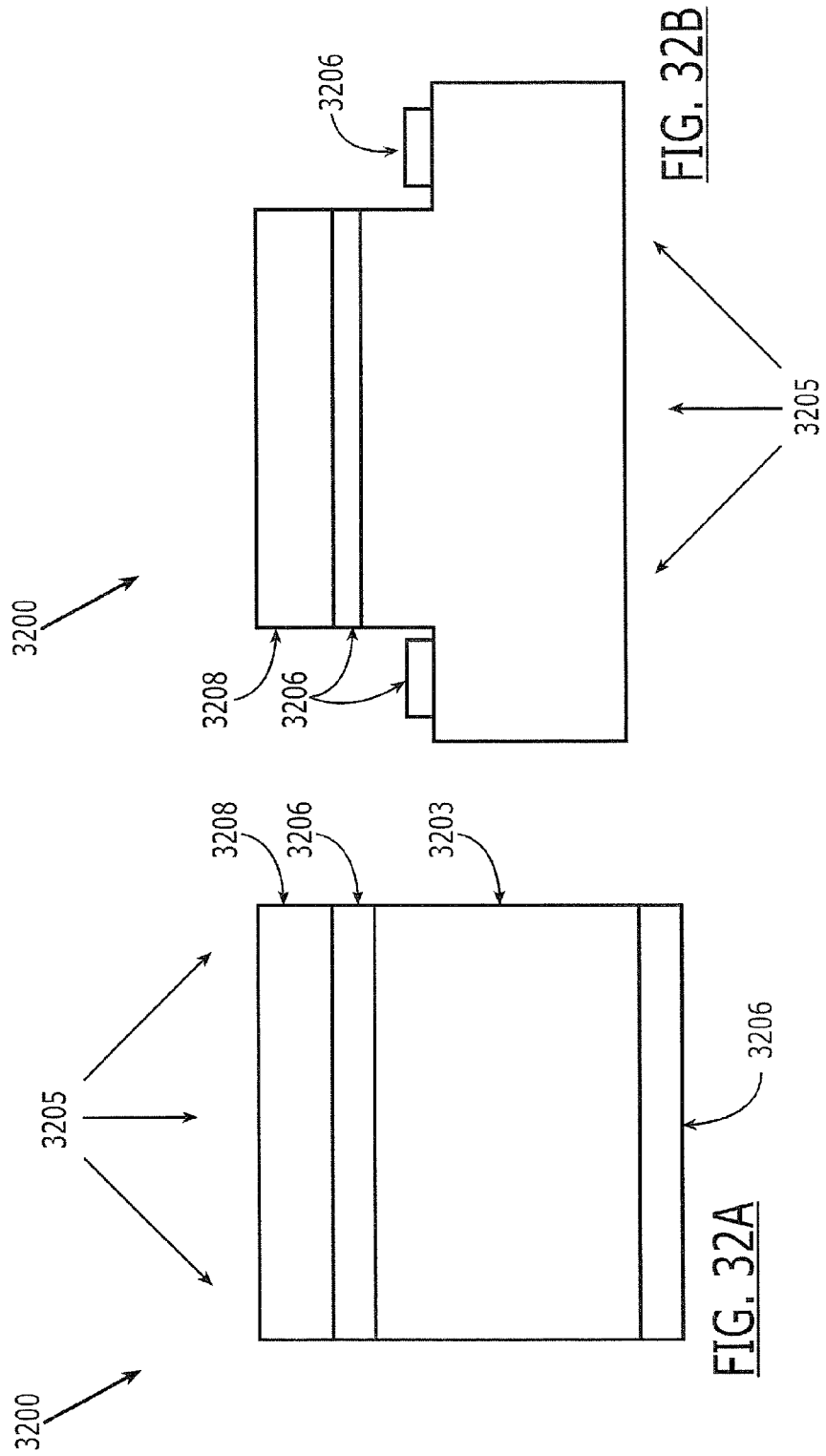

PHOTOELECTROCATALYTIC FLUID ANALYTE SENSORS AND METHODS OF FABRICATING AND USING SAME

CROSS-REFERENCE TO RELATED APPLICATIONS

This application claims the benefit of provisional Application Ser. No. 60/879,773, filed Jan. 11, 2007, entitled Device and Method of Photoelectrocatalytic Sensing, and provisional Application Ser. No. 60/905,489, filed Mar. 8, 2007, entitled Device Structures and Methods for Photoelectrocatalytic Sensing, the disclosures of both of which are hereby incorporated herein by reference in their entirety as if set forth fully herein.

FIELD OF THE INVENTION

This invention relates to sensors and methods of fabricating and using sensors, and more particularly to sensors that are configured to sense at least one analyte in a fluid, and methods of fabricating and using same.

BACKGROUND OF THE INVENTION

Sensors are increasingly being used in many consumer, commercial and other applications. For example, in the medical field, breath analysis sensors may be used to assess overall metabolism, dieting efficiency, renal and hepatic health, ovulation, diabetes, the presence of a variety of genetic disorders and/or many other effects. Moreover, environmental exposure sensors may be used to detect, for example, volatile organic compounds in a fluid.

Many different technologies have been used to provide sensors. For example, Non-Dispersive InfraRed absorption spectroscopy (NDIR) has been used for carbon dioxide analysis, and various thermal catalysis gas and vapor sensing techniques also have been used. Unfortunately, these technologies may have various shortcomings, especially in terms of allowing portable/wearable, low power and/or low cost sensors. Environmental exposure monitors have employed PhotoIonization Detectors (PID), selective absorptive polymer capacitors and/or other technologies. Again, however, these technologies may present various shortcomings, especially in terms of allowing portable/wearable, low power and/or low cost sensors.

SUMMARY OF THE INVENTION

Fluid analyte sensors, according to some embodiments of the present invention, comprise a photoelectrocatalytic element that is configured to be exposed to the fluid, if present, and to respond to photoelectrocatalysis of at least one analyte in the fluid that occurs in response to impingement of optical radiation upon the photoelectrocatalytic element. A semiconductor light emitting source is also provided that is configured to impinge the optical radiation upon the photoelectrocatalytic element.

In some embodiments, the photoelectrocatalytic element comprises a photoelectrocatalytic layer and at least one conductive contact electrically connected thereto. In other embodiments, the photoelectrocatalytic element comprises a plurality of spaced apart photoelectrocatalytic layers and a plurality of spaced apart conductive contacts electrically connected thereto. In some embodiments, a reference electrode and/or a charge balancing electrode also may be provided. In still other embodiments, a substrate is provided, and the photoelectrocatalytic element and the semiconductor light emitting source are at least partially monolithically integrated with the substrate.

In some embodiments, the photoelectrocatalytic layer comprises a plurality of layers of a given photoelectrocatalytic material having at least two different impurities therein. In other embodiments, a plurality of layers of different photoelectrocatalytic materials are provided. In some embodiments, the photoelectrocatalytic layer comprises oxide, carbide, nitride, arsenide, phosphide, sulfide and/or antimonide photoelectrocatalytic compounds and/or metal oxide(s), metal nitride(s), metallic compounds and/or semimetallic compounds thereof. Moreover, in yet other embodiments, the photoelectrocatalytic element is doped with deep level impurities, and the electro-optical source is a visible and/or Infra-Red (IR) Light Emitting Diode (LED). In still other embodiments an UltraViolet (UV) LED is used. In still other embodiments, the photoelectrocatalytic film comprises a metal oxide, and the semiconductor light emitting source comprises an UltraViolet (UV) LED. In yet other embodiments, laser diode(s) may be used.

In some embodiments, the photoelectrocatalytic element and the semiconductor light emitting source include at least one common electrical contact. Moreover, in other embodiments, the semiconductor light emitting source includes a passivation layer, and the photoelectrocatalytic element is at least partially on the passivation layer. In still other embodiments, the at least one conductive contact comprises at least two interdigitated conductive contacts.

In some embodiments, the fluid comprises a liquid and/or a gas, and the analyte can comprise a pollutant, contaminant and/or a component of the fluid. In still other embodiments, the fluid comprises respired gas, and the analyte comprises a component of the respired gas. In still other embodiments, the fluid comprises flowing air such as air in an HVAC system.

In some embodiments, the photoelectrocatalytic element is configured to respond to photoelectrocatalysis of at least one analyte in the fluid by changing a conductivity, capacitance, inductance, impedance, net charge, optical property and/or mechanical property thereof, in response to impingement of optical radiation upon the photoelectrocatalytic element. Moreover, in other embodiments of the present invention, the photoelectrocatalytic element may include a transistor, a capacitor, a microelectromechanical structure, a diode, a resistor, a semiconductor switch, an amorphous structure, a nanostructure, a piezoelectric structure, a surface acoustic wave structure and/or a heating element.

Other embodiments of the present invention may add additional elements to the fluid analyte sensors to accomplish various results. For example, a photodetector may be added to detect the optical radiation that is emitted by the semiconductor light emitting source and/or optical radiation emitted by the photoelectrocatalysis. A controller may also be provided that is configured to selectively energize the semiconductor light emitting source and to detect a response to the photoelectrocatalysis of at least one analyte in the fluid that occurs in response to impingement of optical radiation upon the photoelectrocatalytic element. In yet other embodiments, the controller may be configured to repeatedly modulate the semiconductor light emitting source and to detect an electrical response of the at least one photoelectrocatalytic element in response thereto. In still other embodiments, a wireless transmitter may be added that is responsive to the controller, to wirelessly transmit results of fluid analyte sensing.

In some embodiments, a monitor also may be added that is configured to monitor an electrical, electromagnetic, mechanical, acoustic and/or thermal response to the at least one analyte in the fluid, if present, resulting from the photoelectrocatalysis of the at least one analyte in response to impingement of optical radiation upon the photoelectrocatalytic element. In other embodiments, a monitor may be configured to monitor energy of the at least one analyte in the fluid, if present, resulting from photoelectrocatalysis of the at least one analyte in response to impingement of optical radiation upon the photoelectrocatalytic element. In still other embodiments, the monitor is configured to monitor energy as one or more forms of optical energy of the at least one analyte in the fluid.

Solid state devices according to other embodiments of the present invention can comprise a photoelectrocatalytic element, a semiconductor light emitting source and a housing that is configured to position the photoelectrocatalytic element and the semiconductor light emitting source relative to one another, such that the semiconductor light emitting source impinges optical radiation on the photoelectrocatalytic element upon electrical energization of the semiconductor light emitting source. These solid state devices may be used for sensing and/or other applications.

In some embodiments, the photoelectrocatalytic element comprises a photoelectrocatalytic layer and an electrical contact layer thereon, and the semiconductor light emitting source comprises a light emitting diode. In yet other embodiments, the photoelectrocatalytic layer includes first and second opposing faces. The electrical contact layer is on the first face. The light emitting diode impinges optical radiation on the first face and/or on the second face. Any of the other embodiments of the invention described herein may also be included in these solid state devices.

Sensing methods according to other embodiments of the present invention comprise energizing a semiconductor light emitting source to impinge optical radiation upon a photoelectrocatalytic element that is configured to be exposed to a fluid, if present, and detecting a response of the photoelectrocatalytic element in response to the energizing of the semiconductor light emitting source. Again, any of the other embodiments described herein may be included in these sensing methods. Moreover, these methods can also include repelling charged analyte from the photoelectrocatalytic element and/or biasing the photoelectrocatalytic element to reduce carrier recombination.

Finally, it will be understood by those having skill in the art that any of the embodiments described herein may be combined in various combinations and subcombinations.

BRIEF DESCRIPTION OF THE DRAWINGS

FIG. 1 summarizes a list of health factors, with associated analytes, that can be monitored through the breath.

FIGS. 15A-15C graphically illustrate fundamental physics of a photoelectrocatalytic effect, where an analyte is reduced according to various embodiments of the present invention.

FIGS. 16A-16C graphically illustrate fundamental physics of a photoelectrocatalytic effect, where sub-band gap impurities reduce an analyte at the catalyst surface, such that the analyte can be sensed electrically via sub-band gap photoexcitation according to various embodiments of the present invention.

FIGS. 26A and 26B are cross-sectional views of photoelectrocatalytic sensors according to various embodiments of the present invention that are combined with thermocatalysis according to various embodiments of the present invention.

FIG. 27 is a side view of a photoelectrocatalytic sensor according to other embodiments of the present invention that integrates photoelectrocatalytic sensing and optical sensing.

FIGS. 32A and 32B are cross-sectional views of a photoelectrocatalytic sensor according to various embodiments of the present invention, wherein the photoelectrocatalytic material is integrated into one or more layers of a diode.

DETAILED DESCRIPTION

Figure 2:
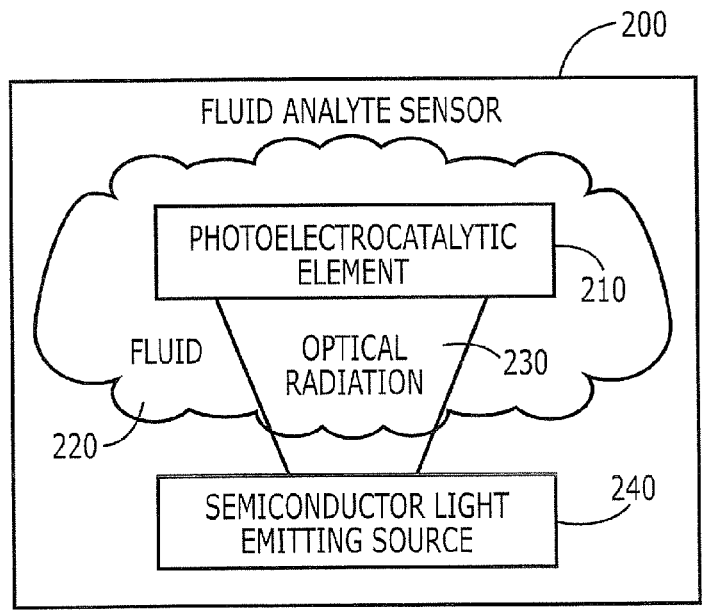
FIGS. 2 and 3 are block diagrams of fluid analyte sensors according to various embodiments of the present invention.

Embodiments of the present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention. As used herein, the term "and/or" includes any and all combinations of one or more of the associated listed items.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" "comprising," "includes" and/or "including" (and variants thereof) when used herein, specify the presence of stated features, integers, steps, operations, elements, and/or components, but do not preclude the presence or addition of one or more other features, integers, steps, operations, elements, components, and/or groups thereof. In contrast, the term "consisting of" (and variants thereof) when used in this specification, specifies the stated features, integers, steps, operations, elements, and/or components, and precludes additional features, integers, steps, operations, elements and/or components. Moreover, the term "consisting essentially of" when used in the specification, specifies the stated number of features, integers, steps, operations, elements and/or components, and precludes additional features, integers, steps, operations, elements and/or components, except for insubstantial amounts of impurities or other materials that do not materially affect the basic and novel characteristics of the stated features, integers, steps, operations, elements and/or components.

Unless otherwise defined, all terms (including technical and scientific terms) used herein have the same meaning as commonly understood by one of ordinary skill in the art to which this invention belongs. It will be further understood that terms used herein should be interpreted as having a meaning that is consistent with their meaning in the context of this specification and the relevant art and will not be interpreted in an idealized or overly formal sense unless expressly so defined herein.

It will be understood that when an element such as a layer, region or substrate is referred to as being "on" or extending "onto" another element (and variants thereof), it can be directly on or extend directly onto the other element or intervening elements may also be present. In contrast, when an element is referred to as being "directly on" or extending "directly onto" another element (and variants thereof), there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "lateral" or "vertical" may be used herein to describe a relationship of one element, layer or region to another element, layer or region as illustrated in the figures. It will be understood that these terms are intended to encompass different orientations of the device in addition to the orientation depicted in the figures.

Embodiments of the invention are described herein with reference to cross-section illustrations that are schematic illustrations of idealized embodiments (and intermediate structures) of the invention. The thickness of layers and regions in the drawings may be exaggerated for clarity. Additionally, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing. For example, variations in surface or interface roughness, porosity, morphology and/or stoichiometry differences due to materials growth/deposition techniques are included. In another example, an implanted region illustrated as a rectangle will, typically, have rounded or curved features and/or a gradient of implant concentration at its edges rather than a discrete change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the invention.

The present invention is described below with reference to block diagrams and/or flowchart illustrations of methods and/or apparatus (systems) according to embodiments of the invention. It is understood that a block of the block diagrams and/or flowchart illustrations, and combinations of blocks in the block diagrams and/or flowchart illustrations, can embody apparatus/systems (structure), means (function) and/or steps (methods) for implementing the functions/acts specified in the block diagrams and/or flowchart block or blocks.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated.

Some embodiments of the invention can provide devices and/or methods for sensing various analytes within a fluid via the photoelectrocatalytic (PEC) effect. Some embodiments can integrate a solid state optical emitter with one or more photoelectrocatalytic films for sensing various analytes within a fluid and/or other applications. In some embodiments, the solid state optical emitter is an UltraViolet (UV) Light Emitting Diode (LED), and the photoelectrocatalytic films include metal oxide films in an array. These embodiments can allow multiple species in fluid mixtures to be qualified and quantified independently in real time by the photoelectrocatalytic response at each electrode. In other embodiments, the photoelectrocatalytic array fluid sensor may be applied towards respiration monitoring, for monitoring overall metabolism and/or diagnosing various health conditions through the breath.

In 1983, Manolis reported on the broad diagnostic potential of breath analysis in medical applications, citing roughly 200 compounds, mostly Volatile Organic Compounds (VOCs), present in the breath of normal human patients. In this report, Manolis highlighted that breath monitoring can be used to assess overall metabolism, dieting efficacy, renal and hepatic health, ovulation, diabetes and/or the presence of a variety of genetic disorders as illustrated in FIG. 1. Breath monitoring may have one or more of the following advantages over competing approaches: breath samples can be easy, fast, and cost effective to collect; respired gas monitoring can often provide the same information as arterial blood gas testing, but with a noninvasive, real-time monitoring approach; breath samples generally are chemically less complex than blood or urine, which can reduce or preclude the need for costly sample preparation prior to chemical analysis; and chemical breath analysis can provide a direct method of monitoring respiratory function that may not be easily attainable by other means.

At the time of Manolis' report, the instrumentation for breath analysis generally was bulky and expensive in comparison with blood and urine analysis. Today, a variety of potential solutions exist for measuring $CO_2$ levels and low-density VOCs, but these technologies may not provide a holistic solution for monitoring many or all relevant exhaled gases and vapors in a single, portable, compact, battery-powered device. Such a device may be used not only for hospital patient monitoring, but also for paramedics, physical therapy clinics, and home health monitoring.

For example, currently two technologies may aim to provide low-cost, portable respiration monitoring: Non-Dispersive InfraRed absorption spectroscopy (NDIR) for carbon dioxide analysis, and thermal catalysis gas and vapor sensing. An NDIR-based $CO_2$ monitor can be used to measure carbon dioxide via infrared absorption. Similarly, thermal catalysis can be applied towards measuring carbon dioxide and other gases via high temperature catalytic reactions. However, infrared absorption may only be effective for carbon dioxide sensing, and thermal catalysis sensors may use excessively high input power and may be too hot for wearable sensor applications. One current portable gas monitor solution combines the NDIR approach with an electrochemical approach to cover a wider range of gaseous species, but these incompatible technologies may dramatically increase system size, boost power demands and/or complicate maintenance. Thus, these technologies may be characterized by potentially serious shortcomings in the context of portable/wearable health monitors.

Of the presently available technologies, thermal catalysis may be the most flexible, as a variety of gases can be sensed, in some cases selectively from other gases in a mixture, by monitoring the electrode response at high temperatures. In these sensors, patterned metal-oxide electrodes serve as thermal catalytic films, and at elevated temperatures catalyzed gas reactions are measured as changes in the bulk or surface conductivity within the catalytic films. However, the high temperatures that are used may make these sensors unsuitable for wearable use. Furthermore, the high temperatures can negatively affect sensor sensitivity, selectivity, lifetime, initial turn-on time, response time, power consumption and/or reliability.

In contrast, some embodiments of the invention can catalyze gas reactions in a catalytic film by employing photocatalysis as opposed to thermal catalysis. For example, through the known photocatalytic effect of titanium dioxide, organic vapors are adsorbed onto the titania (titanium dioxide) surface and dissociated via photoelectric radical formation. Similarly, other gaseous species, such as carbon monoxide and carbon dioxide, can be oxidized or reduced on the titania surface. By integrating electrodes with the titania film, the electrical properties of the film in response to photoelectrocatalyzed gaseous species can be monitored and related to the concentration of the species, in some embodiments of the invention.

In other embodiments, a photoelectrocatalytic array fluid sensor may be applied to analyte monitoring, for monitoring volatile organic chemicals, airborne pollutants, liquid pollutants, and the like. In particular, despite the growing commercial market for affordable, low-profile environmental exposure monitors, commercially available solutions do not appear to satisfy the desires of end users. In contrast, some embodiments of the invention can provide compact, wearable, low-power photoelectrocatalytic sensors and can combine metal-oxide photoelectrocatalytic sensors with commercially available UV LEDs, which can potentially satisfy consumer needs for broad sensor functionality, virtually unnoticeable size and weight and/or fewer recharges per week.

To potentially satisfy commercial markets for personal environmental exposure monitors, it may be desirable for an environmental sensor module to satisfy one or more of the following criteria. In particular, the sensor module should be: compact (e.g., less than about 10 $cm^3$); low power (e.g., less than about 10 mW average power, suitable for miniature rechargeable batteries); low-profile (e.g., virtually unnoticed by the user); multifunctional (able to monitor a variety of airborne species in the same module); affordable; sufficiently responsive in turn-on and turn-off time; robust (indoors and outdoors); reusable; and/or long-lasting (e.g., up to 2 years or more). In today's marketplace, a variety of commercially available products may provide affordable solutions for monitoring VOCs. However, although many of these solutions may be well developed for industrial use, these technologies may not be readily usable for personal, wearable monitoring of VOC exposure.

For example, commercial Photo-Ionization Detectors (PIDs) can demonstrate very low detection limits of volatile organic vapors (parts per billion), such as acetone, toluene, benzene, octane, etc. However, even the most compact of these sensors generally is much too large and costly, may use high operating power (e.g. more than about 100 mW), and may operate over a narrow operating temperature range. Conventional tin oxide VOC sensors, a potentially affordable alternative to PIDs, may indeed be compact, robust, low-profile and/or sensitive to various gases (VOCs, ozone, CO, etc.), but they also may operate at high operating temperatures (for thermocatalysis), may lack vapor selectivity, and/or may use operating powers that are too high for multi-day operation using a small rechargeable battery.

Another sensing technology is the selective absorptive polymer capacitor. Researchers are currently testing compact chemical sensing modules via polymer-filled capacitor technology. These sensors may be compact, may use low (sub-milliwatt) operating power, and may be easily integrated into compact integrated circuits. However, concerns may remain with long-term reliability and/or sensor selectivity during wearable use. In particular, polymer materials can be especially sensitive to humidity, temperature and/or aerosolized interferents, especially over long-term operation. Further, it may be difficult to integrate absorptive polymer VOC sensors with sensors for ozone, carbon monoxide, and other gases on the same sensor module. Additionally, absorptive polymers may pose concerns of response time, saturation and/or desorption time, since adsorption of analyte into the film generally is part of the sensing process.

In contrast, some embodiments of the invention can integrate UV LEDs with metal oxide catalysts, for a compact photoelectrocatalytic device. For monitoring VOCs, one or more of the following potential advantages may be provided by a photoelectrocatalytic device according to some embodiments of the invention, over standard thermal catalysis approach: a wider variety of vapors can be sensed using the same catalyst; high temperatures (and thus high operating powers) may not be needed for catalysis; because surface adsorption may be dominated by the unique photoelectrochemical dynamics of each gaseous species, as opposed to the more ambiguous thermodynamics of each species, greater selectivity may be afforded using the same photocatalytic film; by modulating the UV LED photo-excitation source, much higher sensitivity (e.g., about 100-10,000×) may be achievable through a lock-in detection approach; and/or higher detection speeds can be realized.

Moreover, some embodiments of the invention may provide for: measuring multiple gases and vapors simultaneously using multiple electrodes; implementing multiple catalysts to allow improved selectivity among various species; integrating commercially available UV LEDs within a PEC array; and/or using PEC sensors in a portable respirometer for monitoring health conditions, diseases and/or health factors in the breath. Yet other embodiments can provide portable PEC sensing devices and methods for personal environmental exposure monitoring of volatile organic compounds (VOCs), polycyclic aromatic hydrocarbons (PAHs), ozone and/or other airborne pollutants and toxins.

FIG. 2 is a block diagram of a fluid analyte sensor according to various embodiments of the present invention. Referring to FIG. 2, a fluid analyte sensor 200 includes a photoelectrocatalytic (PEC) element 210 that is configured to be exposed to a fluid 220, if present, and to respond to photoelectrocatalysis of at least one analyte in the fluid that occurs in response to impingement of optical radiation 230 upon the photoelectrocatalytic element 210. A semiconductor light emitting source 240 is configured to impinge the optical radiation 230 upon the photoelectrocatalytic element 210. It will be understood by those having skill in the art that the arrangement of the elements in FIG. 2 is merely illustrative, so that the photoelectrocatalytic element 210 may be exposed to the fluid on one or both faces thereof, and the semiconductor light emitting source 240 may impinge the optical radiation 230 on one or both faces of the photoelectrocatalytic element, which may be the same face and/or a different face as that which is exposed to the fluid 220. Various arrangements of photoelectrocatalytic elements 210 and semiconductor light emitting sources 240 in fluid analyte sensors 200 will be described below. Moreover, many different embodiments of the photoelectrocatalytic elements 210 and semiconductor light emitting sources 240 themselves will also be described.

Figure 3:
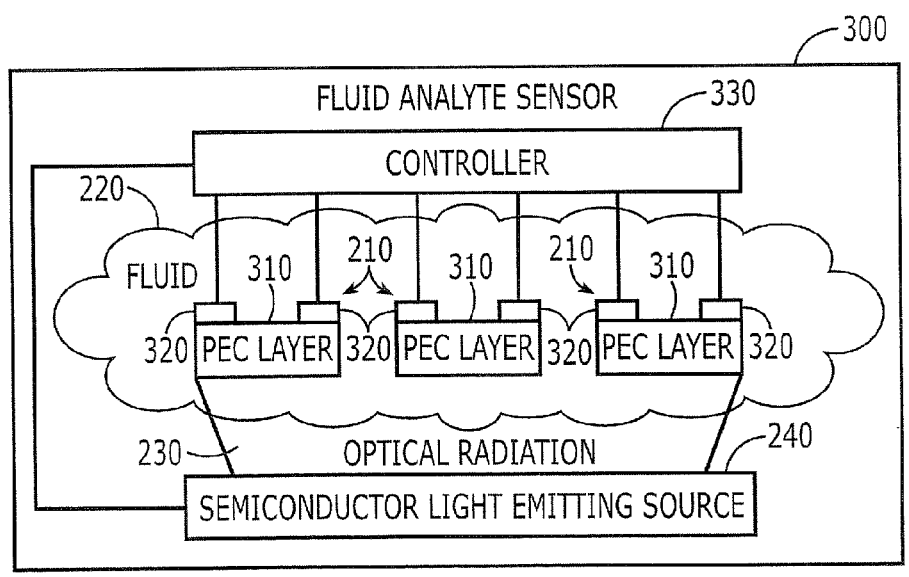

FIG. 3 is a block diagram of fluid analyte sensors 300 according to various other embodiments of the present invention. As shown in FIG. 3, a photoelectrocatalytic element 210 may include a photoelectrocatalytic layer 310 and one or more conductive contacts 320 electrically connected thereto. Various configurations of photoelectrocatalytic layers 310 and contacts 320 may be provided, as will be described below. For example, a plurality of spaced apart photoelectrocatalytic layers 310 and a plurality of spaced apart conductive contacts 320 electrically connected thereto may be provided as shown in FIG. 3. In other embodiments, contactless sensing may be employed so that conductive contacts 320 need not be used. In still other embodiments, the photoelectrocatalytic element 210 can include other regions or structures.

A substrate, described in detail below, may be used to maintain the photoelectrocatalytic layers 310 in spaced apart relationship. The photoelectrocatalytic layers 310 may comprise a plurality of layers of a given photoelectrocatalytic material having at least two different impurities therein and/or a plurality of different photoelectrocatalytic materials. In still other embodiments, a single photoelectrocatalytic layer 310 may include various regions therein that provide at least two different impurities therein and/or at least two different photoelectrocatalytic materials therein. Many specific examples will be provided below. Moreover, the physical arrangement of the photoelectrocatalytic elements 210 and the semiconductor light emitting source 240 may vary considerably, as described in greater detail below.

FIG. 3 also illustrates a controller 330, also referred to herein as "electronics," that may be used to receive the signals from the conductive contacts 320, and may also be used to energize the semiconductor light emitting source 240. Various embodiments of controllers will also be described in detail below. Moreover, many other elements may be added to the basic configurations of FIGS. 2 and 3, as will be described in greater detail below.

Figure 4:
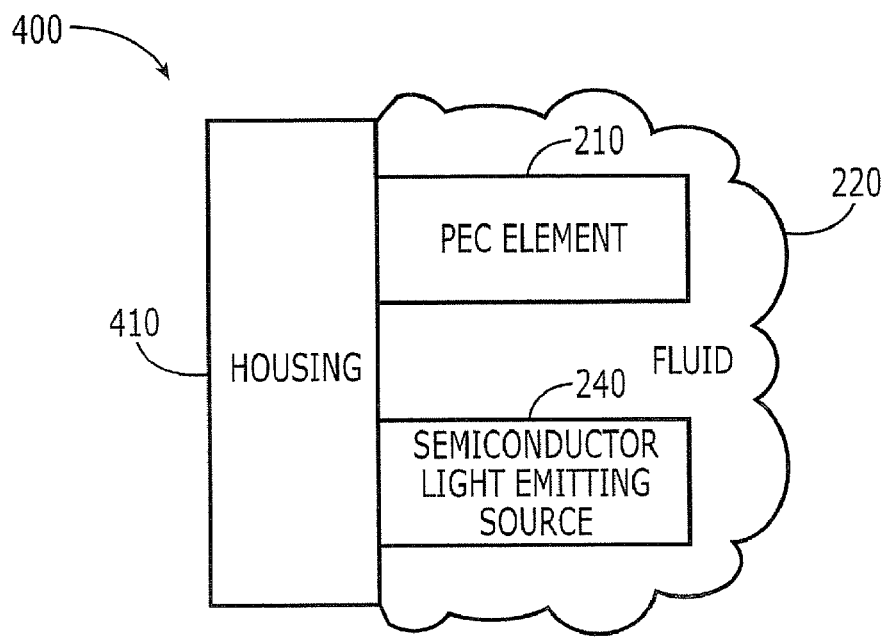
FIG. 4 is a block diagram of a solid state device according to various embodiments of the present invention.

FIG. 4 illustrates a mechanical construction of a solid state device 400 according to various embodiments of the invention. These embodiments of solid state devices 400 include a photoelectrocatalytic element 210 and a semiconductor light emitting source 240. A housing 410 is configured to position the photoelectrocatalytic element 210 and the semiconductor light emitting source 240 relative to one another, such that the semiconductor light emitting source impinges optical radiation on the photoelectrocatalytic element 210 upon electrical energization of the semiconductor light emitting source 240. It will be understood by those having skill in the art that the housing block 410 is used to conceptually illustrate any housing that is configured to position the photoelectrocatalytic element 210 and the semiconductor light emitting source 240 relative to one another, and includes single-piece or multi-piece housings that are configured to position the photoelectrocatalytic element 210 and the semiconductor light emitting source 240 relative to one another in any orientation, including adjacent or touching one another, as long as the semiconductor light emitting source impinges optical radiation on the photoelectrocatalytic element 210 (directly and/or via one or more optical elements) upon electrical energization of the semiconductor light emitting source 240. The photoelectrocatalytic element 210 may be exposed to a fluid 220 to provide a fluid analyte sensor. However, devices 400 may also be used in applications other than fluid analyte sensing.

Figure 5:
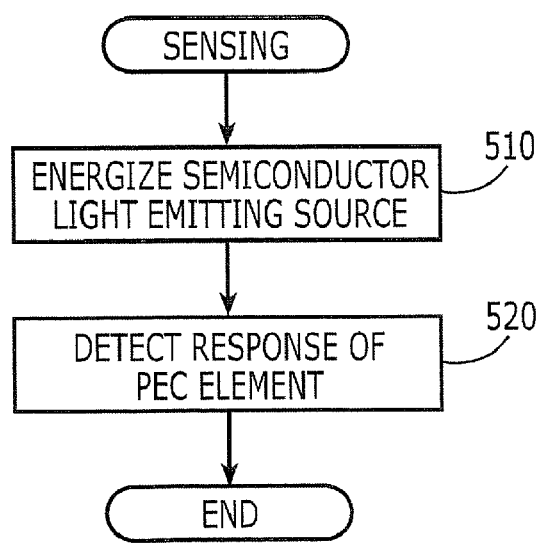
FIG. 5 is a flowchart of operations that may be performed to provide sensing according to various embodiments of the present invention.

FIG. 5 is a flowchart of operations that may be performed to provide sensing according to various embodiments of the present invention. In particular, as illustrated in FIG. 5, at Block 510, a semiconductor light emitting source is energized to impinge optical radiation upon a photoelectrocatalytic element. At Block 520, a response of the photoelectrocatalytic element is detected, in response to the energizing of the semiconductor light emitting source. Various other operations may be performed to process the detected response, to transmit the detected response and/or the processed results thereof, and/or to provide other functionality, as will be described in detail below.

Some embodiments of the invention may provide fluid analyte sensors capable of identifying and quantifying multiple species within a fluid in real time. The fluid analyte sensors can combine semiconductor optical emitters with photoelectrocatalytic elements, enabling a low-cost, low-power, low-profile, portable (in some embodiments battery-powered) and/or real-time gas monitor. In some embodiments, a fluid analyte sensor operates as a respiration monitor capable of identifying and/or quantifying multiple respired gases and vapors simultaneously and noninvasively in real time. In contrast with existing gas and vapor sensing products, some embodiments of the invention can selectively sense, quantify, and/or qualify $O_2$, $CO_2$, $N_2$ and/or various volatile organic chemicals simultaneously using the same monolithic device. This can enable the rapid assessment of various health factors with a simple compact device, including cardiopulmonary status, renal status, hepatic health, etc.

Figure 6:
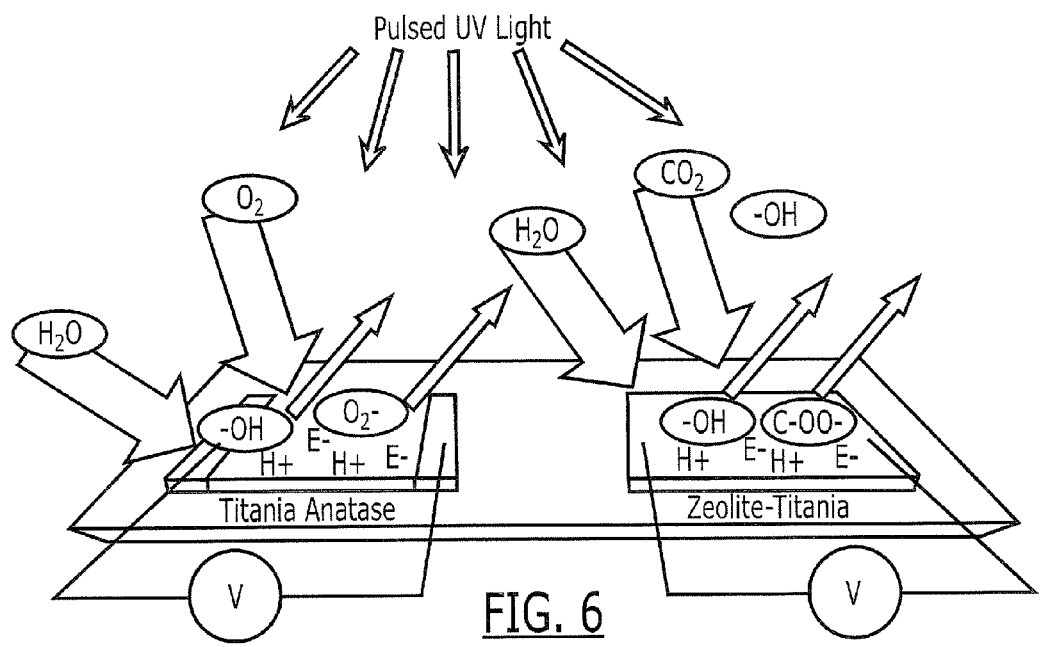
FIG. 6 conceptually illustrates photoelectrocatalytic sensing devices and methods according to various embodiments of the present invention.

Some embodiments of the invention can operate by monitoring the electrochemical response to the photocatalytic effect of titania, zirconia and/or various other metal oxides, in the presence of respired gases and vapors. For example, as shown in FIG. 6, with the adsorption of water vapor at the titania surface, ultraviolet light will generate hydroxide radicals capable of oxidizing volatile organic compounds (VOCs) at the surface. Similarly, oxygen adsorbed under UV excitation generates superoxide anions which also can oxidize VOCs. This results in changes in the conductivity of the titania film in response to the analyte absorbed and ionized at the surface. According in some embodiments, the unique photoelectrocatalytic signatures for various respired gases (oxygen, carbon dioxide, nitrogen and/or the like) and VOCs (ethanol, methylene chloride, benzene, acetone, xylene, isopropanol and/or the like) can be monitored in real time, without needing high temperatures. In some embodiments of the invention, analyte selectivity may be achieved by monitoring the transient electrical response that can be unique to each ionized species. In other embodiments, analyte selectivity may be achieved by monitoring and comparing the electrical response from multiple electrodes having preferentially selective catalysts, as illustrated in FIG. 6. Other techniques for achieving analyte selectivity will be described in detail below. Monitoring VOCs in exhaled breath can be used to detect and diagnose various health factors and diseases, as was illustrated in FIG. 1.

Conventionally, the photocatalytic effect of titania has been applied towards the biological sterilization of air and water. In photoelectrocatalytic sensing according to some embodiments of the invention, the photocatalyzed byproducts of gas and vapor oxidation are not simply discarded but rather are monitored electrically as illustrated by the schematic voltmeter symbols (V) in FIG. 6. The oxidized byproducts may be adsorbed onto (and/or partially absorbed into) the titania film, proportionately changing its conductivity, capacitance and/or other property, and the resulting photoelectrocatalytic response is measured electrically between two or more conductive (e.g., metallic) contacts. More specifically, photoionized electron-hole pairs (E− and H+) selectively ionize exhaled gases ($O_2$, $H_2O_2$, $CO_2$, organic vapors, etc.) adsorbed near the surfaces of the titania photocatalysts. The adsorbed radicals temporarily alter the titania conductivity, measured electrically before desorption. This can provide a convenient tool for monitoring the presence and/or relative intensity of adsorbed gases and vapors. Depending on the stoichiometry and morphology of the metal oxide film, different gases can be selectively adsorbed and detected.

The species of the photocatalyzed vapor can be qualified by monitoring the time-dependent electrical response, measuring the current-voltage profile and/or by a selective (or quasi-selective) photocatalytic reaction. Similarly, the volumetric concentration of the analyte can be monitored by the concentration-dependent intensity of the electrical response at the photocatalytic electrodes (i.e., the photoelectrocatalytic response to the analyte). The temporal response may be governed primarily by the adsorption/desorption rate of the gaseous species within the metal oxide film, and this in turn can be controlled to some degree by the thickness and/or morphology of the film. For example, thicker films and rougher surfaces may typically result in a longer absorption/desorption rate.

For monitoring respired gases and vapors, one or more of the following potential advantages may be provided by a photoelectrocatalytic approach according to some embodiments of the invention, as opposed to the standard thermal catalysis approach:

A wider variety of vapors can be sensed using the same catalyst;

High temperatures (and thus high input powers) are not needed to catalyze a reaction;

Because surface adsorption may be dominated by the potentially unique photoelectrochemical dynamics of each gaseous species, as opposed to the more ambiguous thermodynamics of each species, greater selectivity may be afforded using the same photocatalytic film;

By modulating the photo-excitation source, much higher sensitivity (e.g., 100-10,000 times) may be achievable through a lock-in detection approach;

Millisecond-level detection speeds can be realized, as opposed to timescales of seconds and minutes. This speed may be especially problematic for traditional absorptive dielectric sensors and high-temperature catalytic sensors;

Initial startup does not require a heating up time duration, so that sensing can begin quickly, e.g., within milliseconds. This may be especially useful in intermittent polling applications, where a long heat up/cool down may limit the speed of polling and/or increase the desired power consumption for a given polling instance; and/or High temperatures are not required, so safety may be provided in environments that may be contaminated with explosive or flammable vapors.

Indeed, photoelectrocatalytic sensing according to some embodiments of the invention may provide promising solutions for reducing or eliminating the need for thermal catalysis. However, because most metal oxide films are characterized by high band gaps in the UV range, photoelectrocatalytic sensing may exchange the potential problem of high temperatures for the challenge of a low-cost, compact, ultraviolet source. Fortunately, compact commercially available UV LEDs are now widely available and can be integrated into a photoelectrocatalytic electrode array as will be described in detail below. Thus, some embodiments of the invention can enable a low-cost, low-temperature solution for monitoring gaseous analytes within a wearable respiration monitor.

Figure 7:
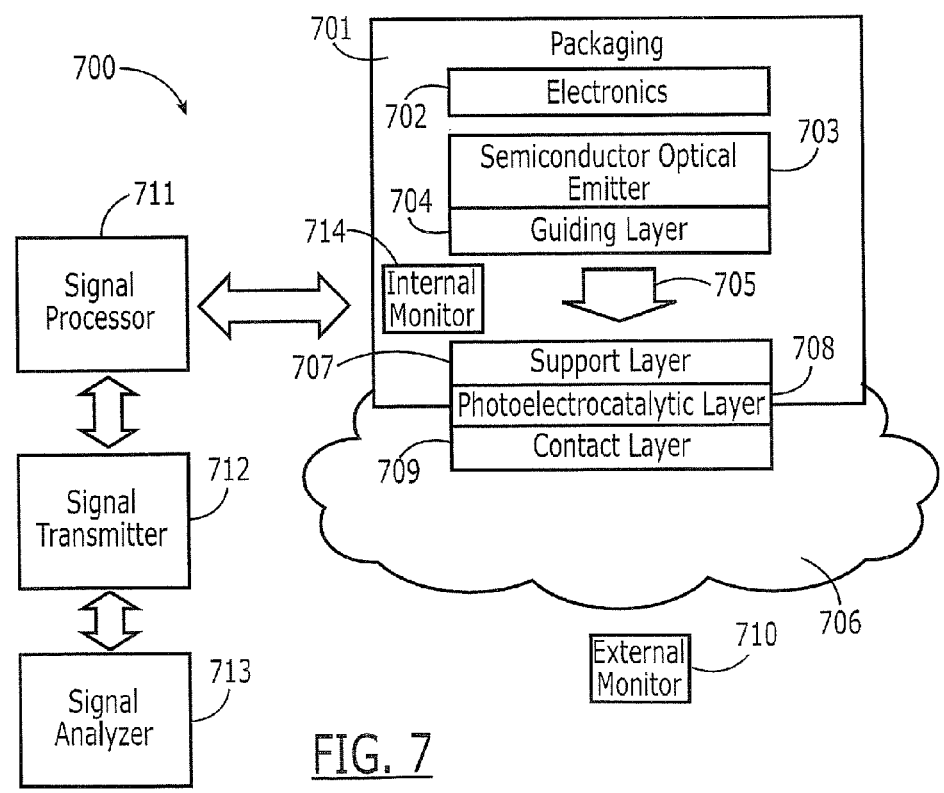
FIG. 7 is a block diagram of a photoelectrocatalytic sensor according to various embodiments of the present invention.

FIG. 7 illustrates a photoelectrocatalytic sensor and real-time monitor 700 of various fluid analytes 706 according to some embodiments of the invention. As shown in FIG. 7, a photoelectrocatalytic layer 708 is integrated with a support layer 707 and a contact layer 709 for communication with a signal processor 711. In some embodiments, the support layer 707 may comprise one or more conductive, insulating and/or semiconductor layers that can perform various mechanical, electrical and/or optical functions in the photoelectrocatalytic sensor 700. The composition of the support layer may vary based on the particular application and configuration of the photoelectrocatalytic sensor 700, and also may not be needed in other embodiments. In some embodiments, the contact layer 709 and the photoelectrocatalytic layer 708 form a photoelectrocatalytic element 210, as was described in connection with FIGS. 2-4. The photoelectrocatalytic layer 708 is optically activated ("photo-excited" or "optically pumped") by a semiconductor light emitting source 703, also referred to herein simply as a "semiconductor optical emitter." Photo-excitation generates excited electrons and holes capable of catalyzing surface reactions between the photoelectrocatalytic layer 708 and the analyte 706. The semiconductor optical emitter 703 may have a guiding layer 704 to help guide optical energy 705 generated by the semiconductor optical emitter 703 towards the photoelectrocatalytic layer 708. The guiding layer may physically contact and/or be spaced apart from the support layer 707. Other optical elements such as optical fibers, mirrors and/or lenses may be provided. The semiconductor optical emitter 703 can be located at any orientation that allows optical energy 705 to fall on the photoelectrocatalytic layer 708. Power and control electronics 702 (which may correspond to the controller 330 of FIG. 3) may be integrated into a collective housing or package 701 with the semiconductor optical emitter 703, the guiding layer 704, the support layer 707, the photoelectrocatalytic layer 708 and the contact layer 709. Signals generated in the photoelectrocatalytic layer 708 through the interaction with one or more analytes 706 may be sent to a signal processor 711 and transmitted by a signal transmitter 712 to a signal analyzer 713 to generate desired information from the photoelectrocatalytic sensing. The links between the electronics 701, signal processor 711, signal transmitter 712 and signal analyzer 713 may be wired and/or wireless. In some embodiments, an external monitor 710 may monitor photoelectrocatalytic-related activity in or about the photoelectrocatalytic layer 708. An internal monitor 714 also may be used in some embodiments, as will be described in detail below.

The word "monitoring" refers to the act of measuring, quantifying, qualifying, estimating, calculating, interpolating, extrapolating, inferring, deducing, or any combination of these actions. More generally, "monitoring" refers to a way of getting information via one or more sensing elements. "Respiration monitoring" includes monitoring oxygen, carbon dioxide, nitrogen, carbon monoxide, volatile organic chemicals, and/or other respired gases and/or vapors. Generally, the use of the term "fluid" refers to liquids, gases, vapors, plasmas and/or particles. For the sake of simplicity herein, a "vapor" is considered to be a type of gas. However, embodiments of the present invention are applicable to a variety of fluids and can be applied to these fluids by those skilled in the art without deviation from the intent of the present invention. The terms "optically pumped" or "photo-excitation" refer to optical energy that is introduced into a material and the optical energy interacts with the material such that excited states are generated in the material. Typically these excited states are photoionized electron-hole pairs in a solid-state material, but other types of excited states may exist for various materials. The "photoelectrocatalytic" reaction refers to the process of generating a catalytic reaction at, near and/or within a material via optical pumping of the material such that photoexcited states generated in the material can interact with one or more analytes at the surface of the material. The word "analyte" means any substance being identified and/or measured by a sensor. Finally, the terms "semiconductor light emitting source," "semiconductor optical source," "semiconductor optical emitter" and/or variants thereof may be used interchangeably herein.

The photoelectrocatalytic layer 708 may be any solid or reasonably solid material capable of generating electrons and/or holes in response to optical excitation 705. In some embodiments, the photoelectrocatalytic layer 708 comprises a solid metal oxide and/or metal nitride film, such as titanium dioxide, tin dioxide, aluminum oxide, gallium oxide, tin nitride, gallium nitride, aluminum nitride, indium nitride, alloys of metal oxides, alloys of metal nitrides, layers of metal oxides, or layers of metal nitrides, metal oxy-nitrides, metal oxy-nitride alloys, metal nitride alloys (such as AlInGaN alloys), any combination of these materials and/or the like. These materials can be single crystalline, polycrystalline, amorphous, ceramic, polycrystalline, semimetallic, metallic and/or be composed of combinations of these morphologies. For example, the photoelectrocatalytic layer 708 may be composed of an amorphous metal nitride (such as an InGaAlN alloy) amorphous metal oxide, amorphous metal oxynitride and/or other amorphous material or combination of materials. The contact layer 709, which in some embodiments is in direct physical contact with the photoelectrocatalytic layer 708, can include any electrical contact. In some embodiments, the electrical contact layer 709 comprises various conductive metals or polymers patterned as electrodes on the surface of 708, such that one or more regions of the photoelectrocatalytic material 708 are exposed to the analyte 706. In some embodiments, the electrical contact layer 709 may be transparent to the optical excitation energy. For example, indium tin oxide, nickel oxide, nickel oxide gold, or thin (e.g., sub-nanometer or <5000 nm thick) metallic films can be sufficiently transparent to the excitation light 705. In some embodiments, a transparent electrical contact layer 709 may be used in embodiments where the semiconductor optical emitter 703 is below the contact layer 709. The contact layer may also include a "reference electrode" (described below) and/or a "balancing electrode," as described in FIGS. 30 and 31. The support layer 707 may be any solid or reasonably solid material capable of supporting the photoelectrocatalytic layer 708. In some embodiments, the support layer 707 serves as a substrate for the deposition of the photoelectrocatalytic layer 708. Moreover, in some embodiments, a support layer 707 may not be needed or the support layer 707 may be the photoelectrocatalytic layer 708 itself. This substrate may be any solid film of sufficient smoothness to support an effective photoelectrocatalytic layer, such as a metallic substrate, a semiconductor substrate, a glass substrate, a polymer substrate, a plastic substrate and/or the like.

Figure 8:
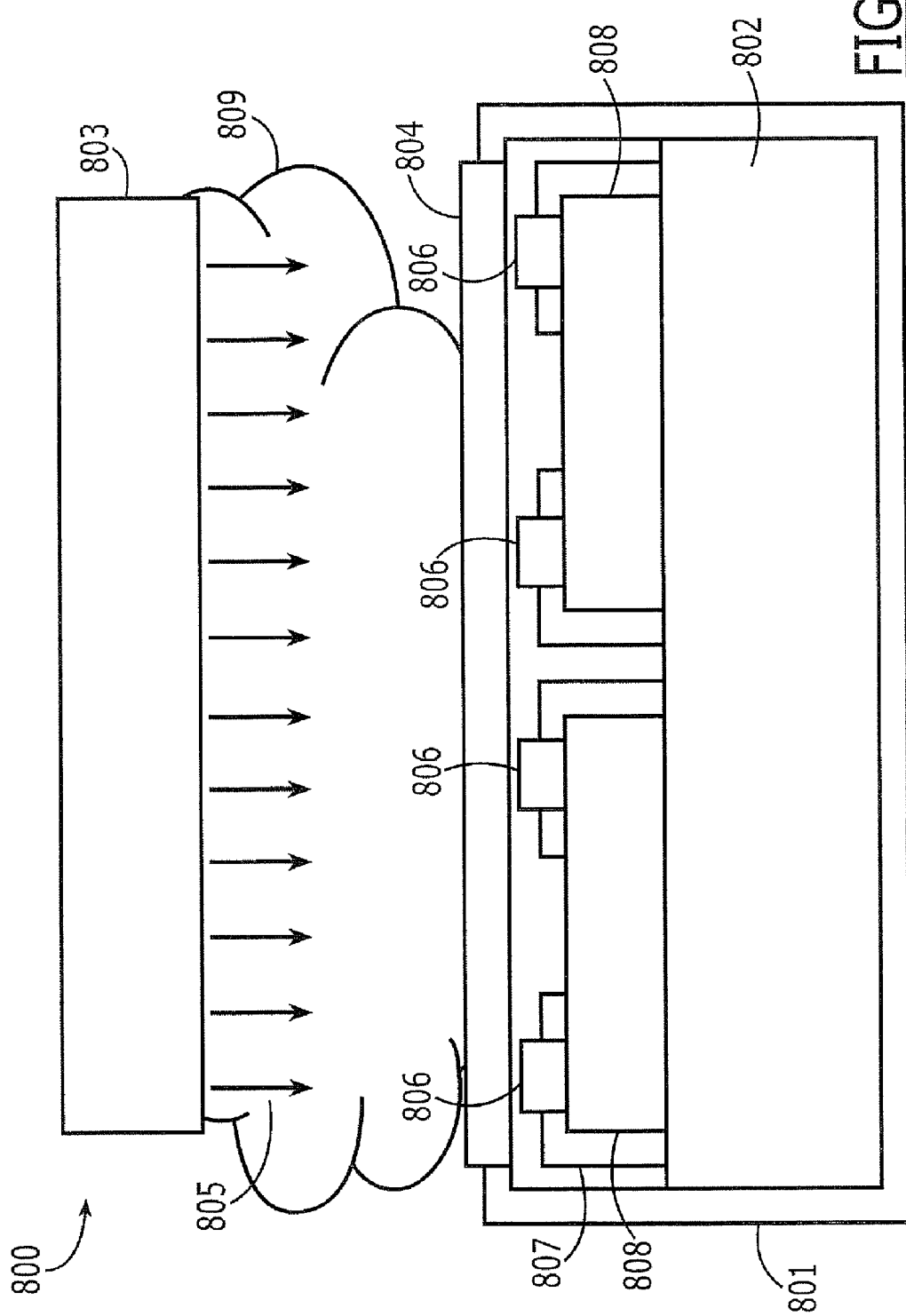
FIG. 8 is a cross-sectional view and FIG. 9 is a top view of a photoelectrocatalytic sensor according to other embodiments of the present invention.

In embodiments shown in FIG. 7, the support layer 707 may be an optically transparent material to allow optical energy 705 to pass through the support layer 707 and be absorbed in the photoelectrocatalytic layer 708. Thus, in these embodiments, the substrate may comprise glass, sapphire, quartz, transparent plastic, a transparent polymer and/ or the like. However, in other embodiments, the semiconductor optical emitter 703 is not located in the package 701 but rather is located outside the package. In these embodiments, the semiconductor optical emitter 703 may be located on the bottom side of the photoelectrocatalytic layer 708 such that optical energy 705 reaches the contact layer 709 first, followed by the photoelectrocatalytic layer 708 and, lastly, the support 707. In such case, a transparent support layer 707 may not be needed. An example of this type of embodiment is shown in FIG. 8, and will be described in detail below. In yet other embodiments, a semiconductor optical emitter 703 is not used, and the photocatalysis is excited via ambient light, such as light from the sun reaching the photoelectrocatalytic layer 707.

The photoelectrocatalytic layer 708 and/or the contact layer 709 may also include selectivity (specificity) layers for preferential transport of the desired analyte 706 towards the photoelectrocatalytic layer 708. For example, layers 708 and/ or 709 may include a membrane for selective transport of certain elements, chemicals, ions and/or particles towards the photoelectrocatalytic layer 708. Typically, these membranes are made of selectively permeable polymers, lipid bilayers, biological ion channels and/or artificial ion channels. In some embodiments, these membranes may include porous, polycrystalline, amorphous, nanostructured, or combinational layers for selective permeability to targeted fluids.

The semiconductor optical emitter 703 can be at least one semiconductor optical source, such as a light-emitting diode (LED) and/or laser diode (LD). Note that specialized semiconductor LDs and LEDs such as organic semiconductor light-emitting diodes (OLEDs), resonant cavity LEDs (RCLEDs), edge-emitting LEDs (EELEDs), and the like can also serve as a suitable semiconductor optical source 703. In other embodiments, a microplasma ultraviolet source that is manufactured using semiconductor fabrication techniques, may also be used. Thus, as used herein, a semiconductor optical source can include any microelectronic optical source. In other embodiments, a non-semiconductor optical emitter, such as a laser, lamp, the sun and/or another natural optical source, may be used.

In some embodiments, the semiconductor light emitting source is a compact point-source capable of being packaged together with other components in an integrated package 701. In other embodiments, the semiconductor light emitting source may be an LED or LD integrated into a monolithic package 701 with the photoelectrocatalytic layer 708 and associated layers 704, 707, and 709. A guiding layer 704 may be in contact with the semiconductor optical emitter 703 for the purposes of guiding optical energy 705 towards the photoelectrocatalytic layer 708. The guiding layer 704 may be any solid or reasonably solid film capable of guiding, filtering, or directing light. In some embodiments, the guiding layer 704 has a higher refractive index than air. In other embodiments, the guiding layer includes an optical lens, mirror, optical waveguide, fiber optic cable, an optical filter, combinations of these and/or the like.

Since it may be desirable for the guiding layer 704 to be at least partially transparent to the excitation light 705, quartz, sapphire, metal nitrides, or fluoropolymers, or other UV-transparent materials may be used for guiding UV light. For the case of photo-excitation using an IR-light source, this material may comprise zinc selenide, amorphous materials transmitting IR, or other IR-transparent media. Standard glass and topaz may be used for guiding visible light, but UV-transparent materials may also be effective for guiding visible light. Because an LED source may image the geometry of the optically emitting LED surface onto a receiving surface, it may be desirable to diffuse the LED beam pattern in order to uniformly distribute the light over the photoelectrocatalytic layer 708. In such embodiments, the guiding layer 704 may be intentionally roughened to scatter light 705 for a more uniform optical excitation of the photoelectrocatalytic layer 708. A variety of guiding layer structures also can be implemented for diffusing light without roughening the surface. For example, intentional defects added to the guiding layer, such as various dopants and/or crystalline defects, can scatter light. A variety of scattering surfaces and structures for diffusive guiding layers are well known to those skilled in the art. In other embodiments, the guiding layer can be composed of one or more layers for collecting light, guiding light, scattering light and/or diffusing light. In some embodiments, the guiding layer 704 may not be used, and the layer 704 can be absent from the structure. As described earlier, the semiconductor optical emitter 703 may be on either side of the photoelectrocatalytic film 708, but FIG. 7 shows the optical emitter 703 directing optical energy 705 towards the support layer 707 first, followed by the photoelectrocatalytic layer 708.

The electronics (controller) 702 may be any combination of electrical components that can be used for powering, controlling, amplifying, signal conditioning, and/or regulating the semiconductor optical emitter 703 and/or the photoelectrocatalytic electrodes of the contact layer 709. In some embodiments, the electrical components include a power source (in some embodiments a battery), a modulating source, a power regulator, a signal processor, an analog-to-digital converter, a signal amplifier and/or the like, all together within the integrated package 701. Electrical circuits supporting a sensor are well known to those skilled in the art, and need not be described in detail herein.

The analyte 706 may be any fluid (as defined previously), but in some embodiments is a gas or particle, or any combination of gases or particles, capable of interacting with the photoelectrocatalytic layer 708, the contact layer 709, or a combination of these layers. In some embodiments, the analyte 706 comprises ionizable gases and vapors, such as oxygen, carbon dioxide, nitrogen, carbon monoxide, ozone, humidity, volatile organic chemicals, aromatics, pollutants, polycyclic aromatic hydrocarbons (PAHs) and/or the like. The analyte 706 can also include various other chemicals and particles including airborne pollutants, biological particles (such as allergens, fungi, bacteria, viruses, organic material, etc.), hydrocarbons, soot particles and/or the like. In some embodiments, the photoelectrocatalytic sensor system 700 is employed as a respiration monitor, for detecting, qualifying, and/or quantifying gases, vapors and/or particles in the breath.

The signal processor 711 may be used to process or pre-process raw or preprocessed signals from the photoelectrocatalytic element(s). This processed information may then be sent to a signal transmitter 712 for the transmission of processed data to a signal analyzer 713. In some embodiments, the signal transmitter transmits data wirelessly to one or more signal analyzers 713. Signal processors and signal transmitters are well known by those skilled in the art, and various types of signal processing electronics and electrical transmission electronics can include commercial off-the-shelf parts. The signal analyzer 713 may be any device capable of computing, such as a laptop computer, a personal digital assistant (PDA), a desktop computer, a cell phone, a smartphone, a calculator and/or the like. In some embodiments, the signal processor 711 and the signal transmitter 712 are all integrated in the package 701. In other embodiments, the signal analyzer 713 is also integrated in the package 701.

Some embodiments may also include an external monitor 710. The external monitor 710 may be any monitor capable of analyzing photoelectrocatalytic related activity in and/or about the photoelectrocatalytic layer 708, the contact layer 709 or the combination of these layers. In some embodiments, the external monitor 710 measures electromagnetic, mechanical, acoustic and/or thermal energy at the surface, and/or other changes at the surface of the photoelectrocatalytic layer 708. In some embodiments, the external monitor 710 may eliminate the need for the contact layer 709 and/or eliminate the need for electrical connections or wires to the contact layer 709. For example, this can be achieved by inductive or optical coupling to the contact layer 709 or photoelectrocatalytic layer 708. In some embodiments, the external monitor 710 is not included in the photoelectrocatalytic sensor 700 at all. In some embodiments, the role of the external monitor can be replaced with an internal monitor 714, housed inside the package 701, as will be described below.

Some embodiments of the invention can provide the photoelectrocatalytic sensor itself, which may be represented by the package 701, and at least some elements therein. The elements outside this package may also be added in some embodiments to provide additional functionality and/or performance. The package 701 may be as simple as a standard TO-5 package or substantially more intricate, such as a stainless steel vacuum package. The packaging materials may include virtually any solid, reasonably inert material, such as metal, plastic, rubber, ceramic and/or the like.

Figure 9:
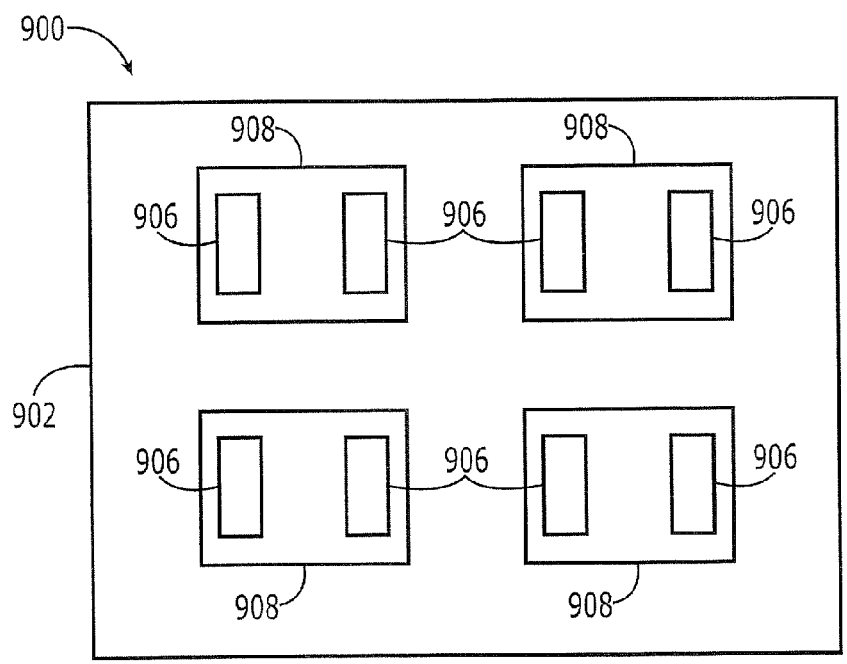

The photoelectrocatalytic layer 708, the support layer 707, and the contact layer 709 may form the photoelectrocatalytic element in some embodiments. In other embodiments, the photoelectrocatalytic element may consist of the photoelectrocatalytic layer 708 and, in other embodiments, the photoelectrocatalytic element may comprise one or more other structure(s) in addition to the photoelectrocatalytic layer 708. The photoelectrocatalytic element may also be referred to herein as a "photoelectrocatalytic electrode" or simply as an "electrode." These electrodes can be one or more photoelectrocatalytic electrodes composed of one or more photoelectrocatalytic films. For example, these electrodes can be arrayed as illustrated in FIG. 9, as described in more detail below.

Other embodiments of a photoelectrocatalytic sensor 800 are shown in FIG. 8. In these embodiments, the semiconductor optical emitter 803 is at least one LED or LD, and it is positioned outside of the sensor package 801. The semiconductor light emitting source 803 shines light 805 onto an array of photoelectrocatalytic films 808 to facilitate photocatalysis of one or more analytes 809 at and/or near the array of photoelectrocatalytic films. The patterned metal contacts 806 are combined with the photoelectrocatalytic films 808 to form photoelectrocatalytic electrode arrays.

It should be noted that the photoelectrocatalytic films 808 and contacts 806 need not be the same for each element of the array. Specifically, multiple photoelectrocatalytic films 808 and/or metal contacts 806 can be used to distinguish between multiple fluid analytes in mixtures of gases, vapors and/or particles. Certain analytes can be qualified and quantified more accurately when compared with a reference analyte of a known concentration, so that multiple photoelectrocatalytic films 808 and metal contacts 806 may be provided. Further, the unique absorption/desorption kinetics and photoelectrocatalytic response of each analyte 809 with respect to each photoelectrocatalytic layer 808, though sometimes subtle, can be used to differentiate between individual analytes in a mixture of analytes, in some embodiments.

A selective membrane 804 may be used in some embodiments to reduce or prevent at least some unwanted matter or energy from approaching the photoelectrocatalytic electrodes while selectively passing one or more analytes. This layer may not be used in some embodiments because the photoelectrocatalytic films 808 may be chosen to be preferentially sensitive to one type of analyte and/or for other reasons. A protective layer 807 may be used to protect parts of the metal contacts 806 and/or photoelectrocatalytic films 808. The protective layer 807 can reduce or prevent unwanted reactions near the metal/photoelectrocatalytic film interface and may also serve as electrical and/or electrochemical passivation. A solid substrate 802 serves as a support layer.

The photoelectrocatalytic layers 808 and contacts 806 can be made of the materials described previously for 708 and 709. In some embodiments, the photoelectrocatalytic films 808 are thin metal oxide films and the contacts are metals and/or electrically conducting polymers. Although for simplicity only two photoelectrocatalytic electrodes are shown in FIG. 8, it is to be understood that any number of photoelectrocatalytic layers and/or contacts can be used to facilitate selectivity in measuring various analytes and/or for other purposes. In some embodiments, the selective membranes 804 can comprise polymers, dielectrics, ion-selective electrode materials and/or particle size filters. These materials are commercially available and well known to those skilled in the art. The protective layer 807 may comprise an insulating dielectric film such as $SiO_2$, SiN, polymers, tape and/or the like. Although layer 807 is shown to partially cover the contact layers 806 in FIG. 8, the protective layer 807 may cover any area, or the entire area, of the contact layers 806 and/or photoelectrocatalytic layers 808. The package 801 itself may be compatible with TO-5, Bergquist and/or similar standardized packaging arrangements.

A top-view of the photoelectrocatalytic sensor 800 is shown as 900 in FIG. 9. Only the photoelectrocatalytic films 908, the contact layers 906, and the support layer 902 are shown for simplicity. Note that exemplary rectangular geometries are drawn for the photocatalytic electrodes, but other shapes, such as circles, squares, triangles and/or other shapes may be used in other embodiments. Moreover, although contact layers 906 are shown on top of the photoelectrocatalytic films 908, these contacts can be placed at the edges, the center, the corners and/or virtually anywhere along the photoelectrocatalytic film surface in other embodiments. Enough space should be left between the contacts to allow detection of absorbed analytes near the surface of the photoelectrocatalytic films 908. Also, although only two contacts per photocatalytic film are shown, three or more contacts may also be employed in other embodiments.

Figure 10:
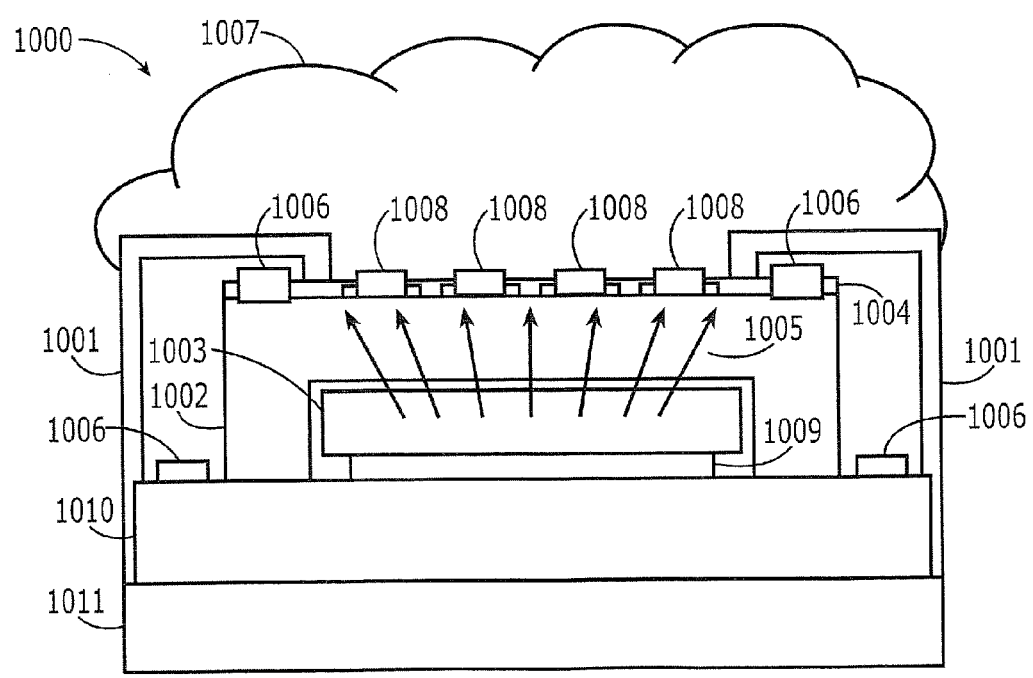
FIG. 10 is a cross-sectional view of a photoelectrocatalytic sensor according to still other embodiments of the present invention.

Embodiments of a photoelectrocatalytic sensor 1000 integrated with at least one underlying LED or LD are shown (in side-view) in FIG. 10. The semiconductor light emitting source 1003 generates optical energy 1005 directed towards one or more photoelectrocatalytic elements 1008 in an array. In FIG. 10, the photocatalytic elements 1008 include both the photoelectrocatalytic films and their respective electrical contacts. The signal from each photoelectrocatalytic element 1008 is read through multiple contact pins 1006 at the edge of the device. These contact pins make contact with circuitry 1004 for individual communication with each photoelectrocatalytic electrode. A submount layer 1009 is used to support heat extraction in the optical emitter 1003 and/or for physical support. The submount layer 1009 may also include metal contacts for delivering electrical power to the LED or LD. The submount layer 1009 may be connected with a secondary mounting layer 1010 for additional thermal extraction, mechanical support and/or electrical power. Electronics 1011 may be integrated within the sensor 1000. The entire monolithic photoelectrocatalytic sensor may be enclosed in a package 1001. The analyte 1007 is shown in direct contact with the photoelectrocatalytic electrodes, without a clearly distinguished selective transport layer 804 protecting the films. Although such a film can be incorporated as in FIG. 8 or selectively deposited on each photoelectrocatalytic electrode 1008, this film may not be incorporated for selective sensing of various analytes in other embodiments.

In FIG. 10, the materials that may be used may be the same as FIG. 8 and FIG. 9. However, it should be noted that the submount layer 1009 and secondary mounting layer 1010 may be used in embodiments of FIG. 10, as the semiconductor optical source 1003 is part of the monolithic photoelectrocatalytic array 1000. These layers, in some embodiments, can be interchangeable or, in some cases, the submount 1009 need not be used. For example, the bond pad metallization of a flip-chip LED 1003 can be lined up with metallization patterned directly on a Bergquist thermal package—including a circuit layer, dielectric material, and metallic base material—such that a submount layer need not be used. In many cases, the submount 1009 and secondary mounting 1010 can be integrated into one unit to reduce the thermal resistance between the two layers. The electronics 1011 may include powering, amplifying, signal conditioning, signal transmitting, signal processing and/or similar electronics. These electronics may be located near the bottom of the sensor 1000, as shown in FIG. 8, but other locations may be used. In some embodiments, the electronics are not included in the sensor 1000 but rather are bifurcated from the sensor altogether. Moreover, as with all the embodiments herein, multiple optical sources 1009 may be integrated into the sensor 1000. In some embodiments, these optical sources may be specifically aligned to one or more PEC electrode(s) 1008. In some embodiments, at least one of these optical sources may generate a different optical wavelength than another optical source.

As was described above, other embodiments of the invention provide methods of monitoring fluids using a photoelectrocatalytic sensor. These fluids may comprise gases and vapors from exhaled breath, airborne and waterborne contaminants and/or industrial pollution. Monitoring fluids from each case may involve different sensor designs. For example, a respiration monitor may be mounted on a portable headpiece or a mouthpiece. In some embodiments, a standardized portable phone headset—including a headpiece, an earpiece, and mouthpiece—incorporates one or more photoelectrocatalytic sensors in the mouthpiece. Such a sensor can facilitate oximetry, capnometry and/or health diagnoses. In some embodiments, the PEC sensors can be mounted in a headpiece, headset, cellular phone, PDA, earpiece, or the like without the need for a mouthpiece.

A photoelectrocatalytic sensor used as an environmental monitor may be located virtually anywhere. For example, an industrial pollution monitor may be located at or near one or more exhaust ports. In some cases, pollution may come from a motor vehicle, in which case a photoelectrocatalytic sensor may be at or near the exhaust of the vehicle. In some embodiments, the sensor may be mounted on a wall, on a tripod, or within another piece of equipment such as a fire alarm, gas alarm, or other unit. For example, sensor modules may be placed throughout a building Heating, Ventilating, Air-Conditioning (HVAC) system in order to pinpoint air contamination and/or more efficiently direct exhaust. In some embodiments, a portable environmental monitor comprising a photoelectrocatalytic sensor can be incorporated in a portable wireless instrument such as an earpiece, headset, cell phone, PDA and/or the like. Because photoelectrocatalytic sensors need not use a heater filament to initiate the catalytic reaction, these sensors can work well for wearable, human-portable sensors as well as explosion-proof sensors.

It should be noted that the photoelectrocatalytic layers 708 do not need to be layers that respond only to UV light to initiate photocatalysis. For example, indium oxynitride can have a band gap ranging from the mid-IR to deep-UV. Thus, employing a photoelectrocatalytic layer of indium oxynitride in a photoelectrocatalytic sensor can facilitate photocatalysis via IR or visible light as well as UV light, depending on the stoichiometry of the indium oxynitride alloy. Thus, an integrated photoelectrocatalytic sensor of indium oxynitride can incorporate an LED in the visible or IR wavelengths as well as the UV. Moreover, nuclear radiation or X-rays can also be used to ionize the surface of a photoelectrocatalytic sensor in some embodiments.

It should also be noted that desired properties of the photoelectrocatalytic layers according to other embodiments of the invention can be realized by nanoengineering the surface layers and/or bulk layers. For example, adding nanoscale features can improve the sensitivity of the photoelectrocatalytic film to gaseous species. Furthermore, nanoengineering the surface and/or bulk layers with regular or irregular nanoscale features can improve the sensitivity to specific analytes and thus can provide a selective, or reasonably selective, gas sensing layer that can be specific to one particular species or class of species. Additionally, the nanostructure of the surface of the photoelectrocatalytic film can affect the wavelengths used for photocatalysis. For example, through the quantum-size-effect, the effective band gap of the surface can be increased or decreased by decreasing or increasing (respectively) the size of nanoscale features in the photoelectrocatalytic film. A variety of nanoscale features can be applied, such as nanorods, nanowires, nanospheres, nanocubes, nanodots, nanowhiskers, nanocoils, nanoribbons, nanodoughnuts, nanopyramids, nanodomes, nanotemples, nanosteps, nanospirals, nanogratings, nanotrenches, nanocapacitors, nanodisks, nanohexagons, nanopentagons, buckyballs, nanodrops, nanoporous films, nanocubes, disordered nanostructures, nanoballons, and the like. This includes nanoscale removal of material, such as in the case of making the material porous via photon-assisted etching techniques.

In other embodiments, explicit nanoengineering need not be used to form practical nanostructures in metal oxide films. For example, in many cases these nanostructures can form naturally via spontaneous ordering during the thermodynamics of film growth or film deposition. In other cases, nanostructured features may be directly engineered through photolithographic techniques, block copolymer techniques, selective deposition techniques, thermodynamic methods and/or the like.

Other embodiments of the invention can provide analyte monitors capable of identifying and quantifying multiple species in real time. Some embodiments can combine solid state optical emitters with photoelectrocatalytic electrodes, enabling a low-cost, low-power, low-profile, portable/wearable and/or real-time analyte monitor. In some embodiments, the analyte monitor can operate as a personal environmental assessment monitor for monitoring exposure to VOCs, PAHs, ozone, and/or other airborne pollutants and/or toxins. Some embodiments can provide a portable monitor for volatile organic compounds.

VOC sensors according to some embodiments of the invention can operate by monitoring the electrochemical response to the known photocatalytic effect of titania, zirconia, and various other metal oxides in the presence of different gases and vapors. In some embodiments, ultraviolet light generates electron-hole pairs (and quasi Fermi levels) in the metal oxide film, and these electrons/holes are consumed to catalyze airborne species at the metal oxide surface.

Figure 11:
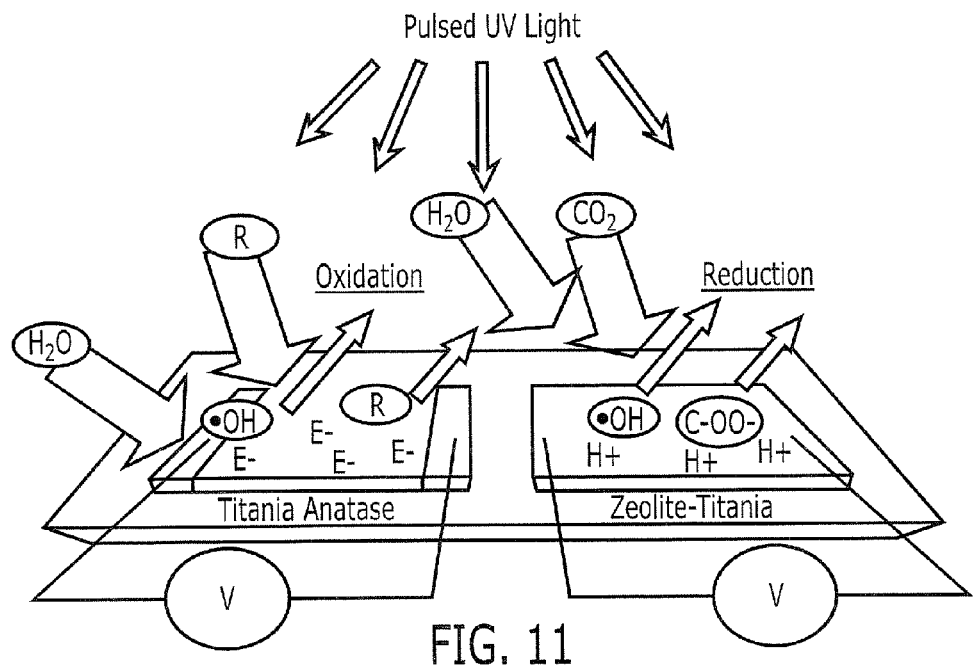
FIG. 11 conceptually illustrates photoelectrocatalytic sensing devices and methods according to other embodiments of the present embodiment.

Conventionally, the photocatalytic effect of titania has been applied towards the biological sterilization of air and water. In photoelectrocatalytic sensing according to some embodiments of the invention, the photocatalyzed byproducts of gas and vapor oxidation are not simply discarded but rather are monitored electrically between two or more conductive contacts as illustrated schematically by the voltmeters in FIG. 11. This can provide a convenient tool for monitoring the presence and/or relative intensity of adsorbed gases and vapors. Depending on the stoichiometry, porosity, morphology and/or type of the metal oxide film, different gases can be selectively adsorbed and detected. Metal nitrides, metal arsenides, and other semiconductor materials can also make excellent photocatalysts. Moreover, when metal oxides are referenced, it should be understood that other solid-state photocatalysts can also be used in other embodiments of the invention. In some embodiments of the invention, analyte selectivity may be achieved by monitoring the transient electrical response that is unique to each ionized species. In other embodiments, analyte selectivity may be achieved by monitoring and comparing the electrical response from multiple electrodes having preferentially selective catalysts, as illustrated in FIG. 11. Other techniques for achieving analyte selectivity will be described in detail below.

For example, as shown in FIG. 11, under the UV excitation of titania in a humid ambient, photogenerated holes convert adsorbed water vapor into H+ and hydroxyl radicals (.OH) that can oxidize volatile organic compounds ("R" in FIG. 11) at the titania surface. Similarly, oxygen adsorbed under UV excitation generates superoxide anions which also oxidize VOCs. If the photoelectrocatalytic metal oxide film is fabricated as an electrode, the electrical response to adsorbed, photocatalyzed analyte can be directly related to the analyte concentration.

Photocatalytic sensing according to various embodiments of the present invention may be sharply contrasted with conventional thermocatalytic sensing, particularly in the context of VOC monitoring via metal oxide sensors. In photoelectrocatalytic sensing, photogenerated electron-hole pairs are primarily responsible for VOC catalysis, such that certain species can be chemically reduced (by the transfer of electrons from the metal oxide) or oxidized (by the transfer of holes from the metal oxide). In contrast, for thermocatalytic sensing, thermal energy is primarily responsible for VOC catalysis. Namely, thermal energy in the metal oxide sensor can raise the Fermi energy such that electrons can be injected into the gaseous species, reducing the vapor at the surface, thus spawning the generation of surface radicals which are then adsorbed at the metal oxide surface. For the case of VOCs on thermally heated $SnO_2$, these adsorbed radicals behave as donors, providing free carriers for electrical conduction.

Characteristic of both thermocatalysis and photocatalysis, the conductivity response from adsorbed radicals can be relatively slow, and may take several seconds for equilibration. However, for the case of photocatalysis there can be an additional conductivity response associated with the generation of electron-hole pairs. Normally, photogenerated electron-hole pairs recombine within nanoseconds of optical excitation. However, as photogenerated holes are preferentially consumed during the photocatalysis of oxidizable VOCs, an accumulation of negative charge can build up at the metal oxide surface as will be described below in connection with FIG. 14. This negative charge accumulation can be monitored both conductively (as photocurrent) and capacitively. Moreover, if the UV photo-excitation is modulated on and off, these free electrons will accumulate and recombine accordingly such that the time-dependent concentration of these unpaired electrons can be distinguished from noise and clutter. Because this surface charge response can be several times faster than the adsorbed radical charge response, these two independent PEC responses can be distinguished in the same circuit or in different circuits, which can provide selective differentiation between various VOCs via a single sensor according to some embodiments of the invention. Furthermore, the sensitivity of the PEC response can be controlled independently of temperature by controlling the wavelength and/or intensity of photo-excitation. Additionally, because PEC analyte sensitivity need not use elevated temperatures, where solid-state devices experience elevated electrical noise, the signal-to-noise ratio of PEC sensors can be much greater than that of thermocatalytic sensors.

Additionally, monitoring the time-dependent PEC response of a single catalyst can also provide enhanced discrimination between VOCs. This temporal response may be limited primarily by the recombination rate of excess carriers (holes or electrons) at the metal oxide surface and/or the adsorption/desorption rate of the gaseous species within the metal oxide film. The latter can be controlled to some degree by the thickness and/or morphology of the film. By monitoring signal rise-time in a single PEC sensor, outstanding discrimination between various VOCs can be realized through principle component analysis.

Other techniques for achieving VOC specificity can implement an array of multiple catalytic layers having selective (or, in some embodiments, quasi-selective) photoelectrocatalytic properties. Various catalysts can be characterized by unique surface interaction properties and specific chemical potentials (Fermi energies). In particular, the application of gallium, indium and/or zinc oxide photocatalysts in PEC sensing can provide a stable, robust PEC surface for the selective photocatalysis of various gases, in some embodiments of the invention.

Indeed, photoelectrocatalytic sensing according to some embodiments of the invention may provide a promising solution for reducing or eliminating the need for thermal catalysis. However, because most metal oxide films are characterized by high band gaps in the UV range, photoelectrocatalytic sensing may exchange the problem of high temperatures for the challenge of a low-cost, compact, ultraviolet source. Fortunately, compact commercially available UV LEDs are now widely available and can be integrated with aforementioned metal oxide electrodes, providing a packaged PEC VOC sensor.

Figure 13A:
FIG. 13A is a photograph of an experimental apparatus that may be used to demonstrate photoelectrocatalytic sensing using a UV LED according to various embodiments of the present invention.
Figure 13B:
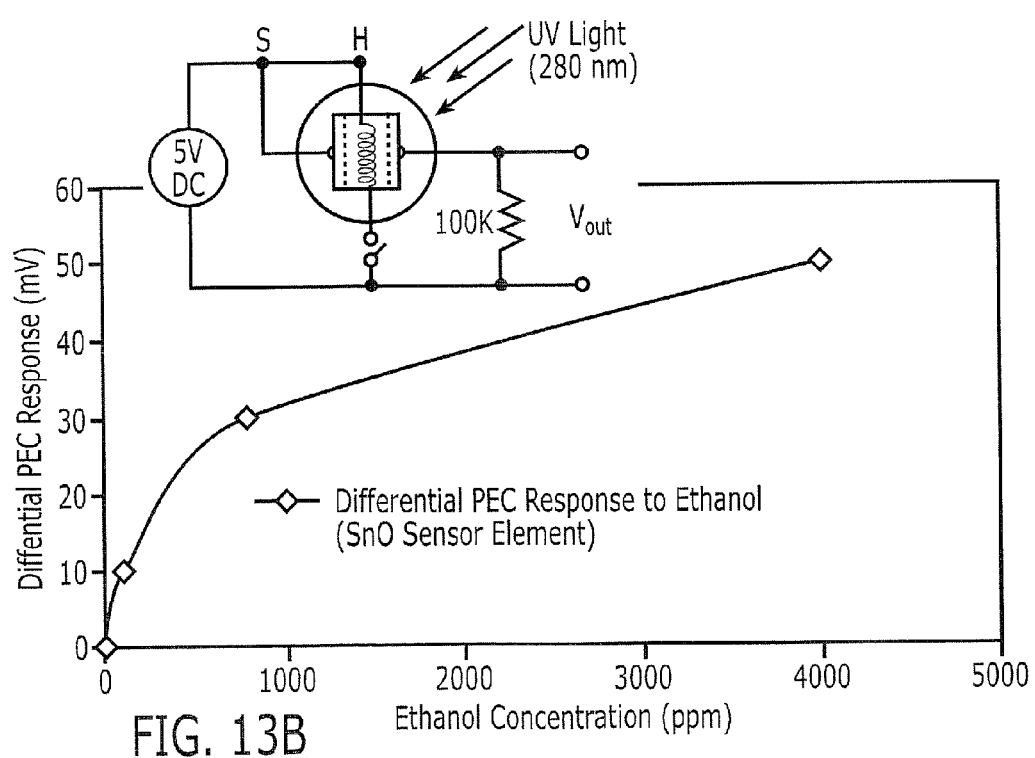
FIG. 13B is a circuit diagram of the experimental apparatus of FIG. 13A, and graphically illustrates differential photoelectrocatalytic responses as a function of ethanol concentration that was observed.

Sensing using the photoelectrocatalytic effect according to some embodiments of the present invention has been demonstrated using a modified commercially available thermocatalytic tin oxide VOC sensor. This configuration was used solely for ease of experimentation, and embodiments of the invention are not dependent on the thermocatalytic sensor technology. Thus, the following experimental example is provided for illustrative purposes and shall not be regarded as limiting the invention. As illustrated in FIG. 13A, in this experiment, a 280 nm UV LED was aligned head-on with the filament-heated tin oxide sensor, with the entire setup covered by a large glass beaker. The tin oxide VOC sensor includes a simple tin oxide ceramic sintered onto an alumina cylinder surrounding a heating coil. The heating coil was disconnected in this experiment such that conventional thermocatalysis would not take place. Instead, about 100 µW of 280 nm UV light from a UV LED was focused directly onto the unheated tin oxide sensor, and the photoelectrocatalytic (PEC) conductivity response to varying ethanol concentration was measured using a simple biasing circuit (inset of FIG. 13B) with an oscilloscope used to monitor the electrical response of the sensor. The VOC concentration was calibrated using a second VOC monitor situated inside the glass beaker (not shown in FIG. 13A), operated in thermocatalytic mode.

Ethanol vapor was introduced into the covered setup by placing a small petri dish of liquid ethanol underneath the glass beaker at room temperature. A nonlinear increase in the PEC response with increasing ethanol concentration was observed (FIG. 13B) under steady UV light. This type of logarithmic response is characteristic of catalysis and may be expected for this sensing configuration. In the absence of UV light, the PEC signal decayed to zero, regardless of the ethanol concentration, over the course of a few seconds. Additionally, a differential response was never detected in the absence of UV light. A stronger PEC response could be observed by activating the heater filament at low current such that the tin oxide sensor could reach a temperature slightly higher than room temperature (e.g., 320K). This reduced the baseline conductivity of the tin oxide sensor to more easily measurable values and encouraged desorption of the ethanol from the service between test runs.

To verify that localized optical heating was not responsible for the conductivity response, the UV LED was replaced with a bright (about 10 mW) white LED and a 6 mW red laser pointer, neither of which emit significant UV light. In each case, a PEC response of FIG. 13B was not observed, regardless of the ethanol concentration. This example provides a high level of confidence that a UV-induced photoelectrocatalytic reaction is responsible for the observed ethanol sensing.

Figure 13C:
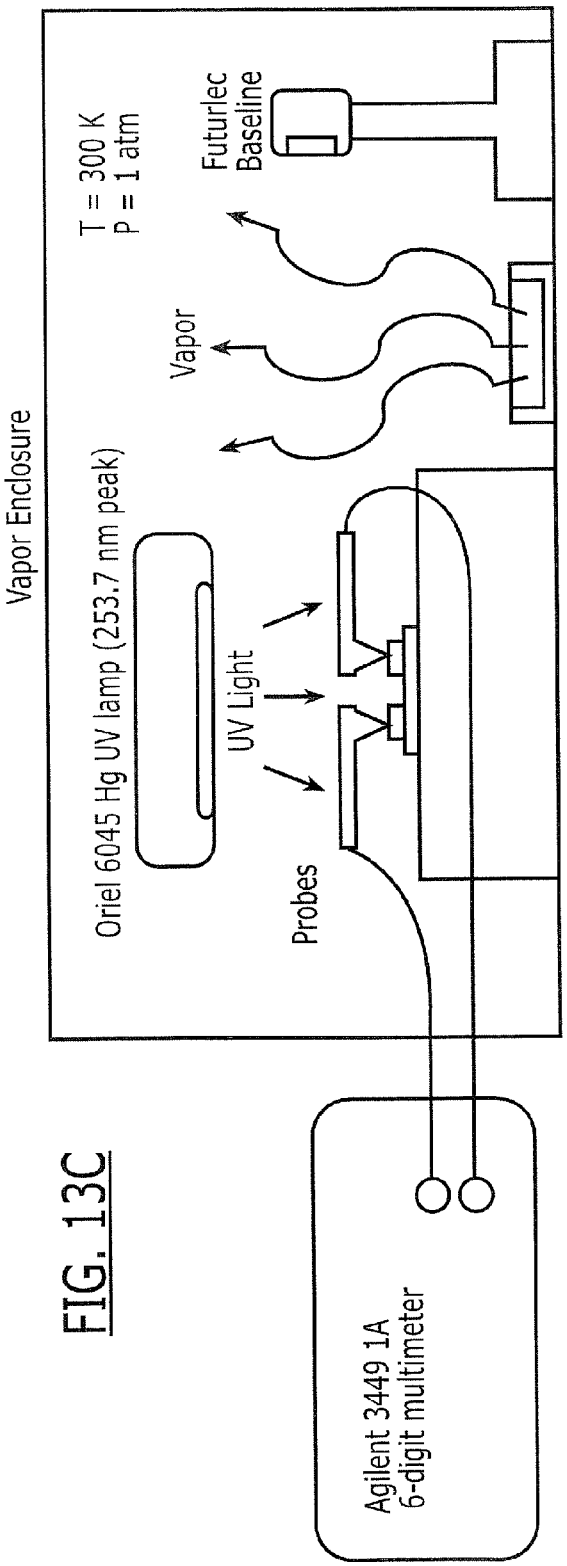
FIG. 13C schematically illustrates another experimental apparatus that may be used to demonstrate photoelectrocatalytic sensing of various volatile organic compounds using an InGaZnO MSM photoelectrocatalytic element according to various embodiments of the present invention.
Figure 13D:
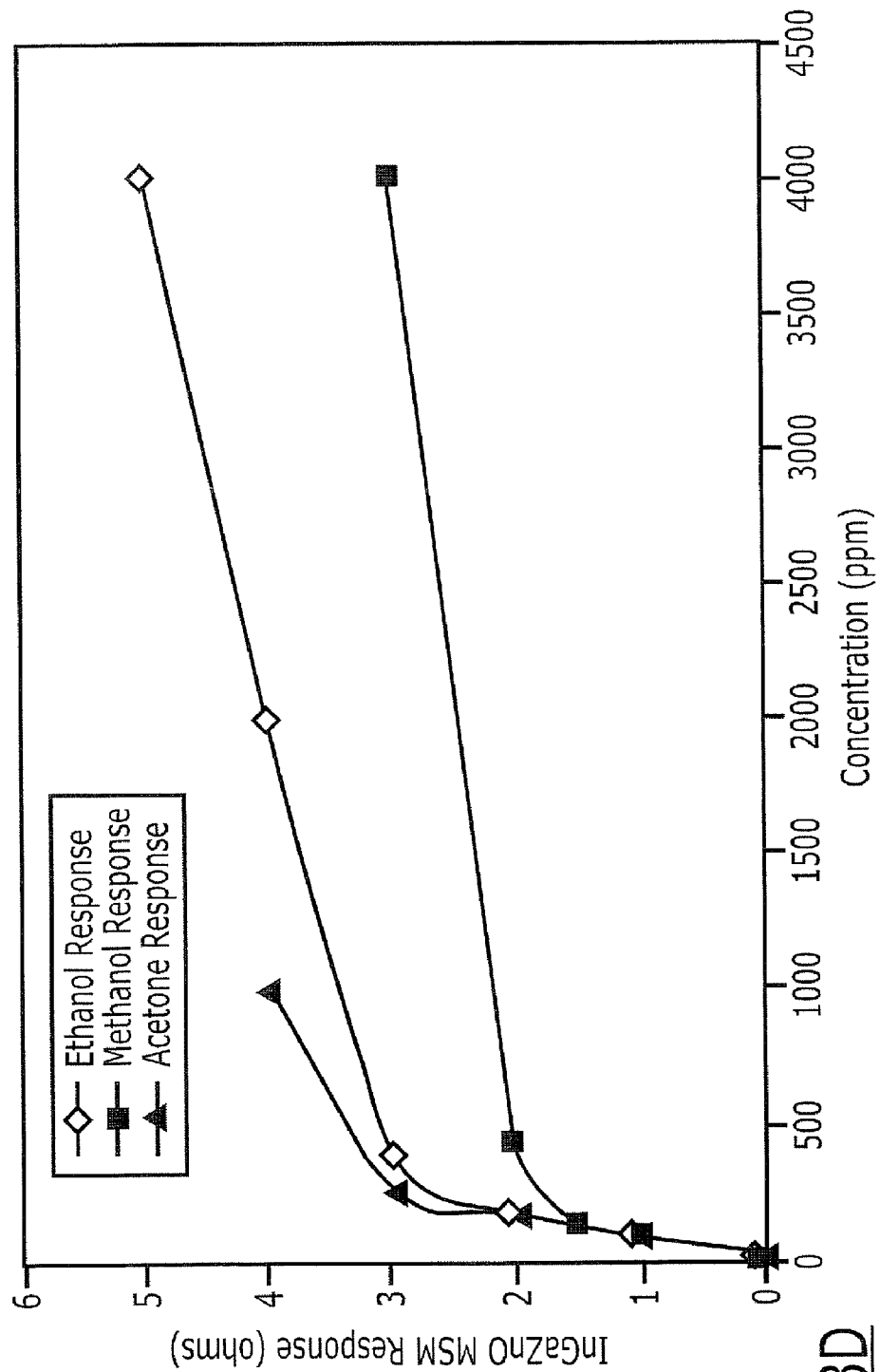
FIG. 13D graphically illustrates response of the photoelectrocatalytic element as a function of concentration of ethanol, methanol and acetone that was observed during the experiment of FIG. 13C.

FIGS. 13C and 13D provide other experimental examples of sensing using the photoelectrocatalytic effect according to some embodiments of the present invention. The following experimental examples also are provided for illustrative purposes, and shall not be regarded as limiting the invention.

As illustrated in FIG. 13C, photoelectrocatalytic testing of ethanol, methanol, acetone and water vapor were performed using the configuration shown. Ozone testing was executed using a 280 nm UV LED excitation source, and ozone was generated using an optically shielded deuterium lamp. Vapor testing was baselined using a tin oxide heated-filament alcohol sensor marketed by Futurlec. The Futurlec sensor is known to respond to various volatile organic vapors with virtually identical sensitivity.

As illustrated in FIG. 13D, under photoelectrocatalytic excitation, the InGaZnO MSM showed a strong sensitivity to acetone and ethanol vapors, and a modest sensitivity to methanol vapor, but no marked sensitivity to water vapor or ozone. In contrast, the ZnO MSM was sensitive to water vapor and ozone, but showed no marked sensitivity to any of the volatile organic vapors. Because the concentration of water vapor and ozone could not be baselined with the Futurlec sensor, only a binary on/off response could be observed.

Without wishing to be bound by any theory of operation, it is theorized that the chemical selectivity of each metal oxide film may be due to the micro- and/or nano-structure of the InGanO in comparison to the ZnO film. The ZnO is mostly polycrystalline, whereas the InGaZnO film is composed of polycrystalline components and amorphous components. Thus, surface adhesion, adsorption/desorption and/or electrochemical properties may be different for each film in the presence of different vapors.

Figure 12:
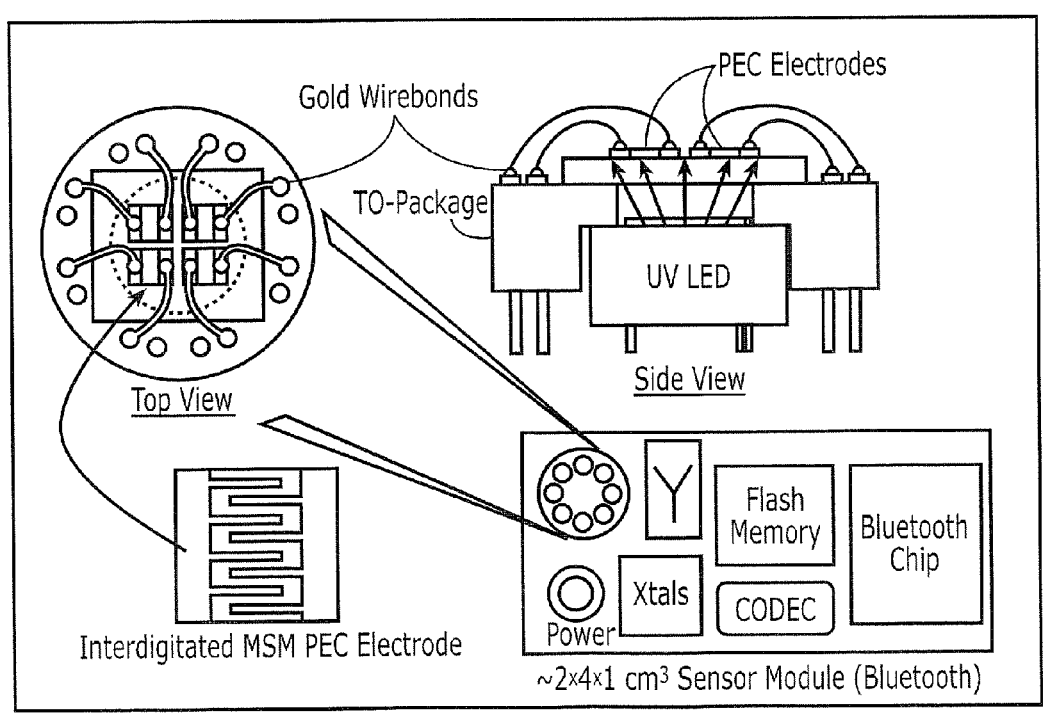
FIG. 12 illustrates photoelectrocatalytic sensors according to still other embodiments of the present invention, as packaged in a wireless communications module for portable analyte monitoring according to various embodiments of the present invention.

FIG. 12 illustrates a PEC VOC monitor according to some embodiments of the invention, integrated into a Bluetooth module. The VOC sensor element includes a UV LED integrated with a PEC electrode array, packaged together in a milled TO-header. The PEC electrodes are connected to the TO-header through, for example, gold wire bonds. The multiple PEC electrodes can enhance the specificity of the VOC monitor. In embodiments of FIG. 12, each PEC electrode is composed of interdigitated electrodes, though a variety of other electrode configurations may be used. The interdigitated configuration can allow conductivity, photocurrent, capacitance, and impedance to be monitored in the same device. The packaged VOC sensor element can be integrated into a compact Bluetooth module for wireless communications. However, a variety of wired or wireless modules other than Bluetooth, such as ZigBee, IEEE 802.11b,g, or the like can be used. Regardless of the protocol used, the compact, portable, low-power module of FIG. 12 can provide wearable VOC monitoring.

Without wishing to be bound by any theory of operation, the fundamental physics and electrochemistry of the PEC effect for semiconductor catalysts, such as metal oxide catalysts, is summarized pictorially in FIGS. 14-16. As will be described below, FIG. 16 describes a method of PEC sensing where sub-band-gap visible or IR radiation triggers PEC sensing, without the need for UV wavelengths and UV optical sources.

Figure 14A:
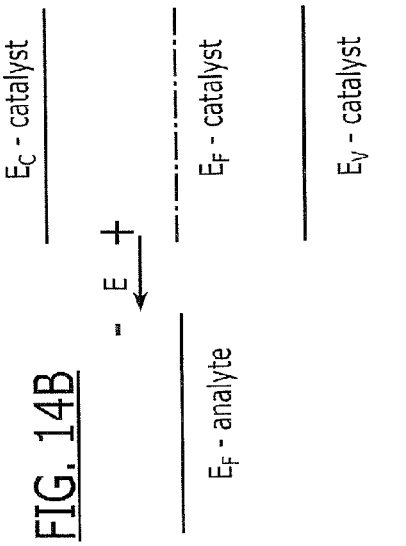
FIGS. 14A-14C graphically illustrate fundamental physics of a photoelectrocatalytic effect, where an analyte is oxidized according to various embodiments of the present invention.
Figure 14B:
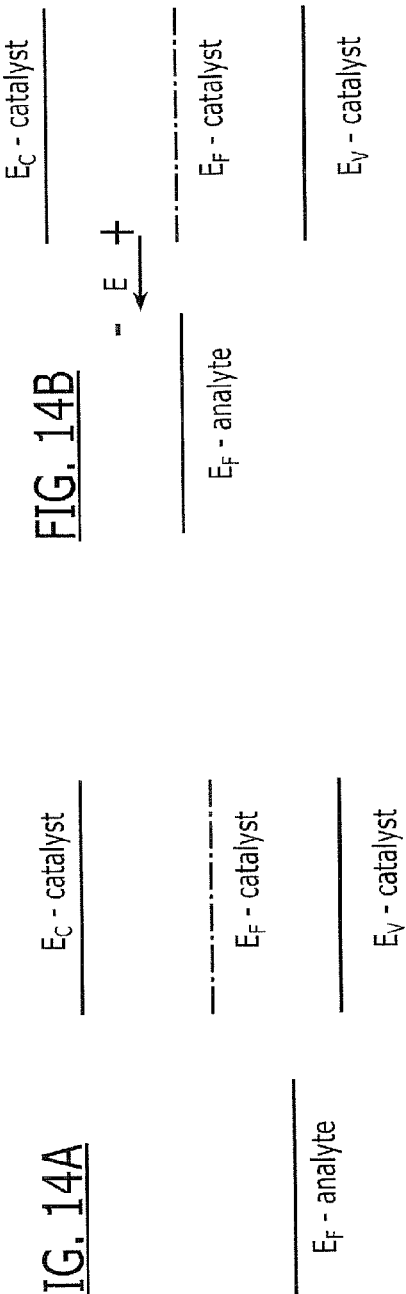
Figure 14C:
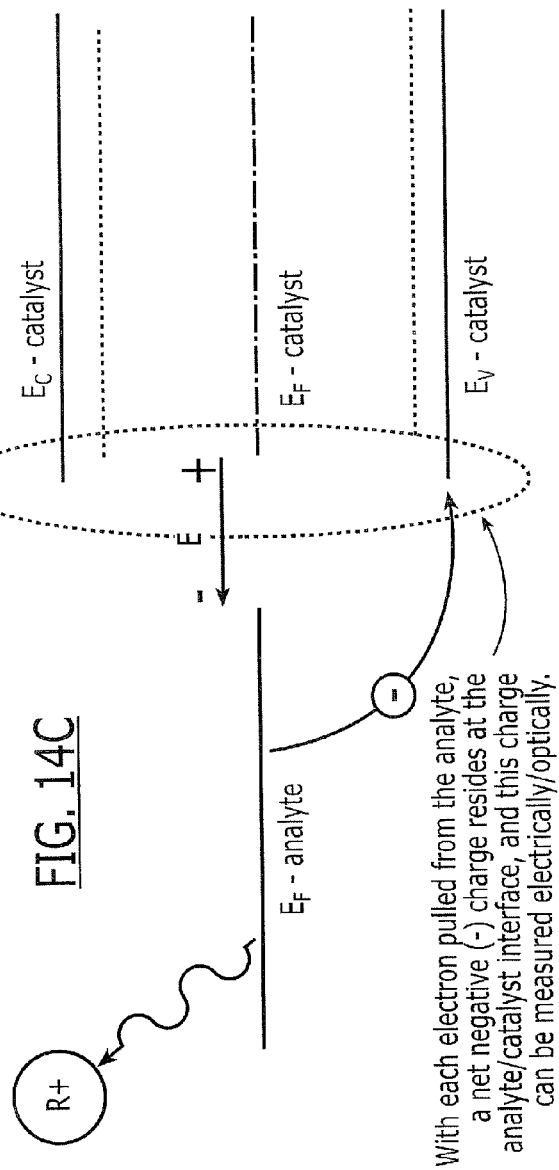

FIGS. 14A-14C illustrate the electrochemistry for the oxidation of an analyte near a solid-state catalyst via the photoelectrocatalytic effect. In this case, the chemical potential (or Fermi potential) of the analyte ($E_F$-analyte) is lower than that of the solid-state catalyst ($E_F$-catalyst) (FIG. 14A). At the analyte-catalyst interface, the establishment of electrochemical equilibrium results in an electric field at the interface, pointing towards the analyte and away from the catalyst (FIG. 14B). At the microscopic level, this field is caused by the redistribution of charge at the analyte-catalyst interface due to a differential in charge affinity for the differing materials. The photo-excitation of the catalyst layer (at photon energies at or above the band gap energy of the catalyst) generates quasi Fermi levels (shown as dotted lines) and electron-hole pairs as shown in FIG. 14C. The electric field at the analyte-catalyst interface ejects holes from the catalyst layer (pulling electrons from the analyte) thereby oxidizing analyte near the surface. As the reactive byproducts leave, a net negative charge resides at the catalyst surface, and this negative charge can be measured electrically via surface electrodes.

The process in FIGS. 15A-15C is somewhat reversed, as the chemical potential of the analyte is higher than that of the catalyst (FIG. 15A). Thus, under chemical equilibrium, the electric field at the interface points away from the analyte and towards the catalyst (FIG. 15B). Under photo-excitation, free electrons are injected into the analyte, reducing the analyte, leaving a net positive charge at the catalyst surface (FIG. 15C). This polarity of the charge response can allow a PEC VOC monitor to differentiate between oxidizable and reducible volatile species at the PEC surface.

FIGS. 16A-16C illustrate sensing reducible analyte species via the PEC effect. In these embodiments, the catalyst is doped with deep-level intentional impurities ($E_{impurity}$), such as rare-earth dopants (erbium, europium, promethium and/or the like) (FIGS. 16A and 16B). Thus, sub-band-gap photo-excitation can trigger the injection of electrons into the analyte, reducing the analyte, and thus providing a net positive charge at the surface for electrical sensing (FIG. 16). In the presence of oxidizable analyte, the net surface charge will be negative. Embodiments of FIGS. 16A-16C can allow oxidizable and reducible analyte species to be monitored with visible or infrared light as opposed to UV light. Because visible and infrared LEDs may be more efficient, reliable, affordable and/or readily available than UV LEDs, these embodiments may be used in some portable VOC sensing applications.

From the physics of operation outlined in FIGS. 14, 15, and 16, one technique for potentially increasing the sensitivity of the PEC effect in conductive detection mode is to run higher than nominal currents through the electrodes to sweep excess charge carriers before carrier recombination. This type of configuration may be used for PEC sensing where current is passed between at least one electrode.

Any of the embodiments described herein may be used for environmental monitoring, such as VOC monitoring, in addition to respiration monitoring. "VOC monitoring" includes monitoring benzene, ethanol, hexane, aromatics, ketones, aldehydes and/or other volatile compounds that can be gaseous at room temperature. In some embodiments, the PEC sensor is employed as an environmental monitor, for detecting, qualifying and/or quantifying gases, vapors, and particles in air—for example, a monitor for VOCs, PAHs, ozone, carbon monoxide, $NO_x$ and/or the like. In some embodiments, this environmental monitor PEC sensor system may be compact, wearable and/or integrated onto a telemetric module, such as a Bluetooth headset module, for monitoring one's personal environment and transmitting this information to a cell phone, personal digital assistant (PDA), computer, database, or the like (FIG. 12).

In some embodiments, an external monitor 710 and/or internal monitor 714 of FIG. 7 can be used to monitor other forms of energy during photocatalysis. For example, a gas or vapor 706 which breaks down into byproducts under photocatalysis from UV light 705 may result in byproducts which absorb, reflect, or fluoresce when exposed to UV light. This can be monitored by a photodiode 714 housed inside the package 701. A specific example of this type of device 2700 is shown in FIG. 27.

Referring to FIG. 27, in these embodiments, the milled TO-header contains a mounting bracket holding two photodiodes on either side of the UV LED. As UV light from the UV LED induces photocatalysis in the PEC electrodes, the byproducts of the vapor analyte fluoresce, and this energy can be used to potentially increase the specificity of the PEC sensor to the analyte species measured. As a particular example, if the liquid or vapor analyte contains molecules of nicotinamide adenine dinucleotide (NAD+), the UV-induced PEC effect can reduce at least some of the NAD+ into NADH, which is a fluophore emitting blue light under UV excitation. In this way, both the electrical response of the PEC effect and the fluorescence response of the PEC byproducts can be measured in the same device, which can provide enhanced specificity for identifying one reducible analyte from another.

Combined PEC+ fluorescence device 2700 of FIG. 27 can be used to allow improved specificity, concentration accuracy and/or sensitivity of measuring volatile analyte species that are themselves both volatile and fluorescent. For example, a variety of plant oils are volatile under UV photo-excitation as well as fluorescent under UV excitation. A combined device according to some embodiments of the invention can be used to allow improved specificity of sensing such species of analyte. Other optical properties of the PEC film 708 under optical excitation 705 in the presence of analyte 706, such as reflection, diffraction, absorption, plasmon interaction, phonon interaction, and the like, can also be monitored during photocatalysis using the external 710 or internal monitor 714, and this can provide further sensor specificity to a particular type of analyte.

For example, the PEC effect can be used in conjunction with surface plasmon resonance (SPR) to monitor analyte at the PEC layer 708. In such embodiments, electromagnetic probing energy, such as optical probing energy, hitting the PEC layer is altered by plasmon generation at the PEC layer 708 in response to the combination of analyte 706 and photo-excitation 705 at the PEC layer 708 surface. The optical probing energy can be altered by a change in reflection, diffraction, transmission, absorption, polarization, wavelength, phase, intensity and/or the like in response to plasmon interactions at the PEC layer 708. SPR plasmon generation is usually generated by laser excitation at a surface, and this may be incompatible with a portable SPR monitor. However, in the PEC/SPR embodiments just described, the plasmons can be generated by an integrated LED, such as that of FIG. 17 or the like, as will be described in detail below. Similarly, the optical probe energy and optical probe energy monitoring can be accomplished with the excitation energy itself and parallel photodiodes, as shown in FIG. 27. In these embodiments, the excitation energy may not only be responsible for exciting the plasmons but also the optical probe energy—the excitation energy is altered by the plasmon/optical interaction, and this altered optical energy may be monitored by the photodiodes. Other types of integrated optical detectors can replace the photodiodes, with polarization detectors, diffraction gratings and/or the like. It should be understood that various secondary detectors (710 or 714) and detector configurations may be used to monitor analyte during PEC sensing, and FIG. 27 is merely one example.

Figure 17:
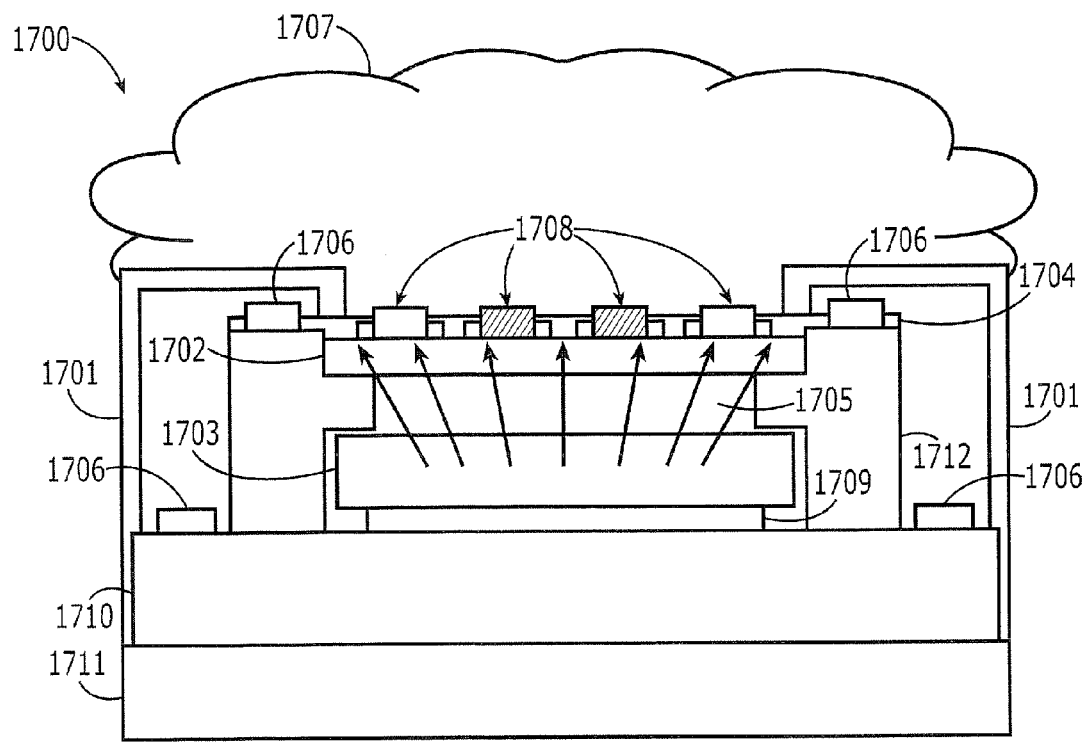
FIG. 17 is a cross-sectional view and FIG. 18 is a top view of a photoelectrocatalytic sensor according to still other embodiments of the present invention.

Other embodiments of a photoelectrocatalytic sensor 1700 integrated with at least one underlying LED or LD, is shown in side-view in FIG. 17. The semiconductor light emitting source 1703 generates optical energy 1705 directed towards one or more photoelectrocatalytic elements 1708 in an array. In FIG. 17, the photocatalytic elements include both the photoelectrocatalytic films and their respective electrical contacts.

It should be noted that the photoelectrocatalytic films and contacts need not be the same for each element of the array. Specifically, multiple photocatalysts and metal contacts can be used for the purpose of distinguishing between multiple fluid analytes in mixtures of gases, vapors and/or particles. Certain analytes can be qualified and quantified more accurately when compared with a reference analyte of a known concentration, so that multiple photoelectrocatalytic films and metal contacts may be provided. Further, the unique absorption/desorption kinetics, surface interaction physics and/or photoelectrocatalytic response of each analyte 1707 with respect to each photoelectrocatalytic electrode 1708, though sometimes subtle, can be used to differentiate between individual analytes in a mixture of analytes. The signal from each photoelectrocatalytic electrode 1708 may be read through multiple contact pins 1706 at the edge of the device. These contact pins make electrical contact with the array circuitry 1704 for individual communication with each photoelectrocatalytic electrode. In some embodiments, the multiple electrical contacts are made through, for example, gold wires bonded between the PEC electrodes 1708 and the contact pins 1706. A submount layer 1709 is used to support heat extraction in the optical emitter 1703 and for physical support. The submount layer 1709 may also include electrically conductive contacts for delivering electrical power to the LED or LD. The submount layer 1709 may be connected with a secondary mounting layer 1710 for additional thermal extraction, mechanical support and/or electrical power. Electronics 1711 may be integrated with the sensor 1700. The entire monolithic photoelectrocatalytic sensor may be enclosed in a package 1701. The analyte 1707 is shown in direct contact with the photoelectrocatalytic elements 1708, without a secondary layer to protect the electrical contacts, such as a dielectric layer, polymer layer, or the like. Although such a protective layer can be incorporated at or near the surface of the PEC electrodes 1708, or selectively deposited on each photoelectrocatalytic electrode, this layer may not be needed for selective sensing of various analytes in many environments.

The photoelectrocatalytic elements 1708, composed primarily of PEC films and metal contacts, can be made of the materials described previously for 708 and 709. In some embodiments, the photoelectrocatalytic films are thin metal oxide films and the metal contacts are metals and/or electrically conducting polymers. Although for simplicity only four photoelectrocatalytic electrodes are shown in FIG. 17, it is to be understood that any number of catalytic films and contacts can be used to facilitate selectivity in measuring various analytes and/or other purposes. For additional selectivity, one or more analyte-selective membranes composed of polymers, dielectrics, ion-selective electrode materials and/or particle size filters can be deposited on one or more of the PEC electrodes. These materials are commercially available and well known to those skilled in the art.

The package 1701 itself may be compatible with TO-header, Bergquist and/or similar standardized packaging arrangements. In some cases, the submount layer 1709 and secondary mounting layer 1710 are used, as the optical source 1703 is part of the monolithic photoelectrocatalytic array 1700. In other embodiments, layers 1709 and 1710 can be interchangeable or, in some cases, the submount 1709 need not be used. For example, the bond pad metallization of a flip-chip LED 1703 can be lined up with metallization patterned directly on a Bergquist thermal package—including a circuit layer, dielectric material, and metallic base material—such that a submount layer may not be used. In many cases, the submount 1709 and secondary mounting 1710 can be integrated into one unit to reduce the thermal resistance between the two layers. The control electronics 1711 may include powering, amplifying, signal conditioning, signal transmitting, signal processing, analog-to-digital conversion, digital-to-analog conversion and/or similar electronics. These control electronics may be located near the bottom of the sensor 1700 (as shown in FIG. 17) but other locations may be used. In some cases, the control electronics are not all included in the sensor 1700 but rather are at least partially bifurcated from the sensor.

Various other embodiments of FIG. 17 also may be provided. For example, in FIG. 17, the PEC electrodes 1708 are shown facing away from the optical excitation 1705. In these embodiments, the PEC films in the PEC electrodes may be sufficiently thick to absorb sufficient optical energy, but not so thick as to absorb all of the photons close to the PEC surface facing the optical emitter 1703. If the PEC layer is too thick, it may be difficult for free charge to reach the PEC surface closest to the analyte 1707. Embodiments that can reduce or avoid this effect can invert the PEC electrode array 1708 shown in FIG. 17 such that the PEC electrodes face the semiconductor light emitting source. A pathway may be provided for the analyte between the PEC electrode array 1708 and the semiconductor light emitting source 1703. This pathway can be achieved by simply cutting a hole in the support layer 1712 and/or creating a gap. In these embodiments, an additional protective optically transparent layer, such as a quartz window, may need to be mounted between the semiconductor light emitting source 1703 and the PEC electrode array 1708 to hermetically protect the semiconductor light emitting source.

Figure 18:
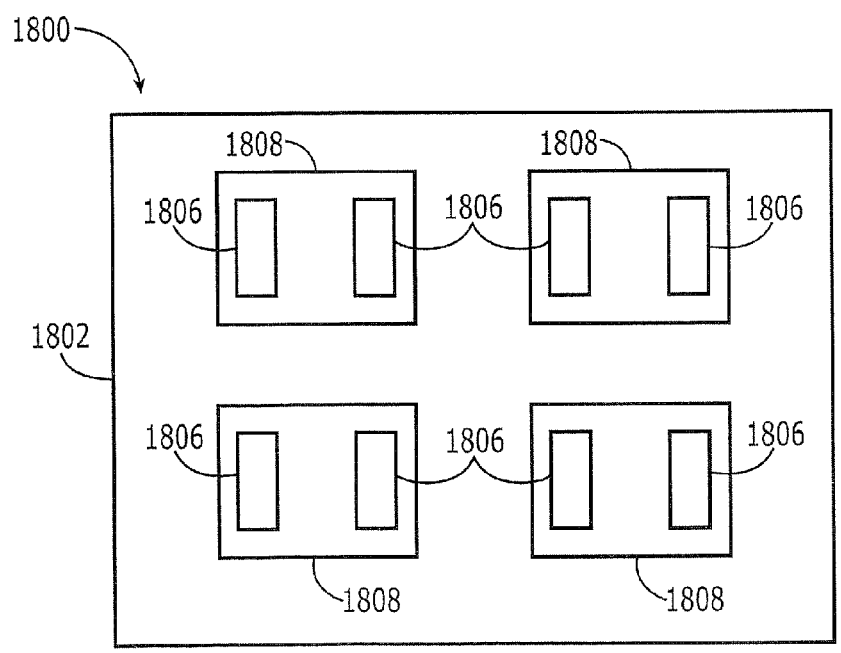

A partial top-view of a photoelectrocatalytic sensor 1700 is shown as 1800 in FIG. 18. Only the photoelectrocatalytic films 1808, the contact layers 1806, and the support layer 1802 are shown for clarity. Note that exemplary rectangular geometries are drawn for the photocatalytic electrodes, but other shapes, such as circles, squares, triangles and/or other shapes are also suitable. Moreover, although the contact layers 1806 are shown on top of the photoelectrocatalytic films 1808, these contacts can be placed at the edges, the center, the corners and/or virtually anywhere along the photoelectrocatalytic film surface. It may be desirable to provide enough space between the contacts to allow detection of absorbed analytes near the surface of the photoelectrocatalytic films 1808. Also, although only two contacts per photocatalytic film are shown, more contacts could also be employed in other embodiments. For example, in some cases, a 4-point-probe arrangement may be used for monitoring conductivity changes, photocurrent and/or photovoltage, in the PEC film.

Figure 19:
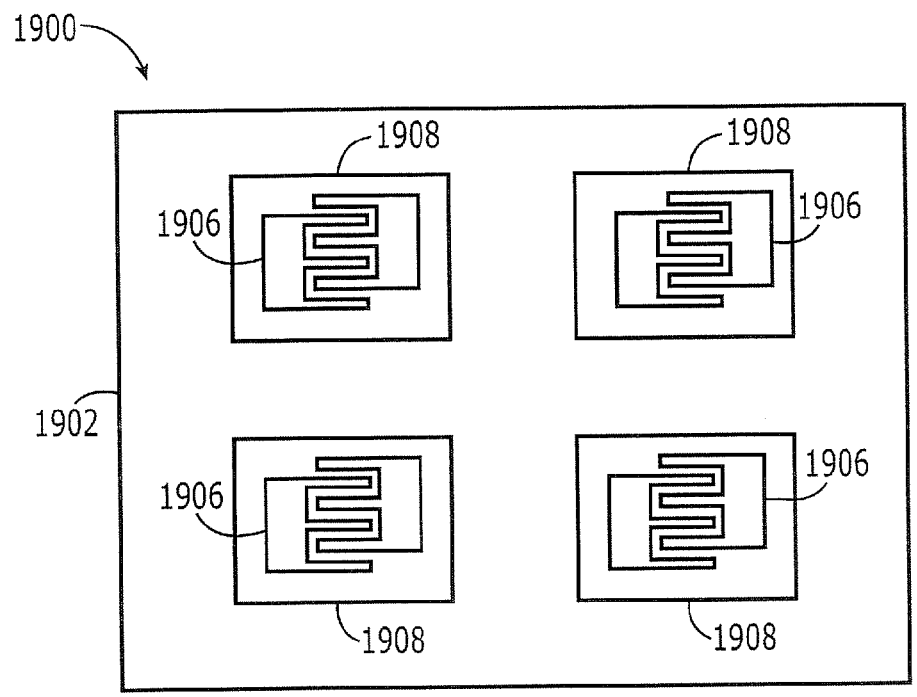
FIG. 19 is a top view of a photoelectrocatalytic sensor according to other embodiments of the present invention, illustrating interdigitated structures according to various embodiments of the present invention.

A variety of PEC element configurations can be implemented according to various embodiments of the invention. In some embodiments 1900 (FIG. 19), interdigitated metal contacts 1906 are patterned onto the PEC films 1908. The interdigitated metal contacts may allow conductivity, capacitance, photocurrent and/or impedance to be monitored in the same device structure more readily than with simpler electrodes. In some cases, the metal electrodes of each interdigitated pair may be dissimilar metals. For example, one metal may form a rectifying contact with the PEC film and the other may form an ohmic contact. For the interdigitated PEC electrodes 1900 of FIG. 19, a reference region of electrodes can be generated by depositing an insulating optically transparent film (such as $SiO_2$, SiN, TiN, TaN etc.) over some electrodes while leaving other electrodes exposed to analyte. In this way, the photoconductive response of the reference electrodes can be deconvoluted from the photoconductive+photoelectrocatalytic response of the exposed electrodes. This reference electrode may be part of the contact layer 709.

Figure 20:
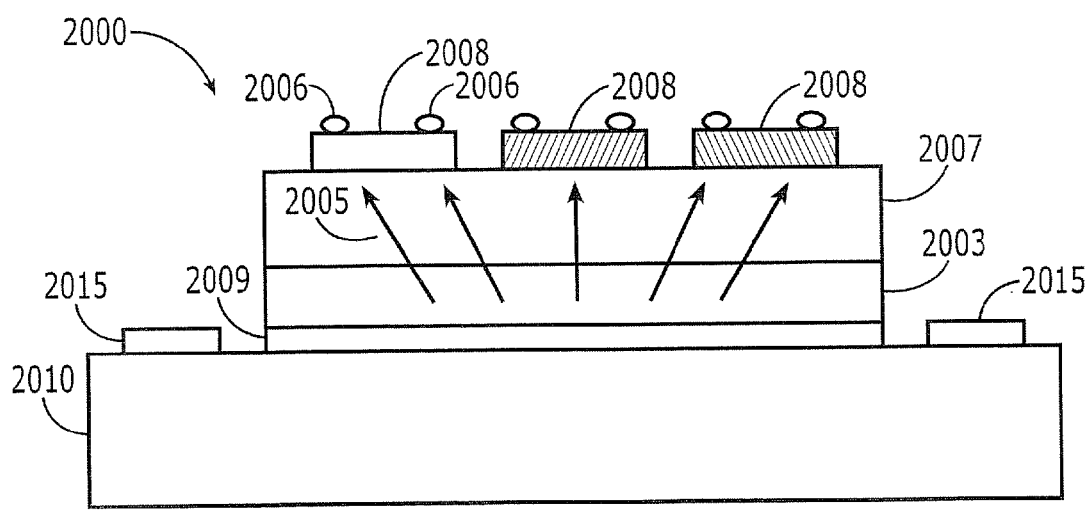
FIG. 20 is a cross-sectional view of a photoelectrocatalytic sensor according to still other embodiments of the present invention, where the photoelectrocatalytic electrodes are arrayed directly on a backside of a transparent substrate of a flip-chip LED.

A "flip-chip" monolithic PEC sensor 2000 integrated into a flip-chip LED (or LD) die according to other embodiments of the invention is illustrated in FIG. 20. In this sensor 2000, the PEC elements and the LED source are monolithically integrated onto two different sides of the same substrate, which can simplify packaging and/or back-end alignment. In these embodiments, PEC electrodes may be fabricated on the transparent substrate-side ("backside") of a flip-chip LED die. For example, GaN UV LEDs may be grown epitaxially on the polished "frontsides" of transparent sapphire substrates, and the sapphire backsides are available for the deposition of metal oxide catalyst films and the fabrication of PEC electrodes through standard photolithographic techniques well known to those skilled in the art of microlithography. Optical energy 2005 from the LED 2003 passes through the transparent substrate 2007 and excites the PEC electrodes 2008 at the surface. As analyte at the PEC electrode surface (not shown in FIG. 20) is ionized by the PEC effect, a net electrical charge forms at the electrode surface. This charge can be monitored through electrical contacts 2006 on each PEC electrode 2008 that may be connected with wirebonds to a set of connector pins 2015. The wires of the wirebonds are not shown in FIG. 20 for simplicity and clarity. The entire monolithic PEC sensor 2000 can be packaged onto a flip-chip board 2010 such as a Bergquist board, FR-4, alumina and/or the like. An interface layer 2009 may be provided to connect the metal contacts of the LED 2003 to the flip-chip board 2010. In some cases, the interface layer 2009 may also include a silicon submount or the like, although this may increase the thermal resistance between the LED and the package.

Figure 21:
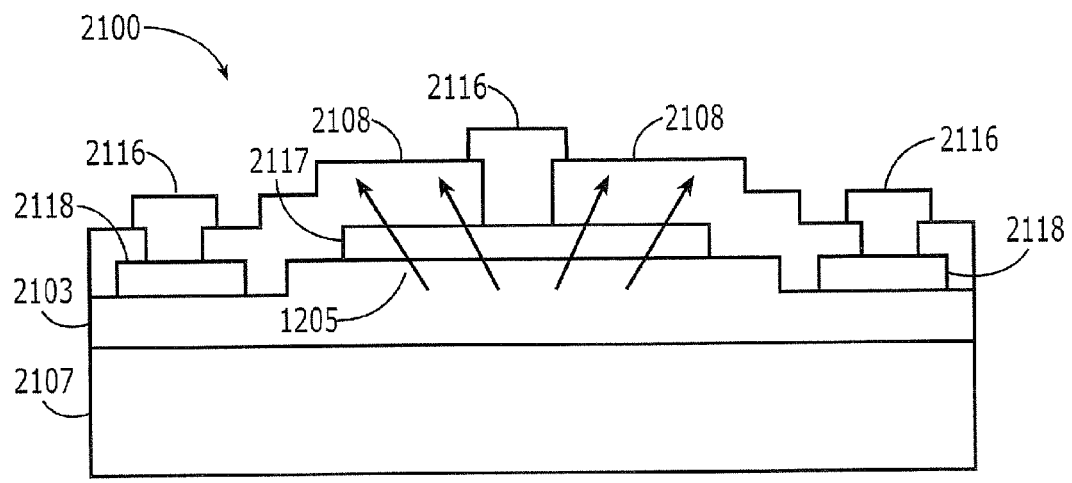
FIG. 21 is a cross-sectional view of a photoelectrocatalytic sensor according to various embodiments of the present invention, where the photoelectrocatalytic material is integrated into a passivation or p-contact of an epi-up LED.

FIG. 21 illustrates an "epi-up" monolithic PEC sensor 2100 according to still other embodiments, where the PEC film 2108 also serves as passivation for the LED epitaxy 2103. Because light 2105 leaves the top of the LED as opposed to the bottom through the substrate 2107, there may be no need to provide mounting layers, such as 2010 of FIG. 20, for electrical contact. The mounting layers for sensor 2100 can be virtually any solid layer that is sufficiently thermally conductive. A TO-header, printed circuit board, ceramic board and/or Bergquist board could each serve as a mounting structure. The n-(2118) and p-(2117) contacts of the LED epitaxy 2103 may be isolated by a mesa pattern in the LED epitaxy. Mesa patterns are typically formed by standard microlithographic dry-etching techniques, such as reactive-ion etching or plasma-etching. Methods for fabricating GaN-based LEDs are well known. The n- and p-bond pads 2116 may be metal layers serving to connect the contact layers with external electronics for electrical communication and/or powering. The bond pads 2116 may be deposited after etching windows through the passivation layer 2108 via wet- and/or dry-etching techniques. In some embodiments, the PEC film 2108 can serve as both the PEC catalyst as well as the dielectric passivation layer, all in one film. In other embodiments, the PEC film 2108 may cover a separate passivation layer already covering the LED epitaxy 2103.

As with the flip-chip PEC sensor of FIG. 20, the epi-up PEC sensor of FIG. 21 may be thought of as a traditional LED structure with the addition of a monolithically integrated PEC film. This PEC film can be deposited by well-developed deposition methods such as plasma-enhanced chemical vapor deposition (PECVD), low pressure chemical vapor deposition (LPCVD), magnetron sputtering and/or the like. Additionally, more experimental deposition techniques, such as modulated-laser deposition, can be used to ablate metal oxide targets for epitaxial growth of metal oxide films on a substrate layer, such as sapphire.

PEC sensors according to embodiments of FIGS. 20 and 21 can be used to sense volatile analyte near the PEC surface. Analyte near the surface is ionized (reduced or oxidized) following photo-excitation of the PEC film (2008 and/or 2108). This imparts a net charge on the surface which can modulate the p-n junction depletion region inside the LED epitaxy (2003 and/or 2103). An example of the band diagram structure for a monolithic PEC sensor in the presence of a reducible analyte is presented in FIG. 28.

Figure 28A:
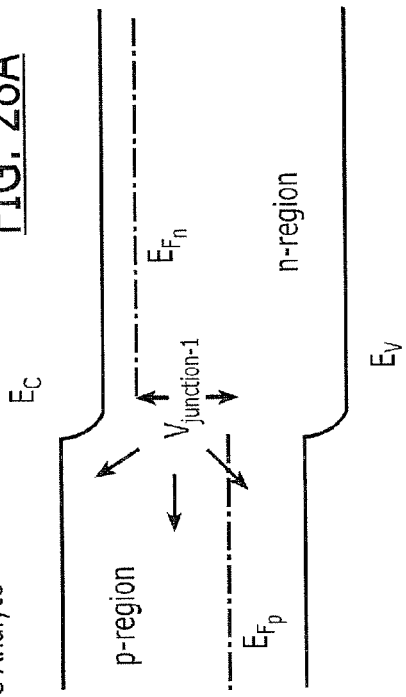
FIGS. 28A and 28B illustrate band diagrams for photoelectrocatalytic sensing of a reducible analyte.
Figure 28B:
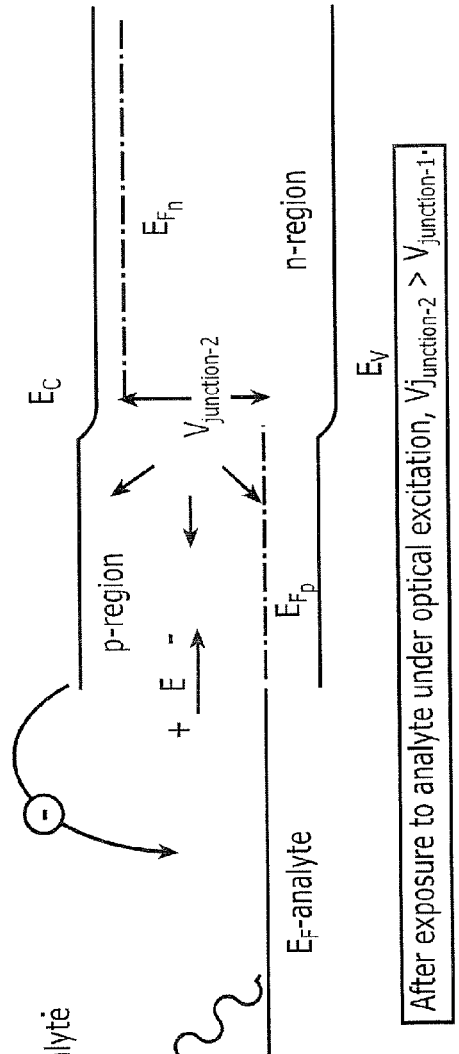
Figure 28C:
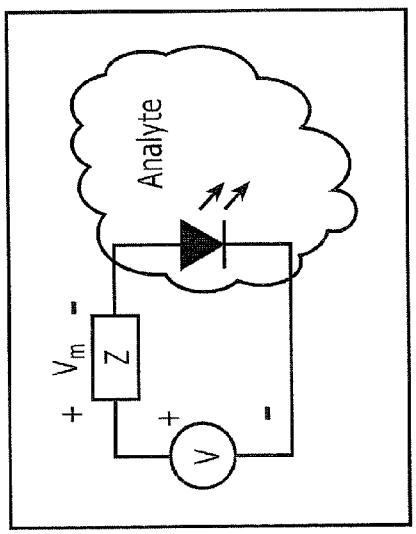
FIG. 28C is a circuit diagram for embodiments of FIGS. 28A and 28B.

The band diagram of FIGS. 28A and 28B show the p- and n-region depletion region only, as it is assumed that the PEC film covering the LED surface is highly insulating and not generating a significant depletion region in the p-doped epitaxy. Before analyte reaches the monolithic PEC sensor surface, the LED is running under normal operational bias (shown in FIG. 28A). Following the exposure to a reducible analyte species, photo-excited electrons are injected into the analyte, reducing the analyte, and leaving a net positive charge on the PEC film, as shown in FIG. 28B. This net charge increases the junction voltage drop, increasing the forward LED impedance. As a non-limiting example of measuring the PEC response shown in FIGS. 28A and 28B, a biasing circuit having a series impedance, Z, and a regulated constant voltage source, V, can be used, as shown in FIG. 28C. The voltage drop across Z, shown as $V_M$, will be a function of the voltage drop seen at the LED, which is in turn a function of the analyte PEC response. These embodiments can provide for monitoring various analytes with a monolithic PEC sensor and a simple circuit. A similar circuit can involve an oscillating voltage source, and the insertion loss of the circuit can be measured as a function of the capacitive reactance of the Z/LED series. A variety of other monitoring circuits can be used which are well known to those skilled in the art. For example, an oxidizable analyte may leave a net negative charge on the PEC film, thereby lowering the LED impedance.

Figure 22:
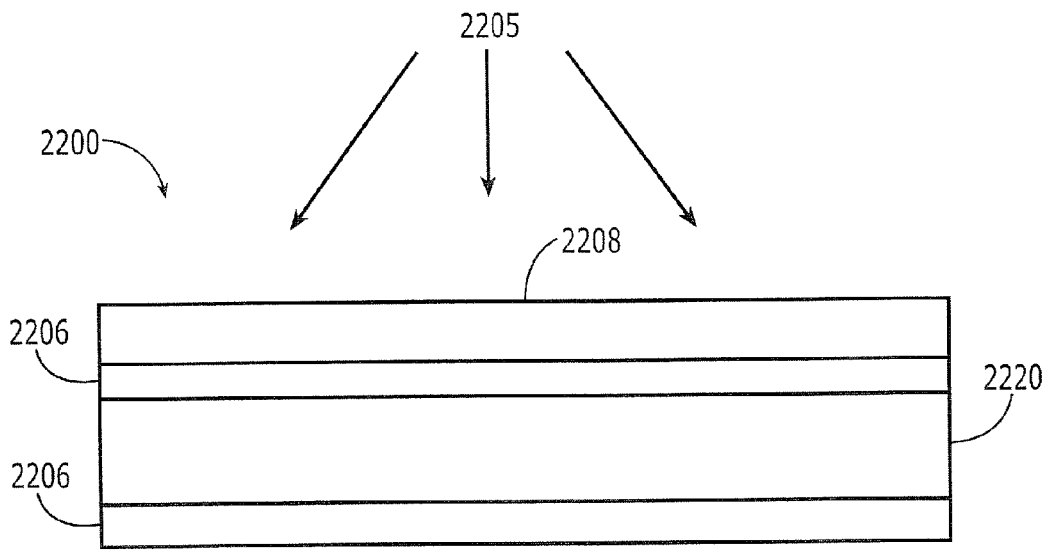
FIG. 22 is a cross-sectional view of a photoelectrocatalytic sensor according to other embodiments of the present invention, where the photoelectrocatalytic electrodes are arranged as a capacitor.

A capacitive PEC element according to other embodiments of the invention is illustrated in FIG. 22. The PEC film 2208 accumulates charge in the presence of analyte and photo-excitation 2205. This charge is imaged on the conductive plates 2206 of the capacitor. These electrode plates can comprise any conductive material, such as metal, conductive polymer, doped semiconductors, conductive ceramics and/or the like. A dielectric medium 2220 exists between the conductive plates to form a stable capacitance between the plates. The charge imaged on the plates is directly proportional to the amount of ionized analyte, and this charge can be measured electrically and/or optically. In some embodiments, the top plate of the conductive plate electrodes 2206 contains no metal, but rather, the PEC film 2208 itself can serve as the top plate.

Figure 23:
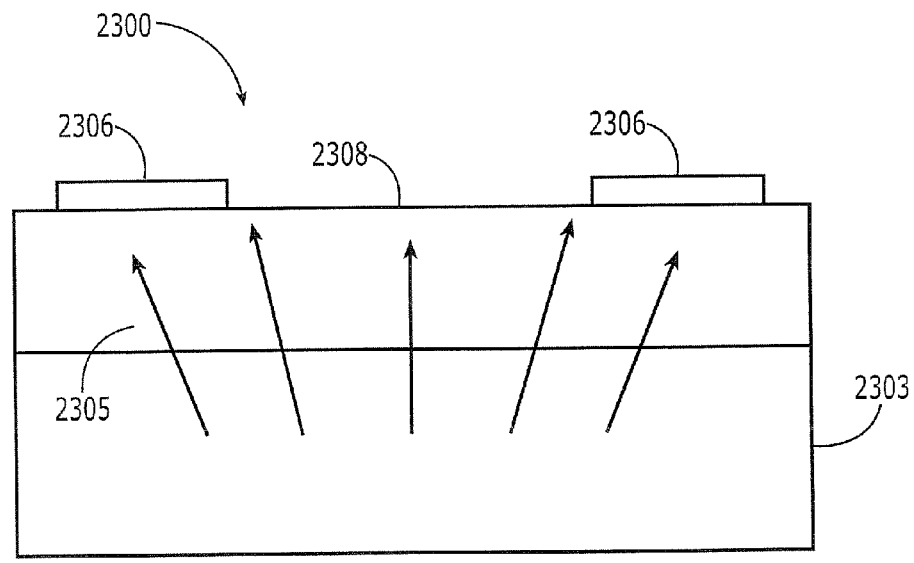
FIG. 23 is a cross-sectional view of a photoelectrocatalytic sensor according to other embodiments of the present invention, where the photoelectrocatalytic electrodes are arranged as a structure that can measure charge, photocurrent, capacitance and/or impedance in the same device.

A cross-section (side view) of a simple interdigitated PEC electrode 2300 according to some embodiments of the invention is shown in FIG. 23. A top-view was shown in FIG. 19. In these embodiments, the conductive electrodes 2306 are located on top of the exposed PEC film 2308. Optical excitation 2305 from the underlying optical emitter 2303 generates photocatalysis in analyte near the PEC film surface. As with the other PEC structures, the optical emitter 2303 may be a monolithic LED or LD, or may be a complete packaged optical source, such as the packaged LED shown in FIG. 12 and/or FIG. 27.

Figures 24A, 24B:
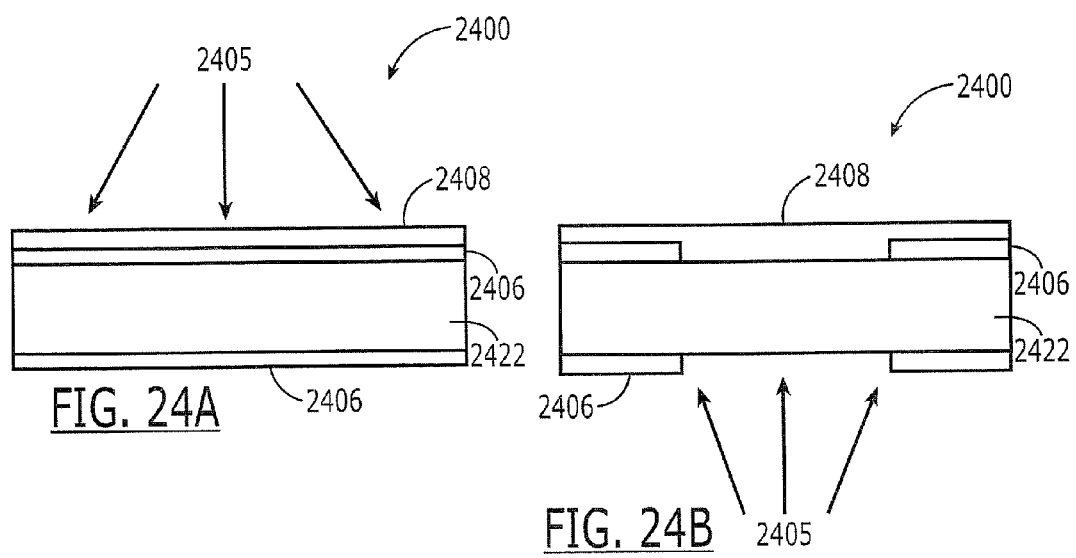
FIGS. 24A and 24B are cross-sectional views of photoelectrocatalytic sensor configurations according to various embodiments of the present invention, where the photoelectrocatalytic electrodes are arranged on a piezoelectric material.

FIGS. 24A and 24B illustrate piezoelectric PEC elements 2400 according to other embodiments of the invention. In these embodiments, optical photo-excitation 2405 generates a charge at the exposed PEC surface 2408 only in the presence of analyte. Charge from the PEC film 2408 generates a field between the electrically conductive electrodes 2406 on either side of a piezoelectric crystal 2422. This field mechanically actuates the piezoelectric crystal via the piezoelectric effect, and this mechanical deflection can be detected electrically, magnetically, optically and/or acoustically.

For example, in the presence of ionizable vapors, if the UV LED is modulated near the resonant frequency of the piezoelectric crystal, the piezoelectric crystal will mechanically resonate as net charge accumulates and dissipates along the PEC film. This mechanical resonance can be detected remotely by an acoustical sensor tuned to the resonant frequency of the piezoelectric crystal. In piezoelectric monitoring, either or both the amplitude and frequency of the electromechanical vibrations can respond to the PEC effect in the presence of analyte, and this vibrational response can be related to the analyte type and concentration. The mechanical resonance can also be detected electrically through the piezoelectric electrodes 2406. As a further example, optical energy directed toward the piezoelectric crystal will be scattered or modulated in relationship to the mechanical motion of the piezoelectric crystal. FIGS. 24A and 24B show piezoelectric PEC sensors of different configurations. In FIG. 24A, the conductive electrodes are mostly contiguous, whereas in FIG. 24B, the conductive electrodes have at least one opening for photo-excitation 2405 to pass through the piezoelectric crystal 2422 and through the PEC film.

Figure 25A:
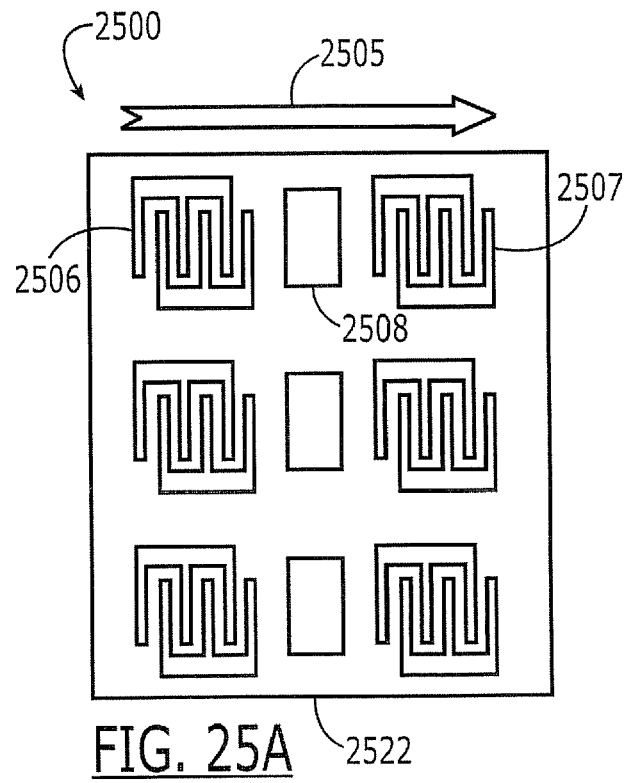
FIGS. 25A and 25B are top views of photoelectrocatalytic sensors according to still other embodiments of the present invention, where the photoelectrocatalytic electrode is integrated in the active region of a Surface Acoustic Wave (SAW) device and the photoelectrocatalytic electrode is integrated into the driving electrodes of a SAW device, respectively.
Figure 25B:
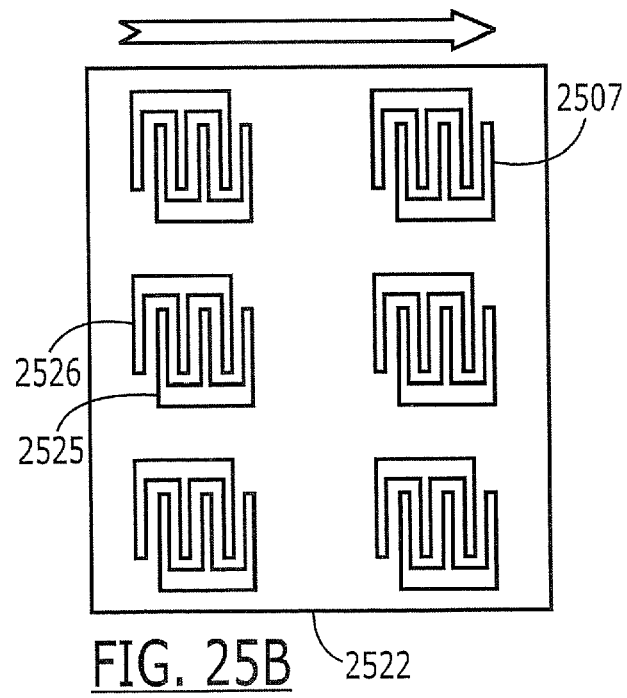

A surface-acoustic-wave (SAW) PEC sensor electrode 2500 according to yet other embodiments of the invention is illustrated in FIGS. 25A and 25B. For simplicity and clarity, the PEC photo-excitation is not shown in this figure, though it should be understood that photo-excitation, for example from a semiconductor optical emitter integrated into the PEC sensor, is used for triggering the PEC effect. In the embodiments shown in FIG. 25A, the driving electrode 2506 generates a surface acoustic wave traveling towards the receiving electrode 2507 in the approximate direction shown by the arrow 2505. A PEC film 2508 on the same substrate 2522 as the driving and receiving electrodes, is located between these two electrodes. The substrate 2522 should be sufficiently piezoelectric to generate and propagate a SAW wave at the surface. For example, quartz, aluminum nitride, piezoelectric lead zirconium titanate (PZT) and/or other piezoelectric solid state films may be used as SAW substrates. In response to volatile analyte near the photo-excited PEC film 2508 surface, a net charge accumulates in the PEC film, and this charge can affect the intensity, speed and/or propagation of the SAW wave along the piezoelectric substrate 2522. These affected SAW properties are received by the receiving electrode 2507 and converted to electrical energy, via the piezoelectric effect, providing a method of sensing the presence and/or concentration of volatile analyte near the PEC film 2508 surface.

In FIG. 25B, the PEC film 2526 is one of the driving electrodes (2526 and 2525) such that the SAW signal is generated by the PEC effect itself. In these embodiments, charge generated in the presence of analyte species and photo-excitation generates a voltage between the PEC film electrode 2526 and the metallic electrode 2525. To facilitate this process, the metallic electrode 2525 can be grounded or set at nominal fixed potential. The voltage generated by the PEC effect in turn generates a SAW signal that propagates towards the receiving electrode 2507. The receiving electrode then converts SAW signal into an electrical signal as previously described. In both FIGS. 25A and 25B, it should be noted that these PEC SAW electrodes can be arrayed with multiple PEC films as illustrated in the figures, thereby providing a PEC sensor 2500 that can have enhanced specificity to particular analytes.

Other embodiments of the invention that can sense various volatile analytes by combining thermocatalysis with photocatalysis are illustrated in FIGS. 26A and 26B. Two separate embodiments are outlined in FIGS. 26A and 26B. In FIG. 26A, the PEC electrodes 2608 are arrayed on the surface of a substrate 2609. A thermal gradient 2610 is applied in at least one direction along the PEC electrode array 2608. A semiconductor optical source generates photo-excitation 2605 to trigger the PEC effect in the presence of volatile analyte (not shown). Because volatile vapors are generally characterized by different catalytic and surface interaction properties at different temperatures, some vapors will interact more readily with PEC electrodes at hotter or colder temperature. Thus, the PEC electrode signal intensity may be greater in some electrodes as opposed to others, and this difference can be used to enhance the specificity of the PEC electrode array 2600 to particular analytes, such as VOCs. In these embodiments, the individual PEC electrodes of the PEC electrode array can be the same catalyst and still provide analyte specificity. Again, this is because of the temperature-dependent interaction of VOCs with a given catalyst, such that interaction for some VOCs is stronger at higher temperatures whereas for other VOCs this catalytic interaction is weaker with increasing temperatures. In embodiments of FIG. 26A, the PEC effect can be used to sense these temperature-dependent interactions. The potential benefits of using the PEC effect over the thermocatalytic effect for sensing these interactions has been described above and will not be repeated for the sake of brevity.

The thermal gradient 2610 of FIGS. 26A and 26B can be generated with localized filament heaters, monolithic patterned resistors, a resistive heater, a graded filament heater, a radiative source and/or the like. In some cases, the gradient may be provided by positioning a filament heater on one end of the substrate layer 2609, such that the temperature decreases with distance away from the heater. Providing a thermal gradient may consume significant power to generate the heat, but not as much as that consumed for the pure thermocatalysis technique.

FIG. 26B illustrates other embodiments that combine thermocatalysis and photocatalysis where a thermal gradient is not needed. In these embodiments, thermocatalysis is provided by optical radiation, such as IR radiation 2611, directed towards the PEC electrode. The higher the optical radiation 2611, the higher the surface temperature of the PEC electrode. Thus, the temperature of each PEC electrode can be independently regulated by optical excitation from a separate optical heating source. In some embodiments, a single UV PEC excitation source is integrated with multiple IR sources (such as IR LEDs), one IR source for each PEC electrode. In other embodiments, the PEC films in the PEC electrodes are doped with an optically absorbing impurity that absorbs light at one or more sub-band-gap wavelength(s), turning the optical energy into thermal energy. Different doping methods in neighboring PEC films can result in different thermal heating rates and thus provide a different surface temperature for each PEC film. In yet other embodiments, the PEC electrodes 2608 are located on films that generate thermal energy in response to a particular wavelength of light. In yet other embodiments, a single UV source, a single thermal radiation source, and a single PEC electrode may be employed for specifying between multiple volatile analyte species. This may be achieved by cycling the thermal radiation source in the presence of UV excitation such that the PEC effect is monitored in the PEC electrode during thermal cycling. Because each VOC generally has a unique thermal characteristic, this thermal characteristic can be monitored by the PEC effect as a function of both temperature and time and used to identify the presence and intensity of various VOCs and other volatile species. One or more arrays of multiple PEC excitation sources, multiple thermal radiation sources and/or multiple photocatalysts can be employed to further specify one analyte species from another. Additionally, one or more "white" or multiwavelength sources can be used in conjunction with a prism or other refracting or diffracting source to generate multiple wavelengths from the same optical source.

The electrodes of FIGS. 22-26 may serve as the PEC electrodes 1708 of the PEC sensor 1700 of FIG. 17. The electrodes of FIGS. 22-26 may also serve the more general PEC elements (comprised of 708, 709 and 707) for the PEC sensor embodiments 700 of FIG. 7. In general, it should be understood that any of the PEC electrode configurations described herein can be used in any of the PEC sensing devices and methods described herein. Additionally, the electrodes can take other configurations according to other embodiments of the invention. For example, the PEC film can be part of the gate in a gated electronic device, such as the gate of a field-effect transistor (FET), a gated diode, a gated photodiode and/or the like. Thus, the PEC film can be part of an electronic device having 3 or more terminals. Furthermore, rather than forming entire new PEC sensors, the PEC films can be formed on commercially available device wafers, device die, or fully packaged devices and systems. For example, one or more PEC films can be selectively deposited or selectively patterned over a commercially available metal-oxide semiconductor field-effect transistor (MOSFET), a heterostructure field-effect transistor (HFET), resistor, diode, photodiode and/or the like, such that the PEC film covers at least one active terminal of the device. For example, the PEC film can be deposited directly on the gate contact metallization of a commercially available FET or the contact metallization of a commercially available resistor or diode. In yet other embodiments, a PEC element can be integrated at least partially with a microelectromechanical system (MEMS) device.

Figure 29:
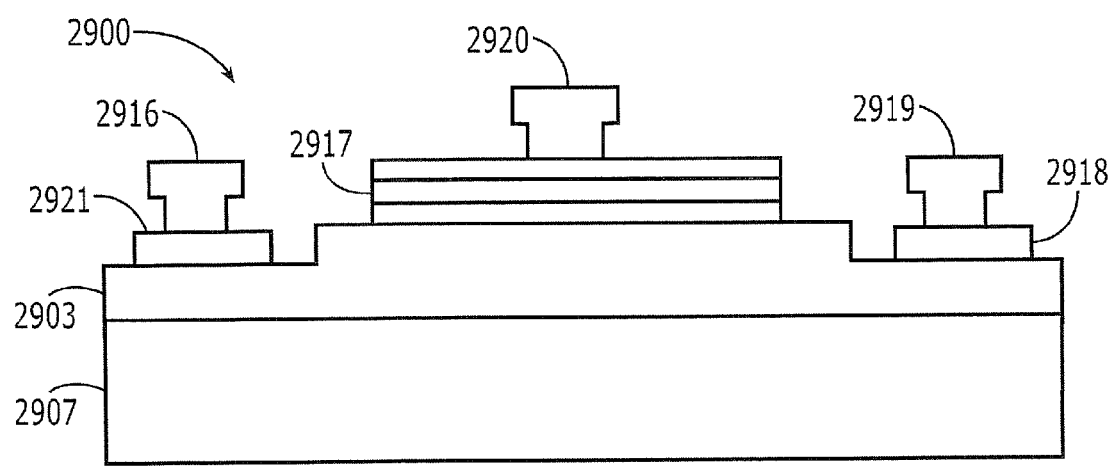
FIG. 29 is a cross-sectional view of a photoelectrocatalytic sensor according to various embodiments of the present invention, where a photoelectrocatalytic material is integrated into one or more layers of a gate of a field effect transistor (FET).

The broad range of PEC electrode configurations is exemplified by the gated FET structure 2900 of FIG. 29. The source 2921 and drain 2918 contacts of the FET epitaxy 2903 are isolated by a mesa pattern underneath the gate layers 2917. The source 2921 and drain 2918 contacts are typically composed of one or more metals, and in some cases these contacts cover specially doped layers of epitaxy 2903 to promote current flow. Mesa patterns are typically formed by standard microlithographic dry-etching techniques, such as reactive-ion etching or plasma-etching. The methods for fabricating FET structures are well known to those having skill in the art. The source and drain bond pads, 2916 and 2919 respectively, may be metal layers serving to connect the source and drain contacts, 2921 and 2918 respectively, with external electronics for electrical communication and/or powering. The gate bond pad 2920 may be connected with external electronics, connected with a reference electrode, or unconnected and left electrically floating. In some embodiments, the gate bond 2920 pad may not be used. There may also be a passivation layer (not shown in FIG. 29) covering part of the device, and this passivation layer is typically an oxide, nitride, or combination of oxides and nitrides, but any insulating dielectric can be used. Typically, these dielectrics should not generate charge with UV light; for example, it generally is desired that the band gaps for these dielectrics should be greater than the energy of the UV excitation photons. The substrate layer 2907 is typically a solid crystalline or polycrystalline material, as described elsewhere herein. In the FET structure 2900, the gate layers 2917 are primarily used to modulate the conductance of one or more channels in the FET epitaxy 2903 between the source 2921 and the drain 2918 contacts. The thickness of the films in FIG. 29 typically ranges from a few tens of Angstroms to several microns.

The gate layers 2917 are shown as 3 separate layers in FIG. 29 to highlight an embodiments of a PEC gated structure 2900. In the gate layers 2917, at least one layer is composed of at least one PEC material. In other embodiments, at least one layer is composed of at least one PEC material and at least one layer is composed of at least one dielectric material. In yet other embodiments, at least one layer is composed of at least one PEC material and at least one layer is composed of at least one metallic material. In still other embodiments, the gate layers 2917 consist of simply one layer—the PEC layer. In other embodiments, only two layers are used. In other embodiments, more than one type of PEC material exists in the gate layers 2917. Moreover, although the FET structure 2100 is illustrated as a MOS-type structure on a single-crystal substrate, it should be understood that a MOS-type structure on a flexible substrate, a polymer substrate, organic material and/or other material can be used in other embodiments of the invention. Additionally, other transistor configurations, such as bipolar junction transistor configurations, can also contain PEC material for modulating the net charge or conductivity of the emitter, collector, base, or other layers.

Thus, gate layer(s) 2917 may be configured in a variety of configurations to allow the gate to function as a PEC-enabled gate. For example, PEC charge, in response to analyte and photo-excitation at/near the PEC surface, can be imaged onto a metallic film, a dielectric film, or the FET epitaxy directly. This PEC charge can modulate the conductivity of the conductive channel between the source and drain in proportion to the concentration of analyte at the gate 2917 surface. Different gate layer 2917 configurations can provide control over device capacitance, speed, selectivity and/or reliability. Additionally, in the gate layers 2917 of FIG. 29, at least one PEC material may be integrated or dispersed within a dielectric or metallic film, providing additional flexibility in PEC sensing. For example, the gate layers 2917 may be a single layer composed of a simple metallic film with regions of PEC material dispersed throughout the film. These PEC materials can be sputtered or deposited into a metallic film at various deposition temperatures. In some cases, at least one component of the gate layers 2917 is composed of at least one nanostructure. This component may also be composed of at least one PEC material.

Figure 30:
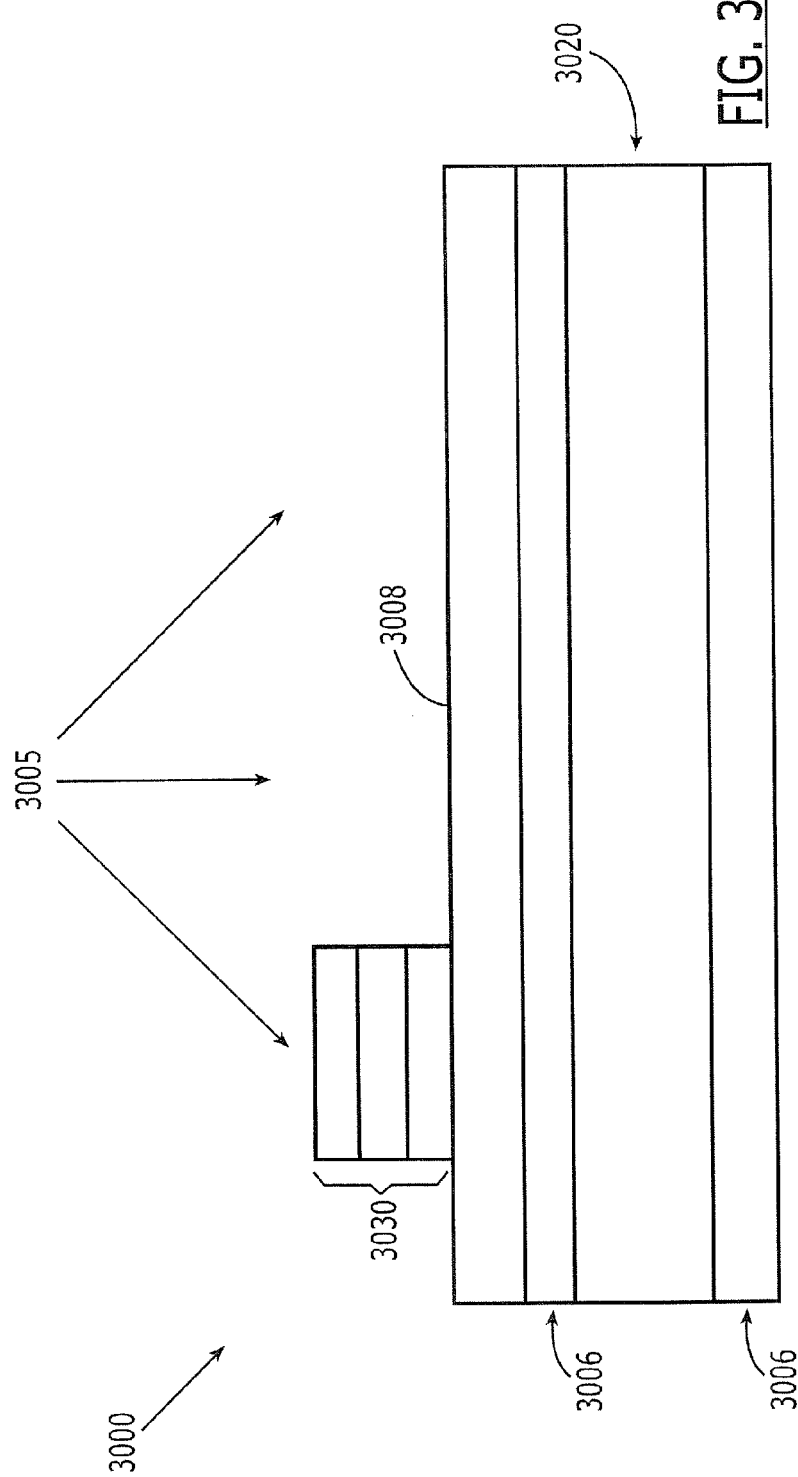
FIG. 30 is a cross-sectional view of a photoelectrocatalytic sensor according to various embodiments of the present invention, that includes a charge balancing electrode.

In other embodiments of the invention, an additional electrode may be provided to modulate, regulate, regenerate and/or balance charge near the surface of the PEC film. For example, oxidized or reduced analyte near the PEC surface may reside near the surface, and this may generally be undesirable. Because the lingering analyte may possess charge that is equal to the charge in the PEC surface, but opposite in polarity, the net charge at the surface may be at or near zero. An additional electrode near the PEC surface can reduce or eliminate this effect. FIG. 30 shows a 3-electrode PEC capacitor 3000 comprising a charge-balancing electrode 3030 on the PEC capacitor 2200 of FIG. 22. The balancing electrode 3030 is shown as three layers to emphasize that this electrode may be comprised of one or more layers. In some embodiments, the reference electrode comprises an electrically insulating layer adjacent to the PEC film 3008 and an electrically conducting layer adjacent to the insulating layer. In other embodiments, a third layer adjacent to the electrically conducting layer provides electrochemical protection to the balancing electrode 3030. For example, the insulating layer may be an insulating dielectric layer, the conducting layer may be a metallic layer, and the electrochemical protection layer may be a native oxide to the conducting layer and/or another dielectric layer. In other embodiments, the balancing electrode 3030 may be comprised of a conducting layer only, or an insulating and conducting layer only. Other combinations may be used as well. Photoexcitation 3045 may be provided by a semiconductor light emitting source according to various embodiments of the invention described herein.

Figure 31:
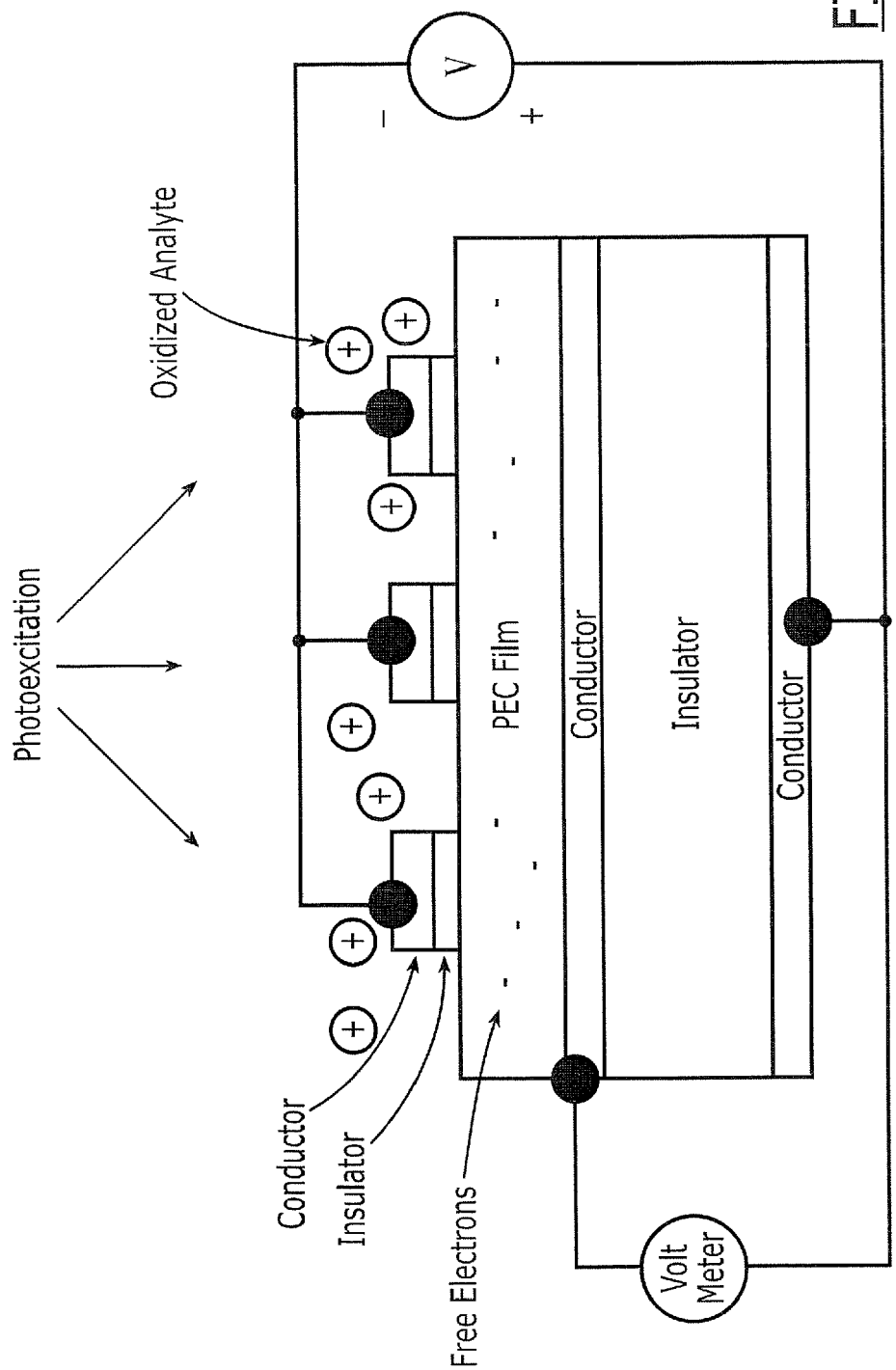
FIG. 31 is a cross-sectional view of a photoelectrocatalytic sensor according to various embodiments of the present invention, that includes a plurality of charge balancing electrodes.

FIG. 31 shows how a circuit comprising the 3-electrode PEC capacitor 3000 may operate for sensing a voltage response to a photocatalyzed analyte near the PEC surface. Multiple balancing electrodes, each composed of at least one insulator and one conductor, are arrayed across the surface of the PEC film. The insulator of the balancing electrode may be used to electrically isolate the conductor of the balancing electrode from the underlying PEC film and the underlying capacitor structure. Oxidized positively charged analyte (shown as positively charged circles) from photocatalysis are attracted to the balancing electrode via electrostatic potential. This leaves a net negative charge near the PEC film that alters the potential across the capacitor electrodes, and this can be measured electrically through a voltmeter across the capacitor electrodes. In these embodiments, the balancing electrode can provide a net negative charge at the surface that can be measured as a voltage through a voltage detecting circuit (V). Without a biased balancing electrode, positively charged oxidized analyte may reside at the surface, attracted to the net negative charge in the PEC film, providing a zero or near-zero net charge near the PEC-analyte surface. Thus, a change in potential may be difficult to observe or may not be observed in the presence of photocatalyzed analyte.

The balancing electrode 3030 can be fabricated via standard microelectronic photolithography. For example, a dielectric film (the insulating film) and conductive film can be deposited, in sequence, over the PEC film. The conductive film and dielectric film can then be patterned via wet- and/or dry-etching techniques. A variety of geometries can be used for the balancing electrode 3030, such as rectangles, squares, circles, triangles, interdigitated fingers, etc., in various embodiments of the invention. Though the balancing electrode 3030 is shown, for exemplary purposes, along with a PEC capacitor device, it should be noted that the balancing electrode 3030 can be used in virtually any device configuration, such as a diode, transistor, light-emitting device and/or other devices as described herein.

In other embodiments, a biasing technique can be used to clear the surface of charged analyte even without a balancing electrode 3030. For example, a positive potential bias between the top and bottom electrodes 2206 of the PEC capacitor 2200 can repel positively charged analyte near the PEC surface. Following the electrostatic deflection of analyte from the surface, the net negative charge in the PEC film can be measured. A variety of other electrostatic and/or electrodynamic charge balancing techniques can be used to facilitate a net charge in the PEC film for voltage measurements in response to photocatalyzed analyte. Other techniques for cleaning the surface of charged analyte can include thermal pulsing and/or electromagnetic excitation of the surface. For example, an infrared source, such as an IR LED, can be modulated and directed upon the PEC surface to energize the bound analyte and encourage the removal of charged analyte bound at the surface.

In other embodiments of the invention, a PEC diode 3200 can be used to detect analyte fluids. Some diode embodiments are illustrated in FIGS. 32A and 32B. Referring to FIGS. 32A and 32B, a PEC film 3208 is adjacent to at least one electrical contact 3206 of a PEC diode 3200. Photoexcitation 3205 stimulates photocatalysis at the PEC surface, leaving a net charge in the PEC film which can modulate the space charge region in the diode structure 3203. Modulation of the space charge can be detected as a voltage or current response across the electrical contacts 3206 of the diode. The vertical PEC diode of FIG. 32A may operate with optical excitation on the top-side whereas the lateral PEC diode of FIG. 32B may operate with optical excitation from the back-side. For PEC excitation from the backside of diode of FIG. 32B, the diode structure 3203 may need to be sufficiently transparent to the photoexcitation light 3205. Additionally, the electrical contact 3206 adjacent to the PEC film 3208 may need to be sufficiently transparent to the photoexcitation light 3205.

The PEC diode structures 3200 of FIGS. 32A and 32B are examples and do not limit embodiments of this invention to simple diodes. For example, the PEC detection methodology of FIG. 32 can be applied towards virtually any device where at least one space charge region can be modulated. This may be the case for the gate of a field-effect transistor, the gate of a silicon-controlled rectifier, the terminals across a p-n junction and/or other device structures. Additionally, the ability to detect very low analyte levels can be achieved for the case where the diode structure 3203 is that of an avalanche photodiode (APD). In such case, a net charge generated in the PEC film, in response to photocatalyzed analyte, can be amplified by the internal avalanche amplification process of an APD. Additionally, a PEC film can be provided on the photocathode of a photomultiplier tube or semiconductor photomultiplier device for analyte detection via photocatalysis. The design and fabrication of diodes is well known to those skilled in the art, and the deposition and patterning of PEC films on electronic devices has already been described herein.

Methods for fabricating PEC sensors, such as shown in FIG. 12, according to various embodiments of the invention, will now be described. These methods will highlight fabrication processes for a monolithic flip-chip LED PEC sensor (FIG. 21). However, many other processes may be used.

In particular, in some embodiments, AlInGaN LED epitaxy is grown on the epi-ready "frontside" of a crystalline, optically transparent c-plane sapphire substrate via commercialized metal-organic chemical vapor deposition (MOCVD). The term "frontside" refers to the side of the substrate on which the LED epitaxy is primarily grown, and the term "backside" refers to the side of the substrate which is largely free of LED epitaxy. The total LED film thickness may range from about 2 to about 4 µm to reduce strain in the epitaxy, but thicker films are often used. For AlInGaN, n-type layers may be grown first, followed by the active region (for generating light) and p-type layers. Thus, considering the example shown in FIG. 21, 2117 is usually a p-contact and 2118 is usually an n-contact.

Following MOCVD epitaxial growth, the LED wafer may be introduced into a plasma deposition or modulated laser deposition (PLD) tool, for depositing the metal oxide photocatalysts on the epi-free backside of the sapphire wafer. Magnetron sputtering of the photocatalysts, as opposed to PLD, may also be used. Other deposition techniques are also suitable. During PLD, the frontside of the LED wafer can be protected by facing the frontside away from the PLD growth zone or by covering the frontside with a protective "sacrificial oxide," such as $SiO_2$, to be subsequently removed. PLD targets can be generated by sintering powdered mixtures of oxides, such as gallium oxide, magnesium oxide, zinc oxide and/or aluminum oxide. Sometimes, these oxides can be mixed with rare-earth oxides, such as $Eu_2O_3$ for more specialized optoelectronic effects (FIG. 16C). During PLD, these targets may be ablated by an excimer laser under high vacuum (~$5 \times 10^{-8}$ torr), and the by-products settle on the substrate to form a contiguous, crystalline oxide film. Film growth can be performed at a wide range of temperatures, but about 700-900° C. may be used in some embodiments. A temperature should be maintained that will not destroy the AlInGaN epitaxy, which is primarily on the frontside of the substrate. Multiple catalyst films can be deposited sequentially by changing the PLD target inside the PLD deposition tool. This can be automated during PLD growth without having to open the PLD reactor or break vacuum. For example, a gallium oxide target can be ablated first, followed by a magnesium oxide target, then followed by a praseodymium-doped gallium oxide target, etc., yielding a layered luminescent film of the same order structure as the ablated target procession.

In some cases, as in the case of FIG. 12, the photocatalytic films may be deposited on a transparent substrate, such as quartz or sapphire, that is not part of the AlInGaN LED. This process can reduce concerns associated with multiple oxide deposition runs on a wafer covered with sensitive AlInGaN epitaxy.

It should be noted that growth conditions during PLD, magnetron sputtering, MOCVD, and the like may play a large role on the optical quality of the deposited films. For example, growth at higher temperatures may encourage high-crystalline growth and may support dopant incorporation at optically active lattice sites. Furthermore, by nanoscale engineering, nanostructures can form quantum dots and/or quantum wells which can further support radiative recombination efficiency and overall brighter optical output. For example, depositing thin, nanoscale (e.g., <100 nm) films of lower band gap material surrounded by higher band gap material can result in higher radiative recombination efficiency within the lower band gap film. The film deposition processes described herein, and methods of incorporating high-brightness nanostructures, shall be regarded as non-limiting examples, and may be modified by those skilled in the art without diverging from the intent of the invention. Furthermore, the morphology of the metal oxide surface can dramatically affect surface adhesion, electrostatic attraction, analyte diffusion, adsorption/desorption and/or other types of physical interactions between the analyte and the metal oxide photocatalyst.

Following growth, the resulting wafer can be processed as a standard AlInGaN LED, using photolithography steps well known to those skilled in the art. However, if photocatalysts are deposited onto the backside the backside of the substrate of the LED wafer, as in 2000 of FIG. 20, the backside may need to be protected throughout processing. Processing may start with a solvent clean of the wafer surface, sometimes followed by an acid clean. The photocatalyst films on the sapphire backside can be protected by utilizing a sacrificial layer of protective photoresist during acid cleans and oxide etching steps. This sacrificial layer is typically removed before annealing steps. Following the clean, selective p-contacts may be formed on the surface of the AlInGaN epitaxy, followed in order by mesa formation, n-contact metallization formation, contact annealing, surface passivation, and bond pad formation. Typical p-contact metallizations are nickel oxide-gold alloy (NiO/Au), nickel, platinum and/or silver. Typical n-contact metallizations are Ti/Al, Al and/or Ti alloys. Metallization can be formed via standard e-beam/ thermal evaporation or sputtering techniques. Mesa formation is typically executed by dry-etching approaches, with chlorine-based chemistries, such as reactive ion etching (RIE) and/or inductively coupled plasma (ICP) etching. The mesas may be formed to aid with light extraction and to define regions for the n-contact layer. The etched regions may serve as the n-contact interface whereas the mesa tops may serve as the p-contact interface, for the n- and p-contact metallization, respectively. The p-contact layers may be metallized first, prior to mesa formation, to protect the delicate p-type epitaxy from the detrimental effects of RIE or ICP etching steps. Surface passivation may be executed by the sputtering or plasma-enhanced chemical vapor deposition (PECVD) of silicon dioxide and/or silicon nitride, although other dielectrics are also possible. In the monolithic PEC sensor of FIG. 21, the surface passivation is itself the photocatalyst film. In such case, metal oxide films may be deposited primarily by plasma deposition, laser deposition and/or magnetron sputtering. Ti/Ni/Au bond pads may then be patterned by selectively etching holes in the passivation layer along the n- and p-metal contact regions. These bond pads may serve as the location for wirebonds during subsequent LED packaging.

If the substrate backside contains an array of photocatalytic films, these films can be fabricated into PEC electrodes through the standard fabrication steps described above, but in this case the frontside of the LED wafer may need to be protected. For PEC electrodes, a one-step metallization mask can be used to pattern metallic electrode features into the PEC electrodes. In the case of FIG. 12 where the PEC electrodes are fabricated on separate substrates from the AlInGaN LED, there may be more flexibility in the fabrication process. For example, multiple deposition runs can be used to deposit multiple catalysts, without the need to protect the front-side of the substrate, and these catalysts can be selectively etched via dry-etching techniques such that separate, noncontiguous photocatalysts remain. Metal electrodes can then be deposited and patterned on each photocatalyst using the same photolithographic mask. These metal electrodes may be patterned in a variety of geometries, such as interdigitated electrodes, as shown in FIG. 12.

The fabricated LED wafer can be diced or sawed to generate hundreds to thousands of LED die per substrate, typically 1 mm$^2$ in area. These die may then be flip-chip bonded to a silicon submount, and the submount may be mounted to thermal packaging (for heat extraction). In some embodiments, the submount is not used and the LED die may be attached directly to the thermal packaging, with the AlInGaN epitaxy facing down (towards the thermal packaging) and the luminescent film facing up (for light extraction). With the LED fabrication process, sawing, dicing, and packaging can be executed with standard recipes well known to those skilled in the art. Care may need to be taken to protect the photocatalysts that may rest on the backside of the wafer. This can be done by applying a protective tape over the photocatalyst to prevent scratching and/or other mechanical damage during sawing, dicing, packaging, and other back-end processes. Of course, for PEC electrodes on an independent substrate, such as that shown in FIG. 12, these concerns may not exist, as the LED and the PEC electrodes can be processed separately.

Following die separation, the packaged LED die can be mounted on a TO-header. If PEC electrodes are not already on the LED backside, a separate transparent substrate with patterned PEC electrodes can be mounted with the TO-header package (as shown in FIG. 12). Standard gold wirebonds can connect the LED and PEC electrodes with the TO-header. The entire packaged PEC sensor can then be integrated with a telemetric processing board, such as a Bluetooth module, for wireless communication with a cell phone, computer, or PDA. The device processes described herein are non-limiting examples, and can be modified extensively by those skilled in the art without diverging from the intent of the invention.

Other embodiments of the invention include methods of monitoring fluids 706 using, for example, a photoelectrocatalytic sensor and real-time monitor 700 of FIG. 7. These fluids 706 may be gases and vapors from exhaled breath, airborne and waterborne contaminants, industrial pollution, airborne volatile compounds and/or the like. Monitoring fluids from each case may involve different sensor designs. For example, a respiration monitor may be mounted on a portable headpiece or a mouthpiece. In a specific case, a standardized portable phone headset—including a headpiece, an earpiece, and mouthpiece—can incorporate one or more photoelectrocatalytic sensors in the mouthpiece. Such a sensor can facilitate oximetry, capnometry and/or health diagnoses.

A photoelectrocatalytic sensor used as an environmental monitor may be located virtually anywhere. For example, an industrial pollution monitor may be located at or near one or more exhaust ports. In some cases, pollution may come from a motor vehicle, in which case the photoelectrocatalytic sensor 700 may be at or near the exhaust of the vehicle. In a specific case, a portable environmental monitor, composed of the photoelectrocatalytic sensor 700, can be incorporated in a portable wireless instrument such as an earpiece, headset, cell phone, PDA and/or the like. Typical environmental pollutants that may be monitored include ozone, carbon monoxide, VOCs, PAHs and/or the like. Because photoelectrocatalytic sensors 700 do not need a heater filament to initiate the catalytic reaction, these sensors can work well for wearable, human-portable sensors as well as explosion-proof sensors.

It should be noted that the photoelectrocatalytic layers 708 do not need to be layers that respond only to UV light to initiate photocatalysis. For example, indium oxynitride can have a band gap ranging from the mid-IR to deep-UV. Thus, employing a photoelectrocatalytic layer 708 of indium oxynitride in a photoelectrocatalytic sensor 700 can facilitate photocatalysis via IR or visible light as well as UV light, depending on the stoichiometry of the indium oxynitride alloy. Thus, an integrated photoelectrocatalytic sensor 700 of indium oxynitride can incorporate an LED 703 in the visible or IR wavelengths as well as the UV. Moreover, nuclear radiation or X-rays can also be used to ionize the surface of a photoelectrocatalytic sensor.

In the drawings and specification, there have been disclosed embodiments of the invention and, although specific terms are employed, they are used in a generic and descriptive sense only and not for purposes of limitation, the scope of the invention being set forth in the following claims.

What is claimed is:

1. A fluid analyte sensor, comprising:
an array of photoelectrocatalytic elements, a respective one of which is configured to be exposed to the fluid, if present, and to respond to photoelectrocatalysis of at least one analyte in the fluid that occurs in response to impingement of optical radiation upon the respective photoelectrocatalytic element;
an array of semiconductor light emitting sources, a respective one of which is configured to impinge the optical radiation upon the respective one of the photoelectrocatalytic elements; and
an array of heaters that is separate from the array of semiconductor light emitting sources, a respective one of the heaters being configured and independently regulated to separately generate thermal energy and apply the thermal energy to only the respective photoelectrocatalytic element so as to affect interaction between the at least one analyte and the array of photoelectrocatalytic elements.

2. A sensor according to claim 1 wherein the array of photoelectrocatalytic elements comprises a photoelectrocatalytic layer and a plurality of conductive contacts electrically connected thereto.

3. A sensor according to claim 1 wherein the array of photoelectrocatalytic elements comprises a plurality of spaced apart photoelectrocatalytic layers and a plurality of spaced apart conductive contacts electrically connected thereto.

4. A sensor according to claim 1 wherein the array of photoelectrocatalytic elements comprises a reference electrode and/or a charge balancing electrode.

5. A sensor according to claim 1 further comprising a substrate, and wherein the array of photoelectrocatalytic elements, the array of semiconductor light emitting sources and the array of heaters are at least partially monolithically integrated with the substrate.

6. A sensor according to claim 1 wherein the fluid comprises a liquid and/or a gas and wherein the analyte comprises a pollutant, contaminant and/or a component of the fluid.

7. A sensor according to claim 1 wherein the fluid comprises respired gas and wherein the analyte comprises a component of the respired gas.

8. A sensor according to claim 1 wherein the array of semiconductor light emitting sources comprises an array of laser diodes and/or light emitting diodes.

9. A sensor according to claim 1 wherein the array of photoelectrocatalytic elements is configured to respond to photoelectrocatalysis of at least one analyte in the fluid by changing a conductivity, capacitance, inductance, impedance, net charge, optical property and/or mechanical property thereof in response to the thermal energy and the impingement of optical radiation upon the photoelectrocatalytic element.

10. A sensor according to claim 1 wherein the array of photoelectrocatalytic elements further comprises a transistor, a capacitor, a nanostructure, a diode, an amorphous structure, a piezoelectric structure and/or a surface acoustic wave structure.

11. A sensor according to claim 1 wherein the array of photoelectrocatalytic elements and the array of semiconductor light emitting sources include at least one common electrical contact.

12. A sensor according to claim 1 wherein the array of semiconductor light emitting sources includes a passivation layer and wherein the array of photoelectrocatalytic elements is at least partially on the passivation layer.

13. A sensor according to claim 1 further comprising a photodetector that is configured to detect the optical radiation that is emitted by the array of semiconductor light emitting sources and/or optical radiation emitted by the photoelectrocatalysis.

14. A sensor according to claim 1 further comprising a controller that is configured to selectively energize the array of semiconductor light emitting sources and the array of heaters and to detect a response to the photoelectrocatalysis of at least one analyte in the fluid that occurs in response to the thermal energy and the impingement of optical radiation upon the photoelectrocatalytic element.

15. A sensor according to claim 1 wherein the array of photoelectrocatalytic elements is doped with deep level impurities and wherein the array of semiconductor light emitting sources is an array of visible and/or infrared light emitting diodes and/or laser diodes.

16. A sensor according to claim 1 wherein the array of photoelectrocatalytic elements comprises a metal oxide, wherein the array of semiconductor light emitting sources comprises an array of ultraviolet and/or blue light emitting diodes and/or laser diodes.

17. A sensor according to claim 1 further comprising a monitor that is configured to monitor the response to the at least one analyte in the fluid, if present, resulting from the photoelectrocatalysis of the at least one analyte in response to the thermal energy and the impingement of optical radiation upon the array of photoelectrocatalytic elements.

18. A sensor according to claim 1 further comprising a monitor that is configured to monitor energy of the at least one analyte in the fluid, if present, resulting from the photoelectrocatalysis of the at least one analyte in response to the thermal energy and the impingement of optical radiation upon the array of photoelectrocatalytic elements.

19. A sensor according to claim 2 wherein the photoelectrocatalytic layer comprises a plurality of layers of a given photoelectrocatalytic material having at least two different impurities therein.

20. A sensor according to claim 2 wherein the photoelectrocatalytic layer comprises a plurality of layers of different photoelectrocatalytic materials.

21. A sensor according to claim 2 wherein the photoelectrocatalytic layer comprises oxide, carbide, nitride, arsenide, phosphide, sulfide and/or antimonide photoelectrocatalytic compounds and/or metal oxides, metal nitrides, metallic compounds and/or semimetallic compounds thereof.

22. A sensor according to claim 2 wherein the at least one conductive contact comprises at least two interdigitated conductive contacts.

23. A sensor according to claim 14 wherein the controller is configured to repeatedly modulate the array of semiconductor light emitting sources and to detect an electrical response of the at least one photoelectrocatalytic element in response thereto.

24. A sensor according to claim 14 further comprising a wireless transmitter that is responsive to the controller.

25. A sensor according to claim 17 wherein the monitor is configured to monitor an electrical, electromagnetic, mechanical, acoustic and/or thermal response to the at least one analyte in the fluid.

26. A sensor according to claim 18 wherein the monitor is configured to monitor the energy as optical energy of the at least one analyte in the fluid.

27. A solid state device comprising:
an array of photoelectrocatalytic elements;
an array of semiconductor light emitting sources;
an array of heaters that is separate from the array of semiconductor light emitting sources; and
a housing that is configured to position a respective one of the array of photoelectrocatalytic elements, a respective one of the array of semiconductor light emitting sources and a respective one of the array of heaters relative to one another such that the respective one of the semiconductor light emitting sources impinges optical radiation on the respective one of the photoelectrocatalytic elements upon electrical energization of the respective semiconductor light emitting source and a the respective one of the heaters is independently regulated separately to generate thermal energy and apply the thermal energy to only the respective one of the photoelectrocatalytic elements upon electrical energization of the respective heater.

28. A device according to claim 27 wherein the array of photoelectrocatalytic elements comprises a photoelectrocatalytic layer and an electrical contact layer thereon and wherein the array of semiconductor light emitting source sources comprises an array of light emitting diodes and/or laser diodes.

29. A device according to claim 28 wherein the photoelectrocatalytic layer includes first and second opposing faces, wherein the electrical contact layer is on the first face and wherein the array of light emitting diodes impinges optical radiation on the first face and/or on the second face.

30. A device according to claim 27 wherein the array of photoelectrocatalytic elements comprises a photoelectrocatalytic layer and a plurality of conductive contacts electrically connected thereto.

31. A device according to claim 27 wherein the array of photoelectrocatalytic elements comprises a plurality of spaced apart photoelectrocatalytic layers and a plurality of spaced apart conductive contacts electrically connected thereto.

32. A device according to claim 27 wherein the array of photoelectrocatalytic elements comprises a reference electrode and/or a charge balancing electrode.

33. A device according to claim 27 wherein the array of photoelectrocatalytic elements further comprises a transistor, a capacitor, a nanostructure, a diode, an amorphous structure, a piezoelectric structure and/or a surface acoustic wave structure.

34. A device according to claim 27 wherein the array of photoelectrocatalytic elements and the array of semiconductor light emitting sources include at least one common electrical contact.

35. A device according to claim 27 wherein the array of semiconductor light emitting sources includes a passivation layer and wherein the array of photoelectrocatalytic elements is at least partially on the passivation layer.

36. A device according to claim 27 further comprising a controller that is configured to selectively energize the array of semiconductor light emitting sources and the array of heaters and to detect a response to the thermal energy and the impingement of optical radiation upon the array of photoelectrocatalytic elements.

37. A device according to claim 27 wherein the array of photoelectrocatalytic elements is doped with deep level impurities and wherein the array of semiconductor light emitting sources is an array of visible and/or infrared light emitting diodes and/or laser diodes.

38. A device according to claim 27 wherein the array of photoelectrocatalytic elements comprises a metal oxide, wherein the array of semiconductor light emitting sources comprises an array of ultraviolet and/or a blue light emitting diodes and/or laser diodes.

39. A device according to claim 28 wherein the photoelectrocatalytic layer comprises a plurality of layers of a given photoelectrocatalytic material having at least two different impurities therein.

40. A device according to claim 28 wherein the photoelectrocatalytic layer comprises a plurality of layers of different photoelectrocatalytic materials.

41. A device according to claim 28 wherein the photoelectrocatalytic layer comprises oxide, carbide, nitride, arsenide, phosphide, sulfide and/or antimonide photoelectrocatalytic compounds and/or metal oxides, metal nitrides, metallic compounds and/or semimetallic compounds thereof.

42. A device according to claim 28 wherein the electrical contact comprises at least two interdigitated conductive contacts.

43. A device according to claim 36 wherein the controller is configured to repeatedly modulate the array of semiconductor light emitting sources and to detect an electrical response of the photoelectrocatalytic element in response thereto.

44. A device according to claim 36 further comprising a wireless transmitter that is responsive to the controller.

45. A sensing method, comprising:
energizing a respective one of an array of semiconductor light emitting sources to impinge optical radiation upon a respective one of an array of photoelectrocatalytic elements that is configured to be exposed to a fluid, if present, so that the respective one of the array of semiconductor light emitting sources impinges the optical radiation on the respective one of the array of photoelectrocatalytic elements;

energizing a respective one of an array of heaters that is separate from the array of semiconductor light emitting sources and is independently regulated to separately generate thermal energy and apply the thermal energy to the array of photoelectrocatalytic elements, so that the respective one of the heaters applies the thermal energy to only the respective one of the array of photoelectrocatalytic elements; and detecting a response of the array of photoelectrocatalytic elements in response to the energizing of the array of semiconductor light emitting sources and the array of heaters.

46. A method according to claim 45 wherein the fluid comprises a liquid and/or a gas and wherein the analyte comprises a pollutant, contaminant and/or a component of the fluid.

47. A method according to claim 45 wherein the fluid comprises respired gas and wherein the analyte comprises a component of the respired gas.

48. A method according to claim 45 wherein detecting a response of the array of photoelectrocatalytic elements comprises detecting a change in a conductivity, capacitance, inductance, impedance, net charge, optical property and/or mechanical property of the array of photoelectrocatalytic elements in response to the thermal energy and the impingement of optical radiation upon the array of photoelectrocatalytic elements.

49. A method according to claim 45 further comprising:
monitoring energy of the at least one analyte in the fluid, if present, resulting from the photoelectrocatalysis of the at least one analyte in response to the thermal energy and the impingement of optical radiation upon the array of photoelectrocatalytic elements.

50. A method according to claim 45 wherein energizing an array of semiconductor light emitting sources comprises repeatedly modulating the semiconductor light emitting source.

51. A method according to claim 45 further comprising repelling charged analyte from the array of photoelectrocatalytic elements.

52. A method according to claim 45 further comprising biasing the array of photoelectrocatalytic elements to reduce carrier recombination.

53. A sensor according to claim 1 wherein the array of heaters is configured to apply thermal energy to the array of photoelectrocatalytic elements so that the array of photoelectrocatalytic elements also responds to thermocatalysis of the at least one analyte in the fluid.

54. A sensor according to claim 1 wherein the array of heaters is configured to apply a thermal gradient in at least one direction along the array of photoelectrocatalytic elements.

55. A sensor according to claim 1 wherein the array of heaters comprises an array of filament heaters, monolithic patterned resistors, resistive heaters and/or radiative heaters.

56. A sensor according to claim 54 wherein the array of heaters comprises one or more array of localized filament heaters, monolithic patterned resistors, radiative heaters and/or graded filament heaters.

57. A sensor according to claim 1 wherein the array of heaters comprises an array of infrared heaters.

58. A sensor according to claim 1 wherein the array of photoelectrocatalytic elements comprises a plurality of photoelectrocatalytic electrodes and wherein the array of heaters comprises a plurality of heaters, a respective one of which is configured to apply the thermal energy to a respective one of the photoelectrocatalytic electrodes.

59. A sensor according to claim 1 wherein the array of heaters comprises a film that generates the thermal energy in response to impingement of light thereon.

60. A device according to claim 27 wherein the array of heaters is configured to apply a thermal gradient in at least one direction along the array of photoelectrocatalytic elements.

61. A device according to claim 27 wherein the array of heaters comprises an array of filament heaters, monolithic patterned resistors, resistive heaters and/or radiative heaters.

62. A device according to claim 60 wherein the array of heaters comprises one or more arrays of localized filament heaters, monolithic patterned resistors, radiative heaters and/or graded filament heaters.

63. A device according to claim 27 wherein the array of heaters comprises an array of infrared heaters.

64. A device according to claim 27 wherein the array of photoelectrocatalytic elements comprises a plurality of photoelectrocatalytic electrodes and wherein the array of heaters comprises a plurality of heaters, a respective one of which is configured to apply the thermal energy to a respective one of the photoelectrocatalytic electrodes.

65. A device according to claim 27 wherein the array of heaters comprises a film that generates the thermal energy in response to impingement of light thereon.

* * * * *

UNITED STATES PATENT AND TRADEMARK OFFICE
CERTIFICATE OF CORRECTION

PATENT NO. : 8,323,982 B2  
APPLICATION NO. : 11/745056  
DATED : December 4, 2012  
INVENTOR(S) : LeBoeuf et al.

Page 1 of 1

It is certified that error appears in the above-identified patent and that said Letters Patent is hereby corrected as shown below:

In the Claims:

Column 41, Claim 27, Line 45: Please correct "source and a the"
to read -- source and the --

Claim 28, Line 54: Please correct "light emitting source sources"
to read -- light emitting sources --

Signed and Sealed this
Seventeenth Day of September, 2013

Teresa Stanek Rea
*Deputy Director of the United States Patent and Trademark Office*